(12) United States Patent
Inoue et al.

(10) Patent No.: US 9,174,998 B2
(45) Date of Patent: Nov. 3, 2015

(54) (6S,9AS)-N-BENZYL-6-[(4-HYDROXY-PHENYL)METHYL]-4,7-DIOXO-8-({6-[3-(PIPERAZIN-1-YL)AZETIDIN-1-YL]PYRIDIN-2-YL}METHYL)-2-(PROP-2-EN-1-YL)-OCTAHYDRO-1H-PYRAZINO[2,1-C][1,2,4]TRIAZINE-1-CARBOXAMIDE COMPOUND

(71) Applicants: Eisai R&D Management Co., Ltd., Tokyo (JP); PRISM Pharma Co., Ltd., Yokohama-shi, Kanagawa (JP)

(72) Inventors: Satoshi Inoue, Tsukuba (JP); Yuji Yamamoto, Tsukuba (JP); Kentaro Iso, Tsukuba (JP)

(73) Assignees: Eisai R&D Management Co., Ltd., Tokyo (JP); PRISM Pharma Co., Ltd., Kanagawa (JP)

( * ) Notice: Subject to any disclaimer, the term of this patent is extended or adjusted under 35 U.S.C. 154(b) by 0 days.

(21) Appl. No.: 14/577,660

(22) Filed: Dec. 19, 2014

(65) Prior Publication Data

US 2015/0175615 A1     Jun. 25, 2015

(30) Foreign Application Priority Data

Dec. 25, 2013    (JP) .............................. P2013-267687

(51) Int. Cl.
| | | |
|---|---|---|
| C07D 487/04 | (2006.01) | |
| C07F 9/09 | (2006.01) | |
| C07D 401/14 | (2006.01) | |
| A61K 31/53 | (2006.01) | |
| A61K 35/00 | (2006.01) | |

(52) U.S. Cl.
CPC .............. C07D 487/04 (2013.01); A61K 31/53 (2013.01); C07F 9/09 (2013.01)

(58) Field of Classification Search
CPC .... C07D 487/04; C07D 401/14; A61K 31/53; A61K 45/06
USPC ............................................ 544/184; 514/243
See application file for complete search history.

(56) References Cited

U.S. PATENT DOCUMENTS

| | | | |
|---|---|---|---|
| 8,080,657 B2 * | 12/2011 | Chung et al. ................... | 544/184 |
| 2010/0286094 A1 | 11/2010 | Chung et al. | |

FOREIGN PATENT DOCUMENTS

| | | |
|---|---|---|
| JP | 2011-500666 | 1/2011 |
| JP | 2011-522037 | 7/2011 |
| JP | 2013-540774 | 11/2013 |
| WO | WO 2009/051397 | 4/2009 |
| WO | WO 2009/148192 | 12/2009 |

OTHER PUBLICATIONS

International Search Report and Written Opinion in International Application No. PCT/JP2014/083932, dated Mar. 17, 2015, 9 pages.
Barker and Clevers, "Mining the Wnt pathway for cancer therapeutics," Reviews Drug Discovery, Dec 2006, 5:997-1014.
Chen et al., "Small molecule-mediated disruption of Wnt-dependent signaling in tissue regeneration and cancer," Nat Chem Biol., Feb 2009, 5(2):100-107.
De Robertis et al., and characterization of a small-molecule inhibitor of Wnt " signaling in glioblastoma cells," Mol Cancer Ther, 2013, 12:1180-1189.
Emami et al., "A small molecule inhibitor of β-catenin/CREB-binding protein transcription," PNAS, Aug. 24, 2004, 101(34):12682-12687.
Gurney et al., "Wnt pathway inhibition via the targeting of Frizzled receptors results in decreased growth and tumorigenicity of human tumors," Pnas, Jul. 17, 2012, 109(29):11717-11722.
Hao et al., "Targeted Inhibition of β-Catenin/CBP Signaling Ameliorates Renal Interstitial Fibrosis," J Am Soc Nephrol., 2011, 22:1642-1653.
Henderson, Jr. et al , "Inhibition of Wnt/β-catenin/CREB binding protein(CBP) signaling reverses pulmonary fibrosis," PNAS, Aug. 10, 2010, 107(32):14309-14314.
Huang et al., "Tankyrase inhibition stabilizes axin and antagonizes Wnt signaling," Nature, 2009, 461:614-620.
Jiang et al., "Inactivating mutations of RNF43 confer Wnt dependency in pancreatic ductal adenocarcinoma," PNAS, Jul. 30, 2013, 110(31):12649-12654.

(Continued)

*Primary Examiner* — Venkataraman Balasubramanian
(74) *Attorney, Agent, or Firm* — Fish & Richardson P.C.

(57) ABSTRACT

A compound represented by formula (1) or pharmaceutically acceptable salt thereof:

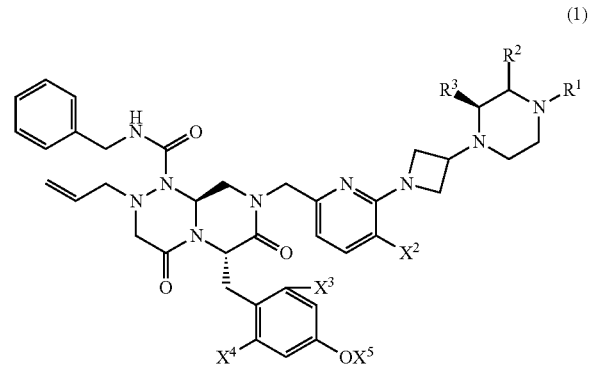

wherein $R^1$ is a $C_{1-6}$ alkyl group; $R^2$ and $R^3$ are the same or different from each other and each is a hydrogen atom or a $C_{1-6}$ alkyl group; $X^2$, $X^3$ and $X^4$ are the same or different from each other and each is a hydrogen atom or a halogen atom; and $X^5$ is a hydrogen atom or —P(=O)(OH)$_2$ has a Wnt Pathway modulating activity.

17 Claims, 3 Drawing Sheets

(56) References Cited

OTHER PUBLICATIONS

Lam et al., "I3-catenin signaling: a novel mediator of fibrosis and potential therapeutic target," Curr Opin Rheumatol., 2011, 23(6):562-567 (Author Manuscript).
Lehtio et al., "'Tankyrases as drug targets," FEBS J., 2013, 280:3576-3593.
Shitashige et al., "Traf2- and Nck-Interacting Kinase Is Essential for Wnt Signaling and Colorectal Cancer Growth," Cancer Res., 2010, 70:5024-5033.
Waaler et al., "Novel Synthetic Antagonists of Canonical Wnt Signaling Inhibit Colorectal Cancer Cell Growth," Cancer Res., 2011, 71:197-205.
Yao et al., "AV-65, a novel Wnt/β-catenin signal inhibitor, successfully suppresses progression of multiple myeloma in a mouse model," Blood Cancer J, 2011, 1:e43, 9 pages.

* cited by examiner

(6S,9AS)-N-BENZYL-6-[(4-HYDROXY-PHENYL)METHYL]-4,7-DIOXO-8-({6-[3-(PIPERAZIN-1-YL)AZETIDIN-1-YL]PYRIDIN-2-YL}METHYL)-2-(PROP-2-EN-1-YL)-OCTAHYDRO-1H-PYRAZINO[2,1-C][1,2,4]TRIA-ZINE-1-CARBOXAMIDE COMPOUND

TECHNICAL FIELD

The present invention relates to a (6S,9aS)-N-benzyl-6-[(4-hydroxyphenyl)methyl]-4,7-dioxo-8-({6-[3-(piperazin-1-yl)azetidin-1-yl]pyridin-2-yl}methyl)-2-(prop-2-en-1-yl)-octahydro-1H-pyrazino[2,1-c][1,2,4]triazine-1-carboxamide compound.

BACKGROUND ART

A Wnt signaling pathway is conserved regardless of the difference in the species of organisms, and is known as an important pathway involved in the development, differentiation and maintenance of living organisms. In recent years, however, it is reported that the constitutive activation of the pathway is involved in the development of malignant transformation of fibrosis and cancer. It is known that, particularly in colorectal cancer, melanoma, endometrial cancer, liver cancer and prostate cancer, the Wnt signaling pathway can be activated constitutively by the suppressible mutation of adenomatous polyposis coli (APC) or activating mutation of β-catenin or the like. It is also known that, in pancreatic cancer, hematological cancer, liver cancer and the like, the Wnt signaling pathway can be activated after the treatment with a known anti-tumor agent.

In Non Patent Literatures 1 and 2, it is described that an excellent anti-tumor activity can be achieved by inhibiting the Wnt signaling pathway. In Non Patent Literatures 12, 13 and 14, it is described that an excellent effect on fibrosis can be achieved by inhibiting the Wnt signaling pathway. Thus, the Wnt signaling pathway has attracted attention as a novel target for the treatment of tumors or the treatment of fibrosis.

In Non Patent Literatures 3, 4, 5, 6, 7, 8, 9, 10 and 11, compounds or antibodies capable of inhibiting the Wnt signaling pathways are disclosed, and it is reported that the compounds or the antibodies can act on Tankyrase, Traf2- and Nck-interacting kinase (TNIK), Porcupine, Frizzled Receptor and the like.

Furthermore, compounds each having an octahydro-1H-pyrazino[2,1-c][1,2,4]triazine backbone are known as modulator of the Wnt signaling pathway, and the relationship between the compounds and diseases such as cancer and fibrosis is pointed out (Patent Literatures 1 to 3).

CITATION LIST

Patent Literature

[Patent Literature 1] WO 2009/051397
[Patent Literature 2] US 2010/0286094
[Patent Literature 3] WO 2009/148192

Non Patent Literature

[Non Patent Literature 1] Nick Barker et al., "Mining the Wnt pathway for cancer therapeutics", Nature reviews Drug discovery 2006 December; 5(12):997-1014.
[Non Patent Literature 2] Katayoon H. Emami et al., "A small molecule inhibitor of beta-catenin/CREB-binding protein transcription", Proc. Natl. Acad. Sci. USA., 2004, 101(34), p. 12682-12687.
[Non Patent Literature 3] Baozhi Chen et al., "Small molecule-mediated disruption of Wnt-dependent signaling in tissue regeneration and cancer", Nat Chem Biol., 2009, 5(2), p. 100-107.
[Non Patent Literature 4] Shih-Min A. Huang et al., "Tankyrase inhibition stabilizes axin and antagonizes Wnt signalling", Nature, 2009, 461, p. 614-620.
[Non Patent Literature 5] Lari Lehtio et al., "Tankyrases as drug targets", The FEBS Journal, 2013, 280, 3576-3593.
[Non Patent Literature 6] Mild Shitashige et al., "Traf2- and Nck-Interacting Kinase Is Essential for Wnt Signaling and Colorectal Cancer Growth", Cancer Res., 2010, 70(12), 5024-5033.
[Non Patent Literature 7] Austin Gurney et al., "Wnt pathway inhibition via the targeting of Frizzled receptors results in decreased growth and tumorigenicity of human tumors", Proc. Natl. Acad. Sci. USA., 2012, 109(29), 11717-11722.
[Non Patent Literature 8] Xiaomo Jiang et al., "Inactivating mutations of RNF43 confer Wnt dependency in pancreatic ductal adenocarcinoma", Proc. Natl. Acad. Sci. USA., 2013, 110(31), 12649-12654.
[Non Patent Literature 9] Jo Waaler et al., "Novel Synthetic Antagonists of Canonical Wnt Signaling Inhibit Colorectal Cancer Cell Growth", Cancer Res, 2011, 71(1), 197-205.
[Non Patent Literature 10] H Yao et al., "AV-65, a novel Wnt/β-catenin signal inhibitor, successfully suppresses progression of multiple myeloma in a mouse model", Blood Cancer Journal, 2011, 1, e43.
[Non Patent Literature 11] De Robertis A et al., "Identification and characterization of a small-molecule inhibitor of Wnt signaling in glioblastoma cells", Mol Cancer Ther., 2013, 12(7), 1180-1189.
[Non Patent Literature 12] Anna P. Lam et al., "β-catenin signaling: a novel mediator of fibrosis and potential therapeutic target", Curr Opin Rheumatol. 2011 November; 23(6): 562-567.
[Non Patent Literature 13] Sha Hao et al., "Targeted Inhibition of β-Catenin/CBP Signaling Ameliorates Renal Interstitial Fibrosis", J. Am. Soc. Nephrol. 22: 1642-1653, 2011.
[Non Patent Literature 14] William R. Henderson, Jr. et al., "Inhibition of Wnt/3-catenin/CREB binding protein (CBP) signaling reverses pulmonary fibrosis", Proc. Natl. Acad. Sci. USA., 2010, 107(32), 14309-14314.

SUMMARY OF INVENTION

Technical Problem

The problem to be solved by the invention of the present application is to provide a compound having a Wnt Pathway modulating activity.

Solution to Problem

As a result of exhaustive studies to solve the above-mentioned problem, the present inventors have completed the present invention. That is, the present invention relates to the following [1] to [21]:

[1] A compound represented by formula (1) or pharmaceutically acceptable salt thereof:

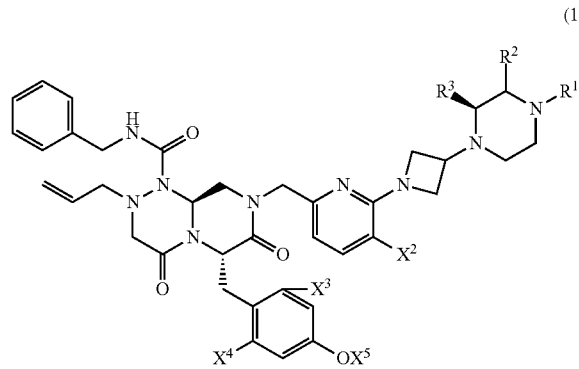

(1)

wherein R¹ is a $C_{1-6}$ alkyl group; R² and R³ are the same or different from each other and each is a hydrogen atom or a $C_{1-6}$ alkyl group; X², X³ and X⁴ are the same or different from each other and each is a hydrogen atom or a halogen atom; and X⁵ is a hydrogen atom or —P(=O)(OH)₂.

[2] The compound or pharmaceutically acceptable salt thereof according to [1], wherein R¹ is a methyl group, an ethyl group or an isopropyl group.

[3] The compound or pharmaceutically acceptable salt thereof according to [1], wherein R² and R³ are the same or different from each other and each is a hydrogen atom or a methyl group.

[4] The compound or pharmaceutically acceptable salt thereof according to [1], wherein X² is a hydrogen atom or a fluorine atom.

[5] The compound or pharmaceutically acceptable salt thereof according to [1], wherein X³ is a hydrogen atom or a fluorine atom.

[6] The compound or pharmaceutically acceptable salt thereof according to [1], wherein X⁴ is a hydrogen atom or a fluorine atom.

[7] A compound or pharmaceutically acceptable salt thereof selected from:

(6S,9aS)-N-benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2-fluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3S)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-d-yl)-octahydro-1H-pyrazino[2,1-c][1,2,4]triazine-1-carboxamide, (6S,9aS)-N-benzyl-8-((6-(3-((3R)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((2S)-2,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-(4-ethylpiperazin-1-yl)azetidin-1-yl)-5-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((5-fluoro-6-(3-(4-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide, (6S,9aS)-N-benzyl-6-((2-fluoro-4-hydroxyphenyl)methyl)-8-((5-fluoro-6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2-fluoro-4-hydroxyphenyl)methyl)-4,7-dioxo-2-(prop-2en-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide, (6S,9aS)-N-benzyl-6-((2,6-difluoro-4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-(4-methypiperazino-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((2S)-2,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3S)-3,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((2S)-2,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3S)-4-ethyl-3-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-3-((3R)-4-ethyl-3-methylpiperazin-1-yl)azetidin-1-yl)pyridin-2-yl)methyl-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3S)-4-ethyl-3-methylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3R)-4-ethyl-3-methylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3S)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3R)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3R)-3,4-dimethylpiperazin-1-yl)azetidine-1-yl)-5-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, 4-(((6S,9aS)-1-(benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate, and, 4-(((6S,9aS)-1-(benzylcarbamoyl)-8-((6-(3-(4-ethylpiperazin-1-yl)azetidin-1-yl)pyridin-2-yl)methyl-4,7-dioxo-2-(prop-2-en-1-yl)-octahydro-1H-pyrazino[2,1-c][1,2,4]triazin-6-yl)methyl)phenyl dihydrogen phosphate.

[8] A compound or pharmaceutically acceptable salt thereof selected from:

(6S,9aS)-N-benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2-fluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-((6-(3-((3S)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3R)-3,4-dim ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((2S)-2,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((5-fluoro-6-(3-(4-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((2S)-2,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3S)-3,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((2S)-2,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3S)-4-ethyl-3-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-3-((3R)-4-ethyl-3-methylpiperazin-1-yl)azetidin-1-yl)pyridin-2-yl)methyl-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3S)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, 4-(((6S,9aS)-1-(benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate, and 4-(((6S,9aS)-1-(benzylcarbamoyl)-8-((6-(3-(4-ethylpiperazin-1-yl)azetidin-1-yl)pyridin-2-yl)methyl-4,7-dioxo-2-(prop-2-en-1-yl)-octahydro-1H-pyrazino[2,1-c][1,2,4]triazin-6-yl)methyl)phenyl dihydrogen phosphate.

[9] (6S,9aS)-N-Benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

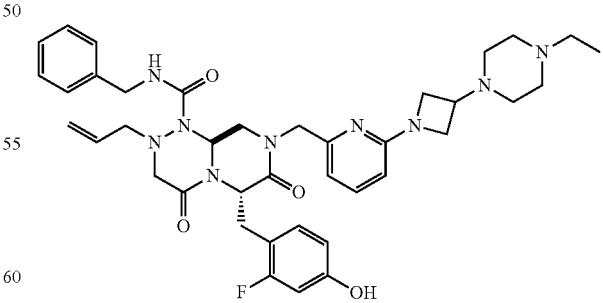

[10] (6S,9aS)-N-Benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

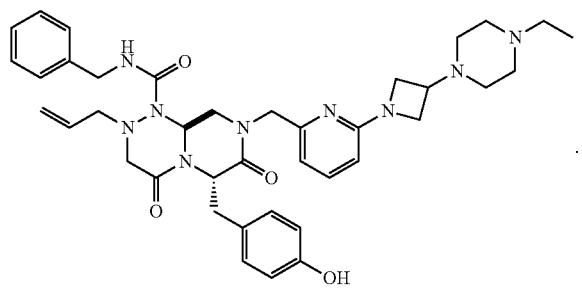 [SMILES: C=CCN1CC(=O)N2[C@@H](Cc3ccc(O)cc3)C(=O)N(Cc3cccc(N4CC(N5CCN(CC)CC5)C4)n3)C[C@@H]2N1C(=O)NCc1ccccc1]

[11] (6S,9aS)-N-Benzyl-6-((2-fluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide or a pharmaceutically acceptable salt thereof:

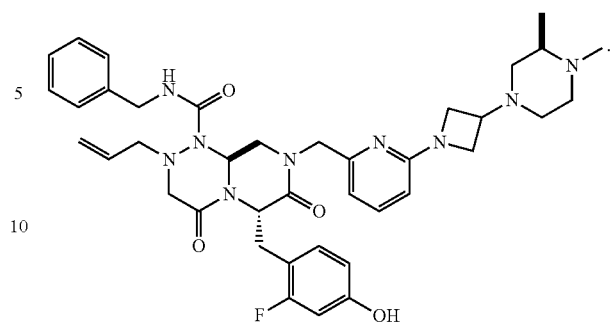

[14] (6S,9aS)-N-Benzyl-8-((6-(3-((2S)-2,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

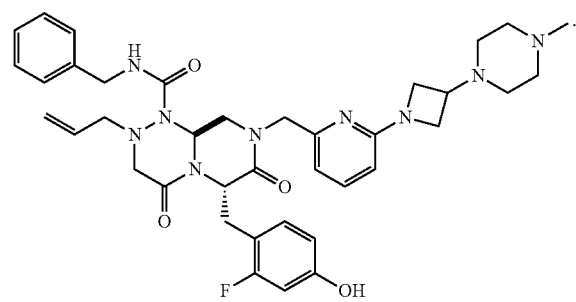

[12] (6S,9aS)-N-Benzyl-8-((6-(3-((3S)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

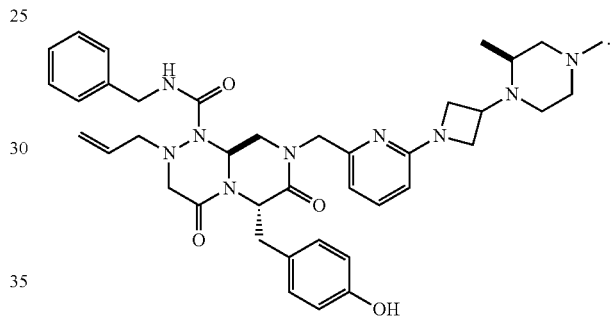

[15] 4-(((6S,9aS)-1-(Benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate or a pharmaceutically acceptable salt thereof:

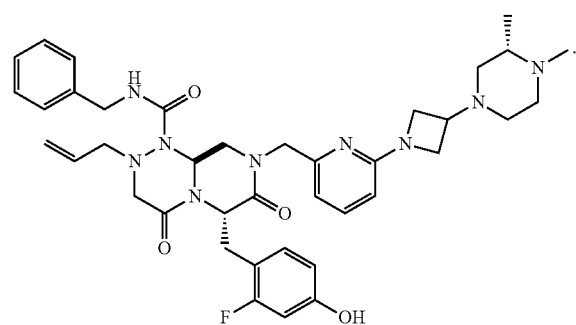

[13] (6S,9aS)-N-Benzyl-8-((6-(3-((3R)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

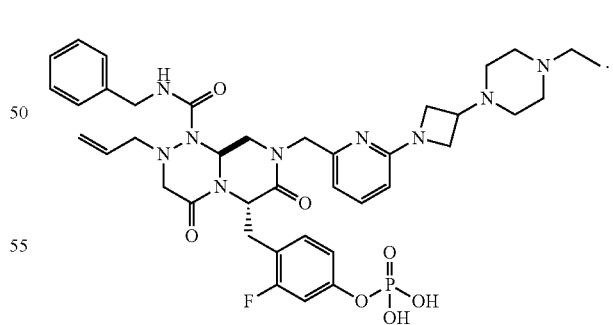

[16] 4-(((6S,9aS)-1-(Benzylcarbamoyl)-8-((6-(3-(4-ethylpiperazin-1-yl)azetidin-1-yl)pyridin-2-yl)methyl-4,7-dioxo-2-(prop-2-en-1-yl)-octahydro-1H-pyrazino[2,1-c][1,2,4]triazin-6-yl)methyl)phenyl dihydrogen phosphate or a pharmaceutically acceptable salt thereof:

[17] A pharmaceutical composition comprising the compound or pharmaceutically acceptable salt thereof according to any one of [1] to [16].

[18] A therapeutic or prophylactic agent for cancer or fibrosis, comprising the compound or pharmaceutically acceptable salt thereof according to any one of [1] to [16].

[19] A method for treating or preventing cancer or fibrosis, comprising administering the compound or pharmaceutically acceptable salt thereof according to any one of [1] to [16] to a patient.

[20] The compound or pharmaceutically acceptable salt thereof according to any one of [1] to [16] for use in treating or preventing cancer or fibrosis.

[21] Use of the compound or pharmaceutically acceptable salt thereof according to any one of [1] to [16] in the manufacture of a therapeutic or prophylactic agent for cancer or fibrosis.

Advantageous Effects of Invention

The compound according to the present invention has a Wnt pathway modulating activity and therefore has potential use as a therapeutic agent for cancer, fibrosis and the like.

DESCRIPTION OF EMBODIMENTS

Figure 1:
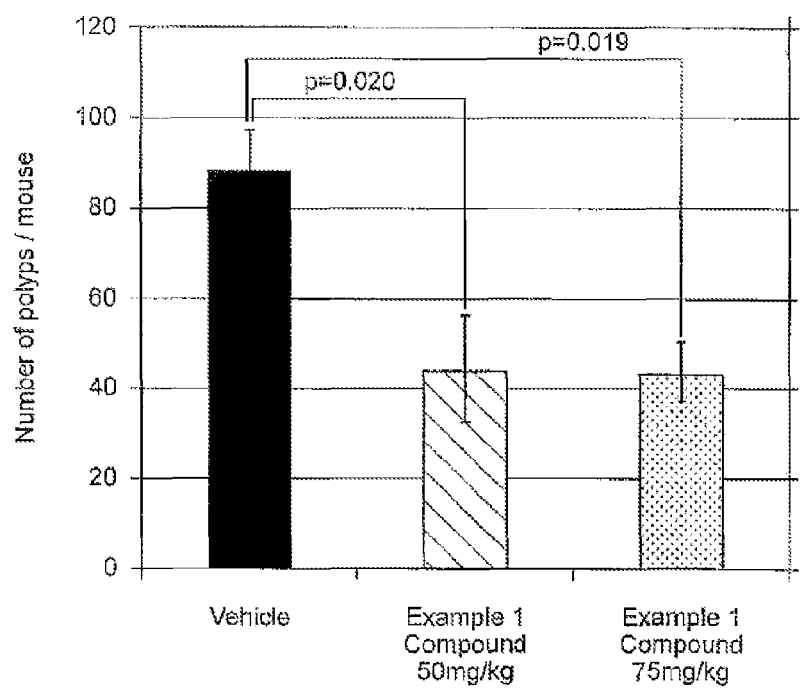
FIG. 1 shows the results of Test Example 6.

Hereinbelow, the contents of the present invention will be described in detail. In the description, the term "the compound according to the present invention" means a compound represented by formula (1) or pharmaceutically acceptable salt thereof. The compound represented by formula (1) is sometimes referred to as "compound (1)".

In the compound according to the present invention, a moiety of formula (1) of which the stereochemical feature is defined clearly has a structure as shown in the formula, and a moiety of formula (1) which is the other part of the aforementioned moiety and of which the stereochemical feature is not defined clearly may contain a stereoisomer and the stereoisomer may be one type of stereoisomer or a mixture of stereoisomers. The compound may include a crystal polymorphism thereof. The crystal polymorphism is not limited to a specific crystal form, and may be a single crystal form or a mixture of crystal forms. The compound of the present invention includes an amorphous form, and also includes an anhydride and a solvate such as a hydrate.

Hereinbelow, the meaning of the terms, the symbols and the like described in the present description will be explained to describe the present invention in detail.

The term "a halogen atom" as used herein refers to a fluorine atom, a chlorine atom, a bromine atom or an iodine atom.

The term "a $C_{1-6}$ alkyl group" as used herein refers to a linear or branched alkyl group having 1 to 6 carbon atoms, and specific examples of the group include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 1-hexyl group, a 2-hexyl group and a 3-hexyl group.

$R^1$ in the compound represented by formula (1) is a $C_{1-6}$ alkyl group. $R^1$ is preferably a methyl group, an ethyl group or an isopropyl group, and R is more preferably an ethyl group.

In the compound represented by formula (1), $R^2$ and $R^3$ are the same or different from each other and each is a hydrogen atom or a $C_{1-6}$ alkyl group. Preferably, $R^2$ and $R^3$ are the same or different from each other and each is a hydrogen atom or a methyl group. More preferably, both of $R^2$ and $R^3$ are a hydrogen atom.

$X^2$ in the compound represented by formula (1) is a hydrogen atom or a halogen atom, preferably a hydrogen atom.

$X^3$ in the compound represented by formula (1) is a hydrogen atom or a halogen atom, preferably a hydrogen atom or a fluorine atom.

$X^4$ in the compound represented by formula (1) is a hydrogen atom or a halogen atom, preferably a hydrogen atom or a fluorine atom.

$X^5$ in the compound represented by formula (1) is a hydrogen atom or $-P(=O)(OH)_2$, preferably a hydrogen atom.

The term "pharmaceutically acceptable salt" as used in the present description is not particularly limited as long as the pharmaceutically acceptable salt is a salt formed with the compound represented by formula (1) and is pharmaceutically acceptable, and examples the pharmaceutically acceptable salt include an inorganic acid salt, an organic acid salt, an inorganic base salt, an organic base salt, and an acidic or basic amino acid salt.

Preferred examples of the inorganic acid salt include a hydrochloride, a hydrobromide, a sulfate salt, a nitrate salt and a phosphate salt, and preferred examples of the organic acid salt include: a carboxylate salt such as an acetate salt, a succinate salt, a fumarate salt, a maleate salt, a tartrate salt, a citrate salt, a lactate salt, a stearate salt, a benzoate salt and a mandelate salt; and a sulfonate salt such as a methanesulfonate salt, an ethanesulfonate salt, a p-toluenesulfonate salt and a benzenesulfonate salt.

Preferred examples of the inorganic base salt include: an alkali metal salt such as a sodium salt and a potassium salt; an alkali earth metal salt such as a calcium salt and a magnesium salt; an aluminum salt; and an ammonium salt. Preferred examples of the organic base salt include: a diethylamine salt, a diethanolamine salt, a meglumine salt and a N,N'-dibenzylethylenediamine salt.

Preferred examples of the acidic amino acid salt include an aspartate salt and a glutamate salt. Preferred examples of the basic amino acid salt include an arginine salt, a lysine salt and an ornithine salt.

The compound represented by formula (1), such as the compounds described in Examples 1 to 6, 8, 12, 13, 15 to 19 and 22 mentioned below, particularly the compounds described in Examples 1 to 6, can be used as an orally applicable agent from the viewpoint of parameters such as solubility, metabolic stability and membrane permeability.

The compound represented by formula (1) can be produced by a method as mentioned below. The method for producing the compound represented by formula (1) is not limited to that method, and may be produced by modifying the above-mentioned method by a person skilled in the art on the basis of common knowledge.

[Production Method 1] Method for Producing Compound (1A)

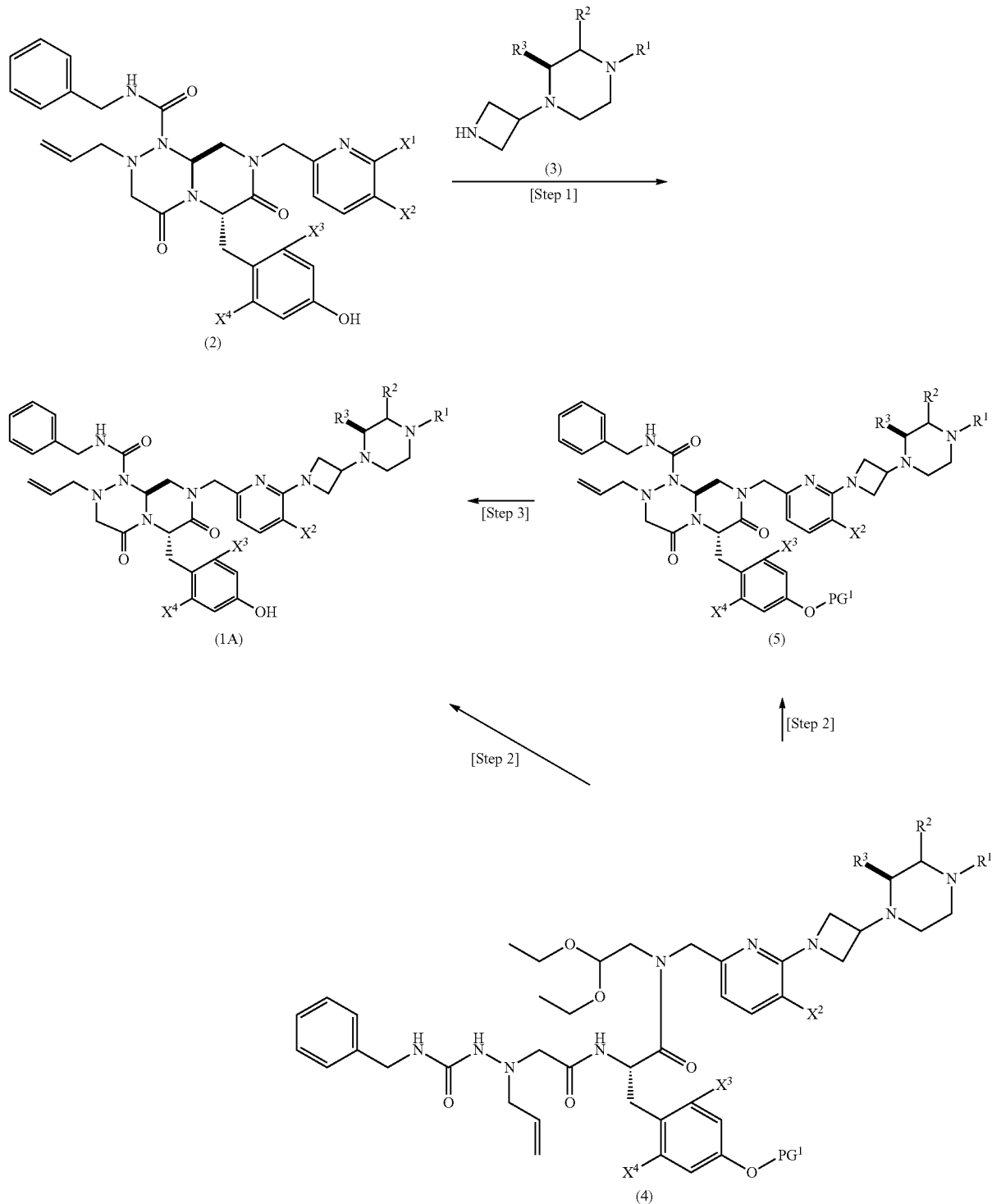

wherein $R^1$, $R^2$, $R^3$, $X^2$, $X^3$ and $X^4$ are as defined above; $X^1$ is a halogen atom; and $PG^1$ is a protecting group for a phenolic hydroxy group.

The method for producing compound (1A), which is one of the compounds represented by formula (1) wherein $X^5$ is a hydrogen atom, is mentioned below.

Compound (2) can be produced by a method described in Production examples or Production Method 2 in Examples or the like.

As for compound (3), a commercially available compound may be used without any modification. Alternatively compound (3) may be produced from a commercially available compound by a known method. Alternatively, compound (3) can be produced by a method described in Production examples or Production Method 3 in Examples or the like.

Compound (4) can be produced by a method described in Production examples or Production Method 4 in Examples or the like.

[Step 1]

This step is a step of reacting compound (2) with an amine represented by compound (3) or a salt thereof while irradiating the compounds with a microwave in the presence of a base to produce compound (1A). The solvent to be used in the reaction is not particularly limited as long as the solvent can dissolve starting materials to some extent and does not inhibit the reaction. As the solvent, an amide-type solvent such as N,N-dimethylformamide and N-methylpyrrolidinone; a sulfoxide-type solvent such as dimethyl sulfoxide; or a mixed solvent of any two or more of these solvents can be used. As the base to be used in the reaction, an organic base such as N,N-diisopropylethylamine, triethylamine, 1,8-diazabicyclo[5.4.0]undec-7-ene (also referred to as "DBU") and pyridine can be used, or compound (3) itself can also be used. The compound (3) can be used in an amount of 1 equivalent or more, preferably 1.5 to 5 equivalents, relative to the amount of compound (2). The base can be used in an amount of 1 equivalent or more, preferably 1.5 to 5 equivalents, relative to the amount of compound (2). The reaction temperature ranges from 50° C. to a reflux temperature, and the reaction time ranges from 1 to 72 hours.

The compound (1A) can be produced from compound (2) by a method described as alternative step (1) below.

Alternative step (1): this step is a step of heating compound (2) and compound (3) in a solvent to produce compound (1A). The solvent to be used in the reaction is not particularly limited as long as the solvent can dissolve starting materials to some extent and does not inhibit the reaction. For example, a pyridine-type solvent such as pyridine or a mixed solvent of the aforementioned solvent with water can be used. For the purpose of achieving good yield, a base such as potassium carbonate and cesium carbonate may be added in an amount of 1 to 2 equivalents. The compound (3) can be used in an amount of 1 equivalent or more, preferably 1.5 to 5 equivalents, relative to the amount of compound (2). The reaction temperature ranges from 50° C. to a reflux temperature, and the reaction time ranges from 10 minutes to 72 hours.

[Step 2]

This step is a step of reacting compound (4) under acidic conditions to convert an acetal moiety to an aldehyde, and then carrying out a cyclization reaction to produce compound (5). When a protective group for which the deprotection reaction proceeds under the acidic conditions of the present step is used as a protective group $PG^1$ for a phenolic hydroxy group, such as a tert-butyl group, the above-mentioned cyclization reaction as well as the removal of the protective group $PG^1$ occur, leading to the production of compound (1A). As the acid to be used in the reaction, formic acid, p-toluenesulfonic acid or the like can be used. The solvent to be used in the reaction is not particularly limited as long as the solvent can dissolve starting materials to some extent and does not inhibit the reaction. For example, an ether-type solvent such as tetrahydrofuran, tert-butyl methyl ether and 1,4-dioxane; an aprotic polar solvent such as N,N-dimethylformamide, N,N-dimethylacetamide, dimethyl sulfoxide, sulfolane, N-methylpyrrolidinone, 1,3-dimethyl-2-imidazolidinone and hexamethylphosphoramide; a nitrile-type solvent such as acetonitrile and propionitrile; a halogen-containing solvent such as dichloromethane and chloroform; an aromatic hydrocarbon-type solvent such as benzene and toluene; and water may be used. Alternatively, an acid itself or a mixed solvent of any two or more of the aforementioned solvents may also be used. The acid can be used in an amount ranging from a catalytic amount to a solvent amount, preferably 3 equivalents to a solvent amount, relative to the amount of compound (4). The reaction temperature ranges from room temperature to a reflux temperature, and the reaction time ranges from 10 minutes to 168 hours.

[Step 3]

This step is a step of removing the protective group $PG^1$ for the phenolic hydroxy group in compound (5) to produce compound (1A). The conditions for the reaction are varied depending on the types of the protective group $PG^1$ for the phenolic hydroxy group to be used. For example, when a benzylether-type protective group such as a benzyl group is to be removed, the reaction is carried out under acidic conditions to produce compound (1A). As the acid to be used, an organic acid such as trifluoroacetic acid and methanesulfonic acid; an inorganic acid such as sulfuric acid; and a Lewis acid such as boron trifluoride diethyl etherate can be used. For the purpose of obtaining better results, an additive such as thioanisole and pentamethylbenzene may be added to the reaction. The solvent to be used in the reaction is not particularly limited as long as the solvent can dissolve starting materials to some extent and does not inhibit the reaction. Preferably, an ether-type solvent such as diethyl ether and tetrahydrofuran and a halogen-containing solvent such as dichloromethane can be used. Alternatively, an acid itself or a mixed solvent of any two or more of the aforementioned solvents may be used. As the additive, thioanisole, ethanethiol, dl-methionine, pentamethylbenzene and the like can be used. The acid can be used in an amount of 1 equivalent to a solvent amount relative to the amount of compound (5). The additive can be used in an amount of 1 to 5 equivalents relative to the amount of compound (5). The reaction temperature ranges from 0° C. to a reflux temperature, and the reaction time ranges from 10 minutes to 72 hours.

[Production Method 2] Method for Producing Compound (2)

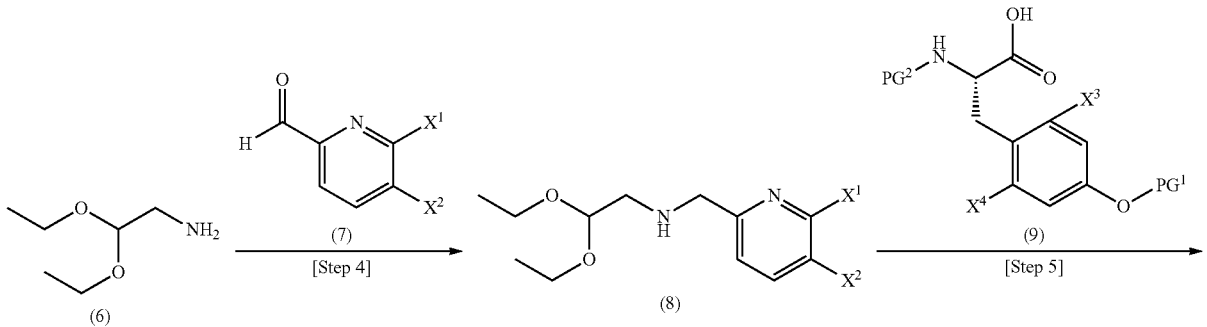

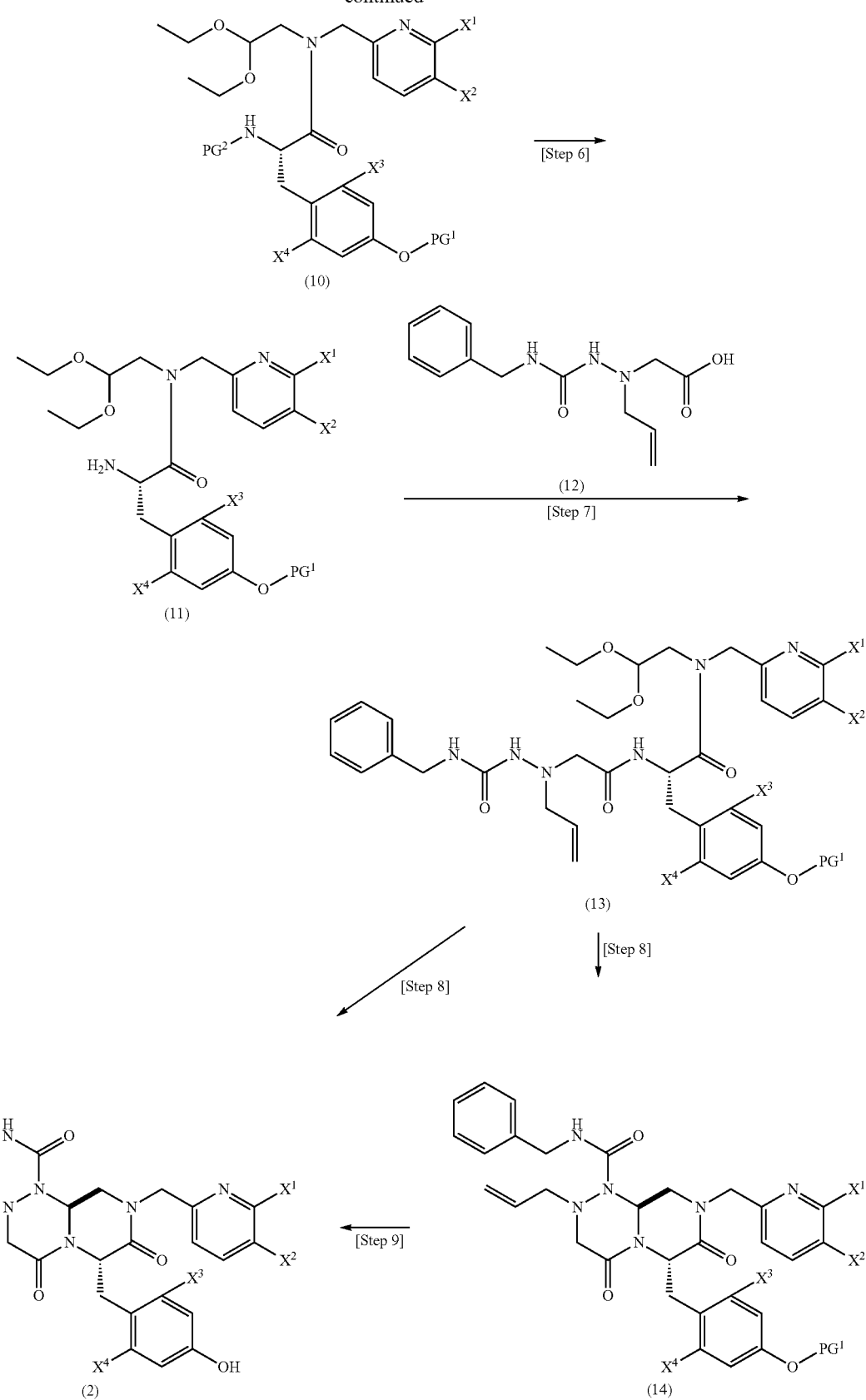

wherein, $X^1$, $X^2$, $X^3$, $X^4$ and $PG^1$ are as defined in the above-mentioned definitions; and $PG^2$ is a protective group for an amino group.

With respect to each of compound (6) and compound (7), a commercially available compound may be used without any modification, or the compound may be produced from a commercially available compound by a known method. Alternatively, the compound may be produced by a method described in Production Examples in Examples or the like.

With respect to compound (9), a commercially available compound may be used without any modification, or the compound may be produced from a commercially available compound by a known method, such as a method described in J. Am. Chem. Soc. 2010, 132, 863-872 or the like. Alternatively, the compound may be produced by a method described in Production Examples in Examples or the like.

With respect to compound (12), a commercially available compound may be used without any modification, or the compound may be produced from a commercially available compound by a known method, such as a method described in International Publication No. 2009/148192 or the like.

[Step 4]

This step is a step of reacting compound (7) with compound (6) or a salt thereof to perform reductive amination, thereby producing compound (8). For the purpose of accelerating the reaction, an acid such as acetic acid and hydrochloric acid can be added. The solvent to be used in the reaction is not particularly limited as long as the solvent can dissolve starting materials to some extent and does not inhibit the reaction. For example, an ether-type solvent such as 1,4-dioxane and tetrahydrofuran; an alcohol-type solvent such as methanol and ethanol; a halogen-containing solvent such as dichloromethane and chloroform; an amide-type solvent such as N,N-dimethylformamide and N-methylpyrrolidinone; a sulfoxide-type solvent such as dimethyl sulfoxide; or a mixed solvent comprising any two or more of the aforementioned solvents can be used. As a reducing agent, lithium aluminum hydride, sodium borohydride, sodium cyanoborohydride, sodium triacetoxyborohydride and 2-picoline-borane complex can be used. In place of the reducing agent, a reduction reaction by catalytic hydrogenation using a catalyst described in alternative step (2) described in step 6 may be used. The compound (7) can be used in an amount of 1 to 2 equivalents relative to the amount of compound (6). The amount of the reducing agent to be used varies depending on the types of the reducing agent, and the reducing agent can be used in an amount of 0.25 to 5 equivalents relative to the amount of compound (6). When an acid is added, the acid can be added in an amount ranging from a catalytic amount to a solvent amount relative to the amount of compound (6). The reaction temperature ranges from 0° C. to a reflux temperature, and the reaction time ranges from 5 minutes to 24 hours.

[Step 5]

This step is a step of reacting compound (9) or a salt thereof with compound (8) or a salt thereof in the presence of a condensing agent to produce compound (10). The solvent to be used in the reaction is not particularly limited as long as the solvent can dissolve starting materials to some extent and does not inhibit the reaction. For example, a halogen-containing solvent such as dichloromethane and chloroform; an ether-type solvent such as tetrahydrofuran and 1,4-dioxane; an amide-type solvent such as N,N-dimethylformamide and N-methylpyrrolidinone; a sulfoxide-type solvent such as dimethyl sulfoxide; a nitrile-type solvent such as acetonitrile and propionitrile; an ester-type solvent such as ethyl acetate; or a mixed solvent comprising any two or more of the aforementioned solvents can be used. As the condensing agent, HATU (O-(7-azabenzotriazol-1-yl)-N,N,N',N'-tetramethyluronium hexafluorophosphate), HBTU (O-(benzotriazol-1-yl)-N,N,N',N'-tetramethyluronium hexafluorophosphate), TBTU (O-(benzotriazol-1-yl)-N,N,N',N'-tetramethyluronium tetrafluoroborate), DMT-MM (4-(4,6-dimethoxy-1,3,5-triazin-2-yl)-4-methylmorpholinium chloride n-hydrate), Bop (1H-1,2,3-benzotriazol-1-yloxytris(dimethylamino) phosphonium hexafluorophosphate), WSC (1-ethyl-3-(3-dimethylaminopropyl)carbodiimide hydrochloride), DCC (N,N-dicyclohexylcarbodiimide) can be used. For the purpose of accelerating the reaction, a catalytic amount of 4-dimethylaminopyridine or 1-hydroxybenzotriazole may be added. A base such as triethylamine can be added in an amount of 1 to 5 equivalents and the amount may vary depending on the types of the condensing agent to be used. The compound (8) can be used in an amount of 1 to 3 equivalents, preferably 1 to 1.5 equivalents, relative to the amount of compound (9). The condensing agent can be used in an amount of 1 to 3 equivalents, preferably 1 to 1.5 equivalents relative to the amount of compound (9). The reaction temperature ranges from 0° C. to a reflux temperature, and the reaction time ranges from 10 minutes to 48 hours.

[Step 6]

This step is a step of removing the protective group for the amino group in compound (10) to produce compound (11). The conditions for the deprotection vary depending on the types of the protective group for the amino group to be used. For example, when a 9-fluorenylmethyloxycarbonyl (Fmoc) group or the like is used as the protective group for the amino group, compound (11) can be produced by carrying out the reaction under the basic conditions. The solvent to be used in the reaction is not particularly limited as long as the solvent can dissolve starting materials to some extent and does not inhibit the reaction, and a halogen-containing solvent such as dichloromethane and chloroform, an ether-type solvent such as tetrahydrofuran and 1,4-dioxane, an amide-type solvent such as N,N-dimethylformamide and N-methylpyrrolidinone; a sulfoxide-type solvent such as dimethyl sulfoxide; a nitrile-type solvent such as acetonitrile and propionitrile; an alcohol-type solvent such as methanol and ethanol; an ester-type solvent such as ethyl acetate; water; or a mixed solvent comprising any two or more of the aforementioned solvents can be used. A base itself can also be used as the solvent, as long as the base can dissolve the starting material to some extent and does not inhibit the reaction. As the base, an organic base such as piperidine, morpholine, dimethylamine, diethylamine, dicyclohexylamine, 4-dimethylaminopyridine, N,N-diisopropylethylamine, triethylamine and DBU; or an inorganic base such as sodium hydrogen carbonate, sodium carbonate, potassium carbonate and cesium carbonate can be used. The base can be used in an amount ranging from a catalytic amount to a solvent amount, preferably 1 equivalent to a solvent amount, relative to the amount of compound (10). The reaction temperature ranges from 0° C. to a reflux temperature, and the reaction time ranges from 5 minutes to 96 hours.

Compound (11) can also be produced by the method described in Alternative step (2) mentioned below, i.e., by carrying out the deprotection reaction of the protective group for the amino group in compound (10), in which a benzyloxycarbonyl (Cbz or Z) group, a 9-fluorenylmethyloxycarbonyl (Fmoc) group or the like is used as the protective group for the amino group.

Alternative step (2): this step is a step of producing compound (11) by a catalytic hydrogenation reaction. The solvent to be used in the reaction is not particularly limited, as long as the solvent can dissolve the starting material to some extent and does not inhibit the reaction. For example, an alcohol-type solvent such as methanol and ethanol; an ether-type solvent such as tetrahydrofuran; an amide-type solvent such as N,N-dimethylformamide and N-methylpyrrolidinone; a nitrile-type solvent such as acetonitrile and propionitrile; an ester-type solvent such as ethyl acetate; acetic acid; water; or a mixed solvent comprising any two or more of the aforementioned solvents can be used. As the catalyst to be used in this step, palladium-carbon or palladium hydroxide-carbon can be used. The catalyst can be used in an amount of a catalytic amount or more relative to the amount of compound (10). The reaction temperature ranges from room temperature to a reflux temperature, and the reaction time ranges from 10 minutes to 48 hours.

[Step 7]

This step is a step of reacting compound (12) or a salt thereof with compound (11) or a salt thereof in the presence of a condensing agent to produce compound (13). The compound (13) can be produced in the similar manner as in step 5.

[Step 8]

This step is a step of reacting compound (13) under acidic conditions to convert an acetal moiety to an aldehyde and then carrying out a cyclization reaction to produce compound (14). The compound (14) can be produced in the similar manner as in step 2. The conditions for the deprotection vary depending on the types of the protective group for the phenolic hydroxy group. For example, when the protective group PG for the phenolic hydroxy group is a protective group of which the deprotection can proceed under the acidic conditions employed in this step, such as a tert-butyl group, the deprotection reaction proceeds simultaneously with the cyclization in this step, thereby producing compound (2).

[Step 9]

This step is a step of removing the protective group for the phenolic hydroxy group in compound (14) to produce compound (2). The conditions for the deprotection vary depending on the types of the protective group for the phenolic hydroxy group. For example, when a benzyl ether group such as a benzyl group, is used as the protective group for the phenolic hydroxy group, compound (2) can be produced by the same reaction conditions in step 3 for the deprotection.

[Production Method 3] Method for Producing Compound (3)

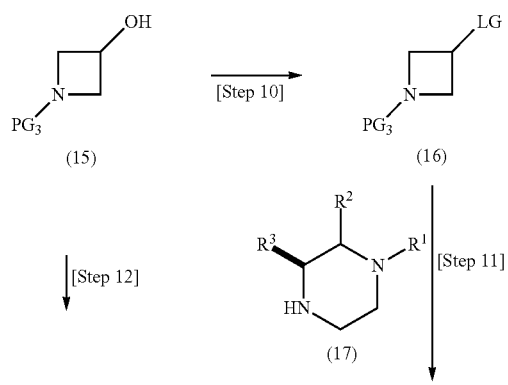

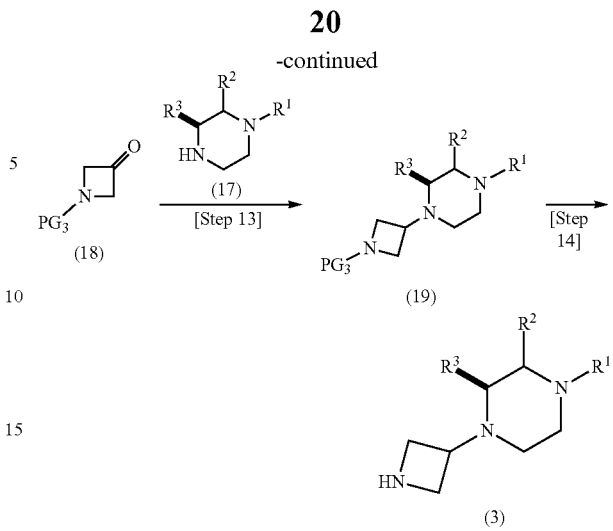

wherein $R^1$, $R^2$ and $R^3$ are as defined in the definition; LG is a leaving group; and $PG^3$ is a protective group for an amino group.]

With respect to each of compound (15), compound (16), compound (17), compound (18) and compound (19), a commercially available compound may be used without any modification, or the compound may be produced from a commercially available compound by a known method. Alternatively, each of the compounds may be produced by a method described in Production Examples in Examples.

[Step 10]

This step is a step of converting a hydroxy group in compound (15) into a leaving group to produce compound (16). When the LG is a chlorine atom or a bromine atom, the step is a step of halogenating compound (15) in the presence of triphenylphosphine using tetrachloromethane or tetrabromomethane to produce compound (16). The solvent to be used in the reaction is not particularly limited as long as the solvent can dissolve starting materials to some extent and does not inhibit the reaction. For example, an ether-type solvent such as tetrahydrofuran; an amide-type solvent such as N,N-dimethylformamide and N-methylpyrrolidinone; a halogen-containing solvent such as dichloromethane and chloroform; or a mixed solvent comprising any two or more of the aforementioned solvents can be used. Tetrachloromethane or tetrabromomethane can also be used as the solvent. Triphenylphosphine can be used in an amount ranging from 1 to 5 equivalents relative to the amount of compound (15). Tetrachloromethane or tetrabromomethane can be used in an amount ranging from 1 equivalent to a solvent amount relative to the amount of compound (15). The reaction temperature ranges from 0° C. to a reflux temperature, the reaction time ranges from 5 minutes to 48 hours.

Compound (16) can also be produced via compound (15) by the method described in any one of alternative steps (3), (4) and (5) mentioned below.

Alternative step (3): Compound (15) can be converted into compound (16) by reacting under acidic conditions. The solvent to be used in the reaction is not particularly limited, as long as the solvent can dissolve the starting material to some extent and does not inhibit the reaction. For example, an ether-type solvent such as diethyl ether, water, ethyl acetate or a mixed solvent comprising any two or more of the aforementioned solvents can be used. In the reaction, a phase transfer catalyst such as tetrabutylammonium bromide can be added in an amount ranging from a catalytic amount to 2 equivalents relative to the amount of compound (15). As the acid, hydrochloric acid, hydrobromic acid and the like can be used. For the purpose of achieving good yield, sulfuric acid can also be added. The reaction temperature ranges from 0° C. to room temperature, and the reaction time ranges from 5 minutes to 48 hours.

Alternative step (4): Compound (16) can be produced by reacting compound (15) with thionyl chloride. The solvent to be used in the reaction is not particularly limited, as long as the solvent can dissolve the starting material to some extent and does not inhibit the reaction. For example, an aromatic hydrocarbon-type solvent such as benzene and toluene; a nitrile-type solvent such as acetonitrile; a halogen-containing solvent such as chloroform and dichloromethane; or a mixed solvent comprising any two or more of the aforementioned solvents can be used, and thionyl chloride can also be used as the solvent. For the purpose of achieving good yield, a catalytic amount of pyridine can be added. Thionyl chloride can be used in an amount ranging from 1 equivalent to a solvent amount relative to the amount of compound (15). The reaction temperature ranges from 0° C. to a reflux temperature, and the reaction time ranges from 5 minutes to 48 hours.

Alternative step (5): Compound (16) can be produced by reacting compound (15) with a phosphorus halide. The solvent to be used in the reaction is not particularly limited as long as the solvent can dissolve starting materials to some extent and does not inhibit the reaction. For example, an ether-type solvent such as diethyl ether; a nitrile-type solvent such as acetonitrile; a halogen-containing solvent such as dichloromethane and chloroform; or a mixed solvent comprising any two or more of the aforementioned solvents can be used. As the phosphorus halide, phosphorus oxychloride, phosphorus trichloride, phosphorus tribromide and the like can be used. The phosphorus halide can be used in an amount of 0.33 to 3 equivalents relative to the amount of compound (15). The reaction temperature ranges from 0° C. to a reflux temperature, and the reaction time ranges from 5 minutes to 48 hours.

When the LG is a sulfonic acid ester such as a methanesulfonyloxy group, a trifluoromethanesulfonyloxy group or a p-toluenesulfonyloxy group, the step is a step of reacting compound (15) with a sulfonic acid chloride or a sulfonic acid anhydride under basic conditions to produce compound (16). The solvent to be used in the reaction is not particularly limited as long as the solvent can dissolve starting materials to some extent and does not inhibit the reaction. For example, an ether-type solvent such as 1,4-dioxane and tetrahydrofuran; an aromatic hydrocarbon-type solvent such as benzene and toluene; an amide-type solvent such as N,N-dimethylformamide and N-methylpyrolidinone; a sulfoxide-type solvent such as dimethyl sulfoxide; a halogen-containing solvent such as dichloromethane; or a mixed solvent comprising any two or more of the aforementioned solvents can be used. As the base, triethylamine, N,N-diisopropylethylamine and the like can be used. As the sulfonic acid chloride, methanesulfonyl chloride, trifluoromethanesulfonyl chloride, p-toluenesulfonyl chloride and the like can be used. As the sulfonic acid anhydride, methanesulfonic acid anhydride, trifluoromethanesulfonic acid anhydride, p-toluenesulfonic acid anhydride and the like can be used. The base can be used in an amount of 1 to 5 equivalents relative to the amount of compound (15). The sulfonic acid chloride or the sulfonic acid anhydride can be used in an amount of 1 to 3 equivalents relative to the amount of compound (15). The reaction temperature ranges from 0° C. to room temperature, and the reaction time ranges from 5 minutes to 48 hours.

[Step 11]

This step is a step of reacting compound (16) with compound (17) or a salt thereof in the presence of a base to produce compound (19). The solvent to be used in the reaction is not particularly limited as long as the solvent can dissolve starting materials to some extent and does not inhibit the reaction. For example, an ether-type solvent such as tetrahydrofuran and diethyl ether; an aromatic hydrocarbon-type solvent such as benzene and toluene; an amide-type solvent such as N,N-dimethylformamide and N-methylpyrrolidinone; an alcohol-type solvent such as methanol and ethanol; a halogen-containing solvent such as dichloromethane and chloroform; a nitrile-type solvent such as acetonitrile and propionitrile; a sulfoxide-type solvent such as dimethyl sulfoxide; a basic solvent such as pyridine; an ester-type solvent such as ethyl acetate; or a mixed solvent comprising any two or more of the aforementioned solvents can be used. As the base to be used in the reaction, triethylamine, N,N-diisopropylethylamine, DBU, sodium hydrogen carbonate, potassium carbonate and the like can be used, and compound (17) itself can also be used. Compound (17) can be used in an amount of 1 to 10 equivalents, preferably 1 to 2 equivalents, relative to the amount of compound (16). The base can be used in an amount of 1 equivalent to an excess amount relative to the amount of compound (16). The reaction temperature ranges from 0° C. to a reflux temperature, and the reaction time ranges from 10 minutes to 48 hours.

[Step 12]

This step is a step of oxidizing compound (15) to produce compound (18). The solvent to be used in the reaction is not particularly limited as long as the solvent can dissolve starting materials to some extent and does not inhibit the reaction, and a halogen-containing solvent such as dichloromethane and chloroform; an aromatic hydrocarbon-type solvent such as benzene and toluene; an amide-type solvent such as N,N-dimethylformamide and N-methylpyrrolidinone; an ester-type solvent such as ethyl acetate; a nitrile-type solvent such as acetonitrile and propionitrile; a sulfoxide-type solvent such as dimethyl sulfoxide; acetone; a mixed solvent comprising any two or more of the aforementioned solvents, or the like can be used. As the oxidizing agent to be used in the reaction, manganese dioxide, pyridinium chlorochromate, pyridinium dichromate, a dimethyl sulfoxide-activating agent, tetrapropylammonium perruthenate, dichlorotris (triphenylphosphine)ruthenium (II), 1,1,1-tris(acetyloxy)-1, 1-dihydro-1,2-benziodoxol-3-(1H)-one (Dess-Martin periodinane), 1-hydroxy-1,2-benziodoxol-3(1H)-one-1-oxide (IBX) and the like can be used. The oxidizing agent can be used in an amount ranging from a catalytic amount to an excess amount relative to the amount of compound (15). When the oxidization is carried out using a dimethyl sulfoxide-activating agent, an acid anhydride such as acetic anhydride and trifluoroacetic anhydride; an acid chloride such as oxalyl chloride and thionyl chloride; chlorine, N-chlorosuccinimide; and the like can be used as the activating agent. Dimethyl sulfoxide can be used in an amount of 1 to 20 equivalents relative to the amount of activating agent. When tetrapropylammonium perruthenate or dichlorotris(triphenylphosphine)ruthenium (II) is used in a catalytic amount, it is possible to use an oxidizing agent such as N-methylmorpholine-N-oxide or bis(trimethylsilyl)peroxide simultaneously. The reaction temperature varies depending on the types of the oxidizing agent to be used and ranges from −78° C. to a reflux temperature, and the reaction time ranges from 10 minutes to 96 hours.

[Step 13]

This step is a step of reacting compound (18) with compound (17) or a salt thereof to perform reductive amination, thereby producing compound (19). Compound (19) can be produced in the similar manner as in step 4.

[Step 14]

This step is a step of removing the protective group for the amino group in compound (19) to produce compound (3). The conditions for the deprotection vary depending on the types of the protective group for the amino group. For example, when a benzyl-type group such as a benzyl group and a benzhydryl group, a benzyloxycarbonyl (Cbz or Z) group or the like is used as the protective group for the amino group, the conditions for the deprotection are those conditions employed in a catalytic hydrogenation method that is the same as that employed in Alternative step (2) in step 6 or those conditions generally employed for the removal of a benzyl group, and compound (3) can be produced employing the conditions. When a tert-butyloxycarbonyl (Boc) group or the like is used as the protective group for the amino group, the conditions for the deprotection to be employed are acidic conditions using hydrochloric acid, trifluoroacetic acid or the like, conditions using a Lewis acid such as aluminum chloride and zinc bromide, conditions using tetrabutylammonium fluoride or the like, conditions using a silyl compound such as trimethyl silyl iodide, trimethyl silyl chloride and tetrachlorosilane, and the like.

[Production Method 4] Method for Producing Compound (4)

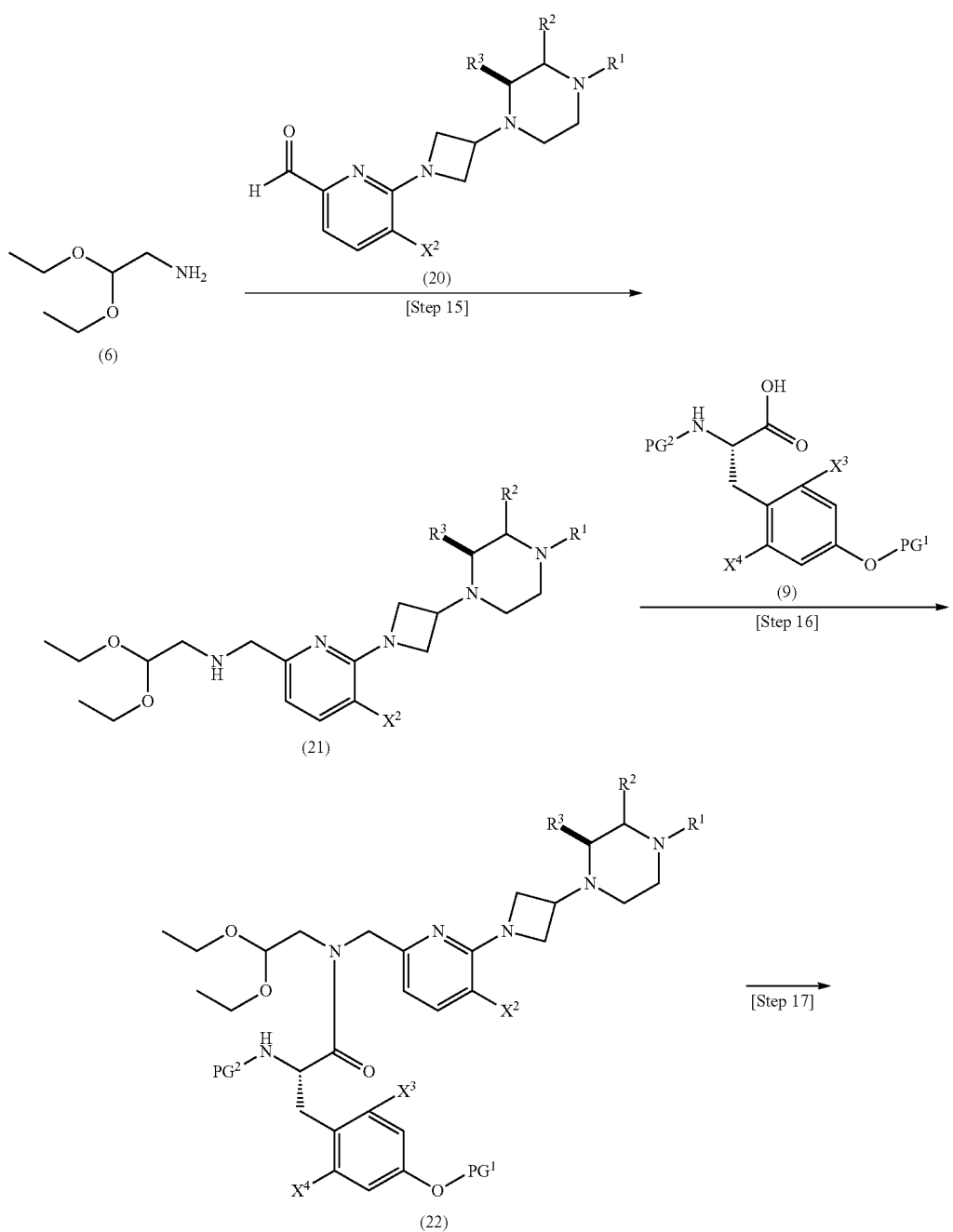

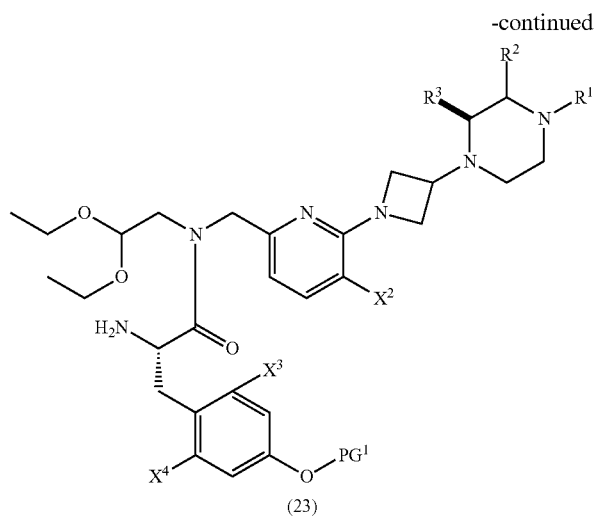

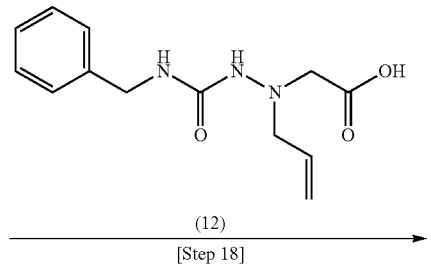

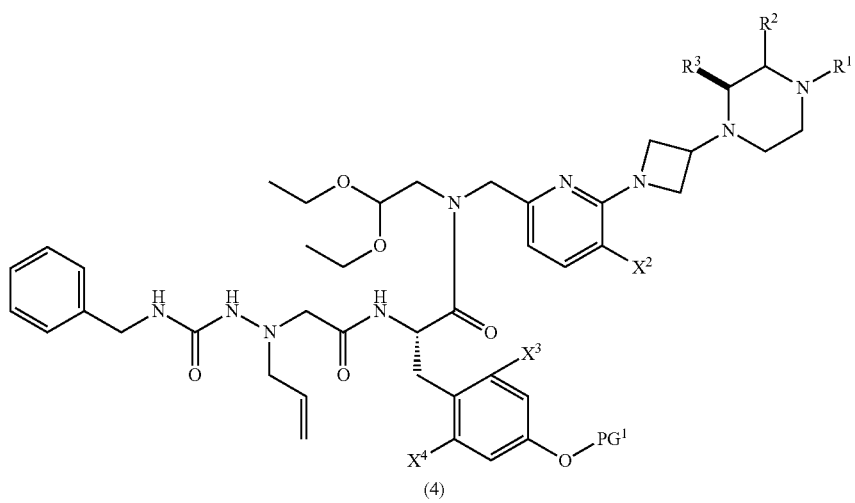

wherein $R^1$, $R^2$, $R^3$, $X^2$, $X^3$, $X^4$, $PG^1$ and $PG^2$ are as defined in the definition.

With respect to compound (20), a commercially available compound can be used without any modification. Alternatively, the compound can be produced from a commercially available compound by a known method. The compound can also be produced employing a method described in Production Examples in Examples, Production Method 5 or the like.

With respect to each of compound (6), compound (9) and compound (12), a commercially available compound can be used without any modification. Alternatively, the compounds can be produced respectively from commercially available products by a known method.

[Step 15]

This step is a step of reacting compound (20) with compound (6) or a salt thereof to perform reductive amination, thereby producing compound (21). Compound (21) can be produced in the similar manner as in step 4.

[Step 16]

This step is a step of reacting compound (21) or a salt thereof with compound (9) or a salt thereof in the presence of a condensing agent to produce compound (22). Compound (22) can be produced in the similar manner as in step 5.

[Step 17]

This step is a step of removing the protective group for the amino group in compound (22) to produce compound (23). Compound (23) can be produced in the similar manner as in step 6.

[Step 18]

This step is a step of reacting compound (23) or a salt thereof with compound (12) or a salt thereof in the presence of a condensing agent to produce compound (4). Compound (4) can be produced in the similar manner as in step 5.

[Production Method 5] Method for Producing Compound (20)

also be produced employing a method described in Production Examples in Examples, Production Method 3 or the like.

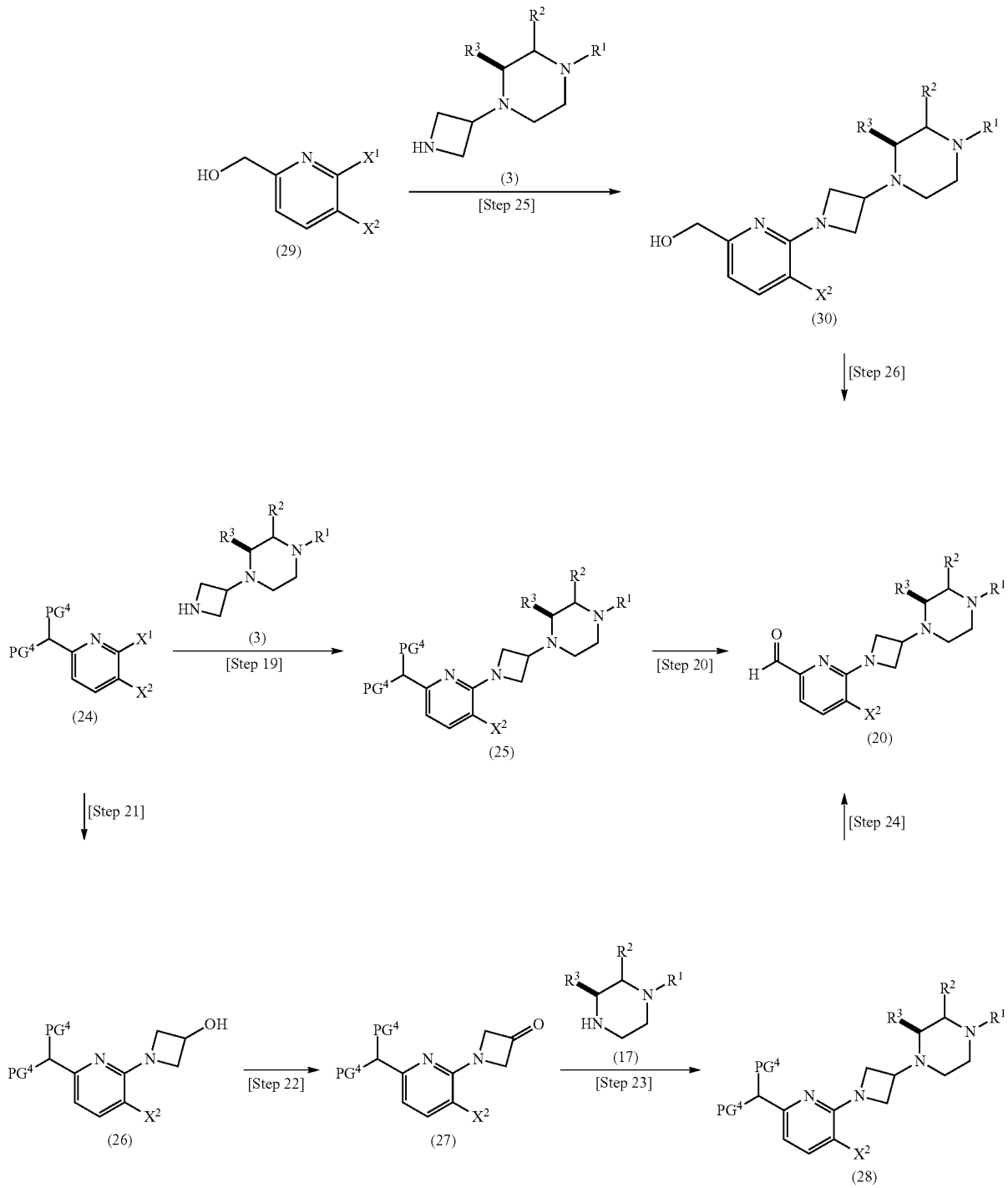

wherein $R^1$, $R^2$, $R^3$, $X^1$ and $X^2$ are as defined in the definition; and $PG^4$ is a protective group for an aldehyde.

With respect to compound (3), a commercially available compound can be used without any modification. Alternatively, the compound can be produced from a commercially available compound by a known method. The compound can With respect to each of compound (17), compound (24) and compound (29), a commercially available compound may be used without any modification, or the compound may be produced from a commercially available compound by a known method. Each of the compounds can be produced by a method described in Production Examples in Examples.

[Step 19]

This step is a step of reacting compound (24) with compound (3) or a salt thereof to produce compound (25). Compound (25) can be produced in the similar manner as in step 1.

[Step 20]

This step is a step of removing the protective group for the aldehyde group in compound (25) to produce compound (20). The conditions for the deprotection vary depending on the types of the protective group for the aldehyde group. For example, when an acetal-type protective group is used as the protective group for the aldehyde group, compound (20) can be produced by the conditions for the deprotection that are those generally employed for the removal of an acetal, such as conditions employed in a method for reacting under acidic conditions using formic acid, p-toluenesulfonic acid or the like.

[Step 21]

This step is a step of reacting compound (24) with azetidin-3-ol or a salt thereof to produce compound (26). Compound (26) can be produced in the similar manner as in step 1.

[Step 22]

This step is a step of oxidizing compound (26) to produce compound (27). Compound (27) can be produced in the similar manner as in step 12.

[Step 23]

This step is a step of reacting compound (27) with compound (17) to perform reductive amination, thereby producing compound (28). Compound (28) can be produced in the similar manner as in step 4.

[Step 24]

This step is a step of removing the protective group for the aldehyde group in compound (28) to produce compound (20). Compound (20) can be produced in the similar manner as in step 20.

[Step 25]

This step is a step of reacting compound (29) with compound (3) or a salt thereof to produce compound (30). Compound (30) can be produced in the similar manner as in step 1.

[Step 26]

This step is a step of oxidizing compound (30) to produce compound (20). Compound (20) can be produced in the similar manner as in step 12.

[Production Method 6] Method for Producing Compound (5)

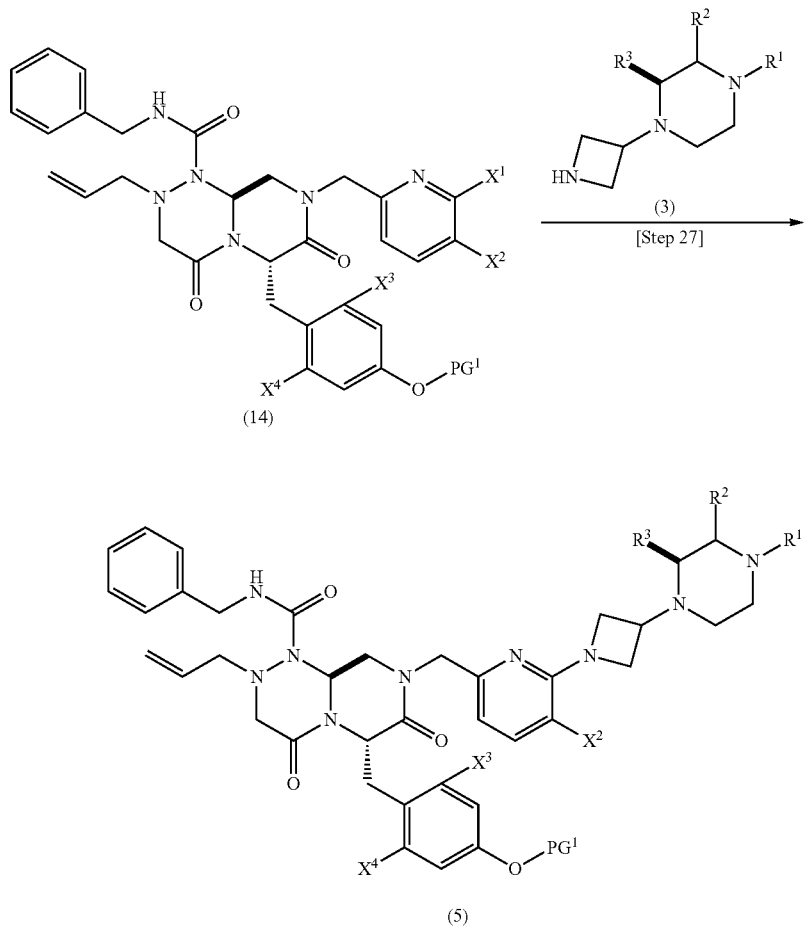

wherein $R^1$, $R^2$, $R^3$, $X^1$, $X^2$, $X^3$, $X^4$ and $PG^1$ are as defined in the definition.

With respect to compound (3), a commercially available compound can be used without any modification. Alternatively, the compound can be produced from a commercially available compound by a known method. The compound can also be produced employing a method described in Production Examples in Examples, Production Method 3 or the like.

Compound (14) can be produced from a commercially available compound by a known method, and can also be produced employing a method described in Production Examples in Examples, Production Method 2 or the like.

[Step 27]
This step is a step of reacting compound (14) with compound (3) or a salt thereof to produce compound (5). Compound (5) can be produced in the similar manner as in step 1.

[Production Method 7] Method for Producing Compound (36)

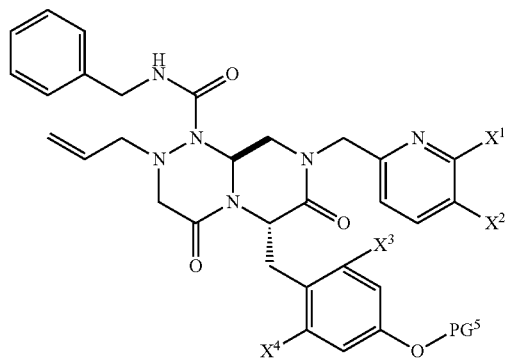

(31)

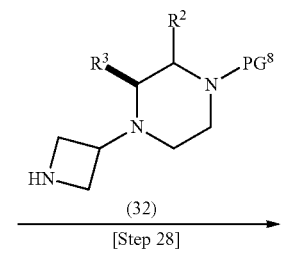

(32)

[Step 28]

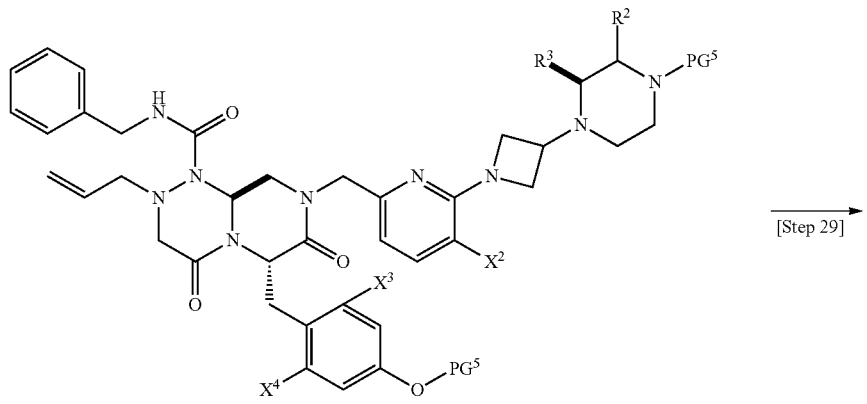

(33)

[Step 29]

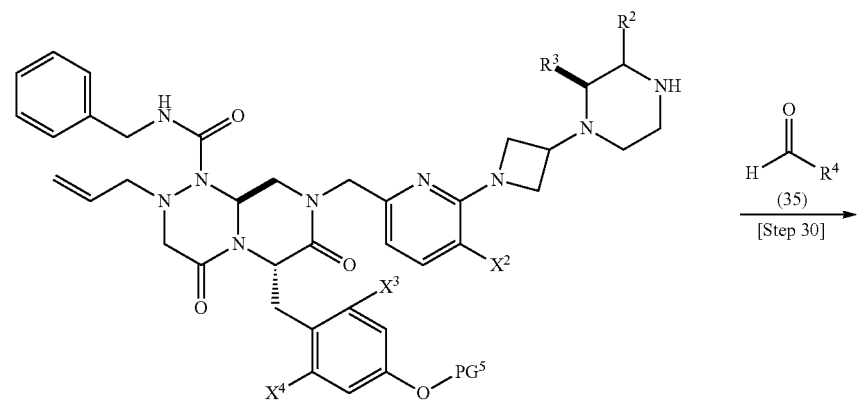

(34)

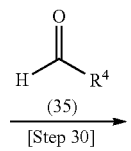

(35)

[Step 30]

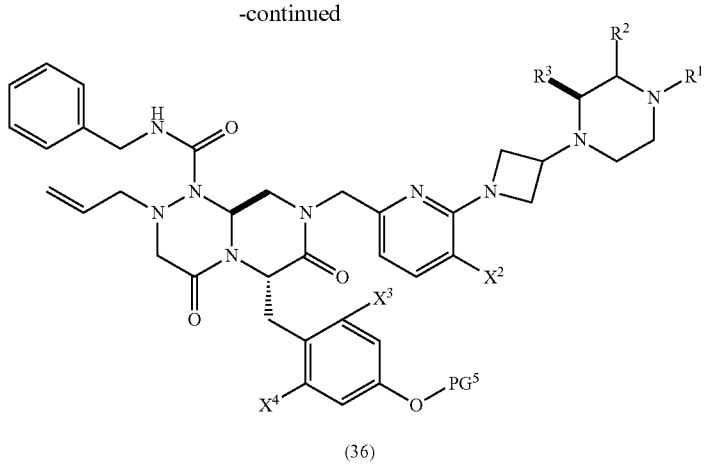

(36)

wherein $R^1$, $R^2$, $R^3$, $X^1$, $X^2$, $X^3$ and $X^4$ are as defined in the definition; $PG^5$ is a hydrogen atom or a protective group for a hydrogen atom or a phenolic hydroxy group; $PG^6$ is a protective group for an amino group; and $R^4$ is a hydrogen atom or a $C_{1-5}$ alkyl group, where $R^1$ is —$CH_2R^4$.

Compound (31) can be produced from a commercially available compound by a known method, and can also be produced employing a method described in Production Examples in Examples, Production Method 2 or the like.

With respect to compound (32), a commercially available compound can be used without any modification. Alternatively, the compound can be produced from a commercially available compound by a known method. Alternatively, the compound can also be produced employing a method described in Production Examples in Examples, Production Method 3 or the like.

With respect to compound (35), a commercially available compound can be used without any modification. Alternatively, the compound can be produced from a commercially available compound by a known method.

[Step 28]
This step is a step of reacting compound (31) with compound (32) or a salt thereof to produce compound (33). Compound (33) can be produced in the similar manner as in step 1.

[Step 29]
This step is a step of removing the protective group $PG^6$ for the amino group in compound (33) to produce compound (34). The conditions for the deprotection vary depending on the types of the protective group for the amino group. For example, when a tert-butyloxycarbonyl group or the like is used as the protective group for the amino group, compound (34) can be produced by a similar condition for the deprotection in step 14.

[Step 30]
This step is a step of reacting compound (34) or a salt thereof with compound (35) to perform reductive amination, thereby producing compound (36). Compound (36) can be produced in the similar manner as in step 4.

[Production Method 8] Method for Producing Compound (1B)

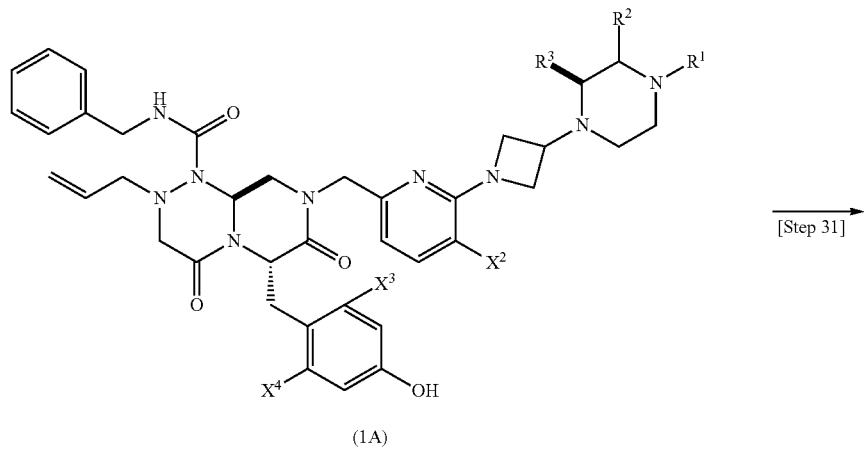

(1A)

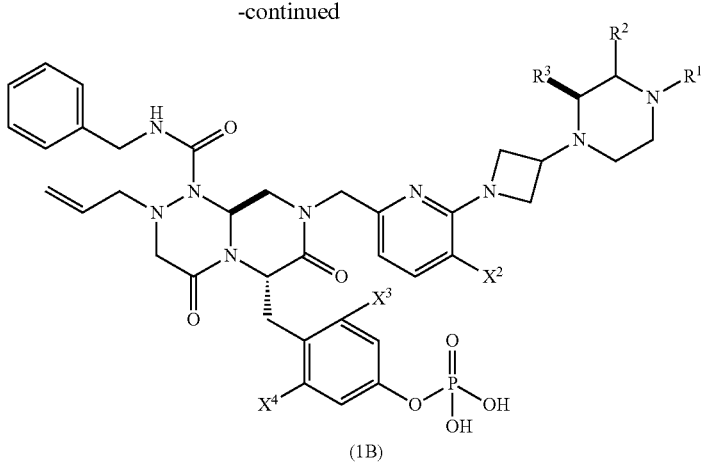

(1B)

wherein $R^1$, $R^2$, $R^3$, $X^2$, $X^3$ and $X^4$ are as defined in the definition.

The method for producing compound (1B) which is a compound represented by formula (1) wherein $X^5$ is $-P(=O)(OH)_2$ is mentioned below.

[Step 31]

This step is a step of reacting a phenolic hydroxy group in compound (1A) with a phosphate esterifying agent such as phosphorus oxychloride, then carrying out a post treatment of the resultant product with an aqueous sodium hydroxide solution or the like, and then neutralizing the treated product, thereby producing compound (1B). The reaction temperature is preferably 0° C. or lower, and the reaction time is preferably 10 minutes to 3 hours. The amount of the phosphate esterifying agent is preferably 1 to 5 equivalent relative to the amount of compound (1A).

After the completion of each method or each step, a desired compound in each step can be collected from a reaction mixture according to a conventional method.

The typical methods for producing compound (1) are as mentioned above. Each of the starting material compounds and reagents used in the production of compound (1) may have a form of a salt or a solvate such as a hydrate, and can be varied depending on the types of the starting materials, solvents used and the like, and is not particularly limited as long as it does not inhibit the reaction. The solvents used can also be varied depending on the types of the starting materials, reagents and the like, and are not particularly limited as long as they do not inhibit the reaction and can dissolve the starting materials to some extent. When compound (1) is produced in a free form, the free form can be converted into a salt or a solvate into which compound (1) can be formed by a conventional method.

When compound (1) is produced in the form of a salt or a solvate, the salt or the solvate can be converted into a free form of compound (1) by a conventional method.

Various isomers (e.g., a geometrical isomer, an optical isomer, a rotamer, a stereoisomer, a tautomer) of compound (1) or an intermediate thereof can be purified and isolated by a common separating methods, such as a crystallization method, a diastereomeric salt method, an enzymatic resolution method, various types of chromatography (e.g., thin-layer chromatography, column chromatography, gas chromatography).

If required, compound (1) or a pharmaceutically acceptable salt thereof can be mixed with a pharmaceutically acceptable additive to prepare a pharmaceutical composition. Examples of the dosage form of the pharmaceutical composition include oral preparations (e.g., tablets, granules, a powder, a capsule, a syrup), injectable preparations (e.g., for intravenous administration, intramuscular administration, subcutaneous administration, intraperitoneal administration) and preparations for external applications (e.g., a transdermal preparation, (an ointment, an adhesive skin patch, etc.), an eye drop, a nose drop, a suppository).

A solid preparation such as tablets, a capsule, granules and a powder can generally contain 0.001 to 99.5 mass %, preferably 0.001 to 90 mass % of compound (1) or a pharmaceutically acceptable salt thereof.

When a solid preparation for oral administration is to be produced, an excipient, a binder, a disintegrating agent, a lubricant agent, a coloring agent and the like can be added as required to compound (1) or a pharmaceutically acceptable salt thereof to produce tablets, granules, a powder, a capsule or the like by a conventional method. If necessary, the tablets, the granules, the powder, the capsule or the like may be subjected to film coating.

Examples of the excipient include lactose, corn starch and crystalline cellulose, examples of the binder include hydroxypropyl cellulose and hydroxypropylmethyl cellulose, and examples of the disintegrating agent include carboxymethyl cellulose calcium and croscarmellose sodium.

Examples of the lubricant agent include magnesium stearate and calcium stearate, and examples of the coloring agent include iron sesquioxide, yellow iron sesquioxide and titanium oxide.

Examples of a film coating agent include hydroxypropyl cellulose, hydroxypropylmethyl cellulose and methyl cellulose.

Examples of the above-mentioned additives are not limited to the substances mentioned above.

When an injectable preparation (e.g., for intravenous administration, intramuscular administration, subcutaneous administration, intraperitoneal administration) is to be produced, the injectable preparation can be produced by a conventional method by adding a pH modifier, a buffering agent, a suspending agent, a dissolution aid, an anti-oxidant agent, a preservative agent (an anti-septic agent), a tonicity agent and the like to compound (1) or a pharmaceutically acceptable salt thereof as required. The injectable preparation may be lyophilized to prepare a lyophilized preparation that can be dissolved immediately before use. The injectable preparation can be administered intravenously, subcutaneously, intramuscularly or the like.

Examples of the pH modifier and the buffering agent include an organic acid or an inorganic acid and/or a salt thereof, sodium hydroxide and meglumine, and examples of the suspending agent include methyl cellulose, polysorbate 80 and sodium carboxymethyl cellulose. Examples of the solubilization agent include polysorbate 80 and polyoxyethylene sorbitan monolaurate, examples of the antioxidative agent include ascorbic acid and α-tocopherol, examples of the preservative agent include methyl paraoxybenzoate and ethyl paraoxybenzoate, and examples of the tonicity agent include glucose, sodium chloride and mannitol. These components are not limited to the above-mentioned substances.

The injectable solution can generally contain compound (1) or a pharmaceutically acceptable salt thereof in an amount of 0.000001 to 99.5 mass %, preferably 0.000001 to 90 mass %.

When a preparation for external application is to be produced, the preparation can be produced by a conventional manner by adding a base raw material to compound (1) or a pharmaceutically acceptable salt thereof and, if necessary, further adding the above-mentioned emulsifying agent, preservative agent, pH modifier, coloring agent and the like to the resultant mixture, thereby producing a transdermal preparation (e.g., an ointment, an adhesive skin patch), an eye drop, a nose drop, a suppository and the like.

As the base raw material to be used, various raw materials which have been used conventionally in drugs, quasi drugs, cosmetics and the like. Examples of the base raw material include a raw material such as an animal/vegetable oil, a mineral oil, an ester oil, a wax, a higher alcohol and purified water.

The preparation for external application can generally contain compound (1) or a pharmaceutically acceptable salt thereof in an amount of 0.000001 to 99.5 mass %, preferably 0.000001 to 90 mass %.

The dose of the medicine according to the present invention is generally varied depending on the bodily conditions, ages, sexes, body weights and the like, and may be an enough amount to develop a desired effect. For example, in the case of a human adult, about 0.1 to 5000 mg (preferably 0.5 to 1000 mg) per day is administered one time daily or every several days or in 2 to 6 divided doses daily.

The compound according to the present invention includes an isotopically labeled form of compound (1). The isotopically labeled form is substantially the same as compound (1), except that at least one atom is substituted by an atom having a different atomic mass or a different atomic mass number from that usually found in nature. Examples of the isotope that can be incorporated into compound (1) include an isotope of hydrogen, an isotope of carbon, an isotope of nitrogen, an isotope of oxygen, an isotope of phosphorus, an isotope of fluorine, an isotope of iodine or an isotope of chlorine, such as $^2$H, $^3$H, $^{11}$C, $^{14}$C, $^{18}$F, $^{35}$S, $^{123}$I and $^{125}$I.

Compound (1) containing the above-mentioned isotope and/or another isotope or a pharmaceutically acceptable derivative thereof (e.g., a salt) is included within the scope of the compound according to the present invention. The isotopically labeled compound according to the present invention, e.g., a compound in which a radioactive isotope such as $^3$H and $^{14}$C is incorporated, is useful for a medicine or substrate tissue distribution assay. Isotopes $^3$H and $^{14}$C are considered as being useful because of the easiness of preparation and detection thereof. Isotopes $^{11}$C and $^{18}$F are considered as being useful for PET (positron emission tomography), an isotope $^{125}$I is considered as being useful for SPECT (single photon emission computed tomography), and all of the isotopes are useful for brain imaging. The substitution by a heavier isotope such as $^2$H provides a certain therapeutic advantage such as the increase in the in vivo half-life, the reduction in a necessary dose amount or the like due to higher metabolic stability, and is therefore considered as being useful in certain situations. An isotopically labeled form of compound (1) can be prepared constantly by carrying out the procedure disclosed in Examples mentioned below using a readily applicable isotopically labeled reagent in place of an isotope-unlabeled reagent.

Compound (1) can be used as a chemical probe for capturing a target protein of a physiologically active low-molecular-weight compound. That is, compound (1) can be converted into an affinity chromatography probe, a photoaffinity chromatography probe or the like by introducing a labeling group, a linker or the like into a moiety of compound (1) which is different from a structural moiety essential to the development of the activity of the compound by a technique disclosed in J. Mass Spectrum. Soc. Jpn. Vol. 51, No. 5 2003, p492-498, International Publication No. 2007/139149 or the like.

Examples of the labeling group, the linker or the like to be used in the chemical probe include groups mentioned in the groups (1) to (5) below:
(1) a protein labeling group such as a photoaffinity labeling group (e.g., a benzoyl group, benzophenone group, an azide group, a carbonylazide group, a diaziridine group, an enone group, a diazo group and a nitro group) and a chemical affinity group (e.g., a ketone group in which an alpha carbon atom is substituted by a halogen atom, a carbamoyl group, an ester group, an alkylthio group, a Michael acceptor such as an α,β-unsaturated ketone group and an α,β-unsaturated ester group, and an oxirane group);
(2) a cleavable linker such as —S—S—, —O—Si—O—, a monosaccharide group (e.g., a glucose group, a galactose group) or a disaccharide group (e.g., a lactose group), and an oligopeptide linker capable of being cleaved by an enzymatic reaction;
(3) a fishing tag group such as biotin and 3-(4,4-difluoro-5, 7-dimethyl-4H-3a,4a-diaza-4-bora-s-indacen-3-yl) propionyl group;
(4) a radioactive labeling group such as $^{125}$I, $^{32}$P, $^3$H and $^{14}$C; a fluorescent labeling group such as fluorescein, rhodamine, dansyl, umbelliferone, a 7-nitrofurazanyl, 3-(4,4-difluoro-5, 7-dimethyl-4H-3a,4a-diaza-4-bora-s-indacen-3-yl) propionyl group; a chemical luminescent group such as luciferine and luminol; a marker capable of detecting a heavy metal ion such as a lanthanoid metal ion and a radium ion;
(5) a group capable of being bound to a solid carrier such as a glass bead, a glass bed, a microtiter plate, an agarose bead, an agarose bed, a polystyrene bead, a polystyrene bed, a nylon bead and a nylon bed; and others.

A probe prepared by introducing a labeling group or the like selected from the group consisting of the above-mentioned items (1) to (5) into compound (1) by a method described in the above-mentioned publications or the like can be used as a chemical probe for identifying a labeling protein that is useful for the searching for a novel drug discovery target and the like.

EXAMPLES

The compound according to the present invention can be produced by the methods described in Production Examples and Examples as mentioned below. However, these examples are only for illustrative purposes and the compound according to the present invention is not limited to the specific examples mentioned below in any way.

In Production Examples and Examples, unless specifically mentioned otherwise, the silica gel for purification by using silica gel column chromatography was YMC GEL SILICA (YMC Co., Ltd, catalog code: SL06I52W), the silica gel for purification by using NH silica gel column chromatography was NH silica gel (Fuji Silysia Chemical LTD., catalog code: DM2035), the silica gel for purification by using ODS silica gel column chromatography was YAMAZEN GEL ODS-SM (YAMAZEN Corporation, catalog codes: W113, W116, etc.), the TLC plate for purification by using silica gel thin-layer chromatography was TLC Silica gel 60F$_{254}$ (Merck KGaA, catalog code: 1.05715.0001), and the TLC plate for purification by using NH silica gel thin-layer chromatography was NH SILICA GEL TLC plate (Fuji Silysia Chemical LTD., catalog code: T050908).

The abbreviations used herein are as follows:
NMP: N-methylpyrrolidinone
THF: tetrahydrofuran
HATU: O-(7-azabenzotriazol-1-yl)-N,N,N',N'-tetramethyluronium hexafluorophosphate
HBTU: O-(benzotriazol-1-yl)-N,N,N',N'-tetramethyluronium hexafluorophosphate
TFA: trifluoroacetic acid
DMF: N,N-dimethylformamide
DBU: 1,8-diazabicyclo[5.4.0]undec-7-ene Example 1

(6S,9aS)-N-Benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

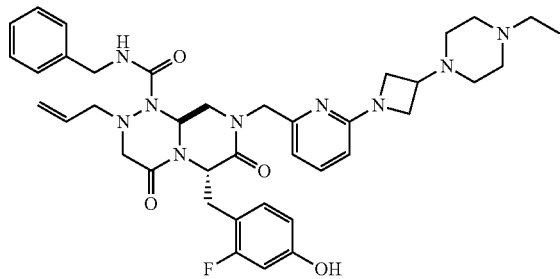

To a mixed solution of (6S,9aS)-N-benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (397 mg, 0.689 mmol) described in Production Example 1-1-6 and NMP (10 mL) was added a mixture (1.16 g) of 1-(azetidin-3-yl)-4-ethylpiperazine and benzylbenzene described in Production Example 1-3-2 at room temperature. The resultant mixture was irradiated with a microwave at 140° C. for 12 hours. The reaction mixture was cooled to room temperature, water was then added thereto, then the resultant solution was extracted with ethyl acetate, and an organic layer was washed with saturated brine. The organic layer was dried over anhydrous magnesium sulfate and then filtrated. The solvent was evaporated under a reduced pressure, and the resultant residue was purified by silica gel column chromatography (methanol) and then further purified by NH silica gel column chromatography (ethyl acetate:methanol=20:1) to give the title compound (402 mg, yield: 80%).

$^1$H-NMR Spectrum (400 MHz, CDCl$_3$) δ(ppm): 1.00 (3H, t, J=6.8 Hz), 2.10-2.65 (10H, m), 3.10-3.21 (2H, m), 3.41-3.74 (8H, m), 3.84-3.89 (1H, m), 3.95-4.05 (2H, m), 4.17-4.23 (2H, m), 4.51 (1H, dd, J=6.8 Hz, 15.6 Hz), 4.95 (1H, d, J=13.6 Hz), 5.20-5.30 (3H, m), 5.50-5.60 (1H, m), 5.70-5.80 (1H, m), 5.82-5.87 (1H, m), 6.24 (1H, d, J=8.0 Hz), 6.41 (1H, dd, J=2.0 Hz, 11.2 Hz), 6.47 (1H, dd, J=8.8 Hz, 8.8 Hz), 6.69 (1H, d, J=7.2 Hz), 6.80-6.86 (1H, m), 7.20-7.31 (3H, m), 7.35-7.46 (3H, m).

ESI-MS (m/z): 726.57 [M+H]$^+$.

Production Example 1-1-1

(2,2-Diethoxyethyl)((6-fluoropyridin-2-yl)methyl)amine

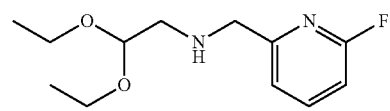 [SMILES: CCOC(CNCc1cccc(F)n1)OCC]

To a mixed solution of a commercially available product of 2,2-diethoxyethan-1-amine (926 μL, 6.39 mmol), THF (10.0 mL) and acetic acid (1.00 mL) was added a commercially available product of 6-fluoropyridine-2-carbaldehyde (800 mg, 6.39 mmol) at room temperature. The resultant mixture was stirred at room temperature for 25 minutes. Subsequently, sodium triacetoxyborohydride (2.71 g, 12.8 mmol) was added to the reaction mixture at room temperature and then stirred for 1 hour and 10 minutes. To the reaction mixture was added sodium hydrogen carbonate and water to terminate the reaction. The resultant solution was extracted with ethyl acetate. An organic layer was dried over anhydrous magnesium sulfate and then filtrated. The solvent was evaporated under a reduced pressure, and the resultant residue was purified by NH silica gel column chromatography (heptane:ethyl acetate=1:1), and was then further purified by silica gel column chromatography (ethyl acetate:methanol=20:1) to give the title compound (1.14 g, yield: 74%).

$^1$H-NMR Spectrum (400 MHz, CDCl$_3$) δ(ppm): 1.22 (6H, t, J=7.2 Hz), 2.76 (2H, d, J=5.5 Hz), 3.50-3.61 (21, m), 3.65-3.76 (2H, m), 3.89 (2H, s), 4.64 (1H, t, J=5.5 Hz), 6.80 (1H, dd, J=2.8 Hz, 8.2 Hz), 7.22 (1H, dd, J=2.4 Hz, 7.3 Hz), 7.74 (1H, q, J=7.9 Hz).

Production Example 1-1-2

9H-Fluoren-9-ylmethyl N-((1S)-2-(4-(benzyloxy)-2-fluorophenyl)-1-(2,2-diethoxyethyl)((6-fluoropyridin-2-yl)methyl)carbamoyl)ethyl)carbamate

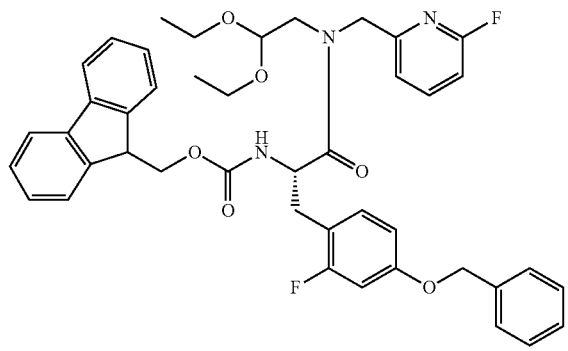 [SMILES: CCOC(CN(Cc1cccc(F)n1)C(=O)[C@H](Cc1ccc(OCc2ccccc2)cc1F)NC(=O)OCC1c2ccccc2-c2ccccc21)OCC]

To a mixed solution of (2,2-diethoxyethyl)((6-fluoropyridin-2-yl)methyl)amine (3.50 g, 14.4 mmol) described in Production Example 1-1-1 and dichloromethane (25 mL) were added (2S)-3-(4-(benzyloxy)-2-fluorophenyl)-2-(((9H-fluoren-9-ylmethoxy)carbonyl)amino)propanoic acid (7.76 g, 15.1 mmol) described in Production Example 1-2-7, N-methylmorpholine (2.06 mL, 18.7 mmol) and HATU (6.04 g, 15.8 mmol) at room temperature. The resultant mixture was stirred at room temperature for 13 hours. Sodium hydrogen carbonate and water were added to the reaction mixture, and the resultant solution was extracted with dichloromethane. An organic layer was dried over anhydrous magnesium sulfate and then filtrated. The solvent was evaporated under a reduced pressure to give a crude product (14.4 g) of the title compound. The product was used in the subsequent reaction without further purification.

ESI-MS (m/z): 758.50 [M+Na]$^+$.

Production Example 1-1-3

(2S)-2-Amino-3-(4-(benzyloxy)-2-fluorophenyl)-N-(2,2-diethoxyethyl)-N-((6-fluoropyridin-2-yl)methyl)propanamide

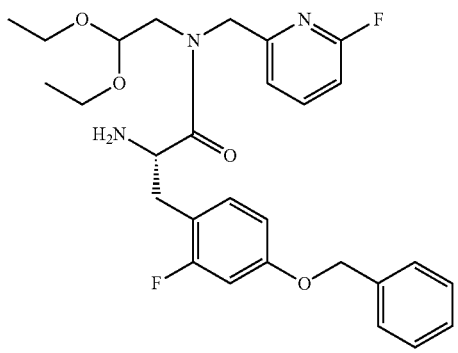 [SMILES: CCOC(CN(Cc1cccc(F)n1)C(=O)[C@@H](N)Cc1ccc(OCc2ccccc2)cc1F)OCC]

To a mixed solution of 9H-fluoren-9-ylmethyl N-((1S)-2-(4-(benzyloxy)-2-fluorophenyl)-1-((2,2-diethoxyethyl)((6-fluoropyridin-2-yl)methyl)carbamoyl)ethyl)carbamate described in Production Example 1-1-2 (14.4 g) and THF (30 mL) was added diethylamine (5.27 mL, 50.4 mmol) at room temperature. The resultant mixture was stirred at room temperature for 2 hours. The reaction mixture was concentrated under a reduced pressure, methanol, water and heptane were added to the residue, and the resultant mixture was partitioned. An aqueous layer was washed with heptane, and was then concentrated under a reduced pressure. Water was added to the residue, and the resultant solution was extracted with ethyl acetate. An organic layer was dried over anhydrous magnesium sulfate and then filtrated. The solvent was evaporated under a reduced pressure, and the resultant residue was purified by NH silica gel column chromatography (heptane: ethyl acetate=1:1, and then ethyl acetate) to give the title compound (6.87 g, yield: 93%).

ESI-MS (m/z): 514.32 [M+H]$^+$.

Production Example 1-1-4

(2S)-2-(2-(((Benzylcarbamoyl)amino)(prop-2-en-1-yl)amino)acetamido)-3-(4-(benzyloxy)-2-fluorophenyl)-N-(2,2-diethoxyethyl)-N-((6-fluoropyridin-2-yl)methyl)propanamide

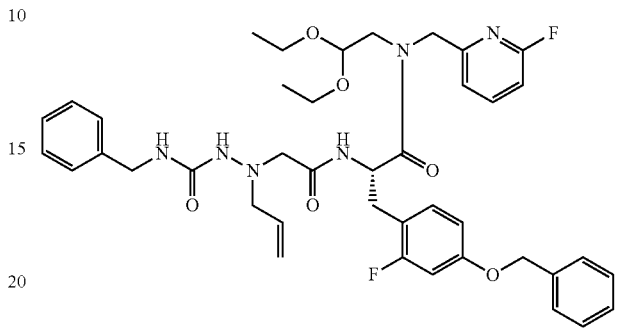

To a mixed solution of (2S)-2-amino-3-(4-(benzyloxy)-2-fluorophenyl)-N-(2,2-diethoxyethyl)-N-((6-fluoropyridin-2-yl)methyl)propanamide (4.87 g, 9.48 mmol) described in Production Example 1-1-3 and dichloromethane (100 mL) were added a known substance (WO2009148192) 2-(((benzylcarbamoyl)amino)(prop-2-en-1-yl)amino)acetic acid (2.62 g, 9.95 mmol), triethylamine (2.64 mL, 19.0 mmol) and HBTU (3.96 g, 10.4 mmol) at room temperature. The resultant mixture was stirred at room temperature for 1 hour. The reaction mixture was concentrated under a reduced pressure, and the resultant residue was purified by NH silica gel column chromatography (ethyl acetate and then ethyl acetate:methanol=30:1) to give the title compound (7.28 g, yield: quantitative).

ESI-MS (m/z): 759.43 [M+H]$^+$.

Production Example 1-1-5

(6S,9aS)-N-Benzyl-6-((4-(benzyloxy)-2-fluorophenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide

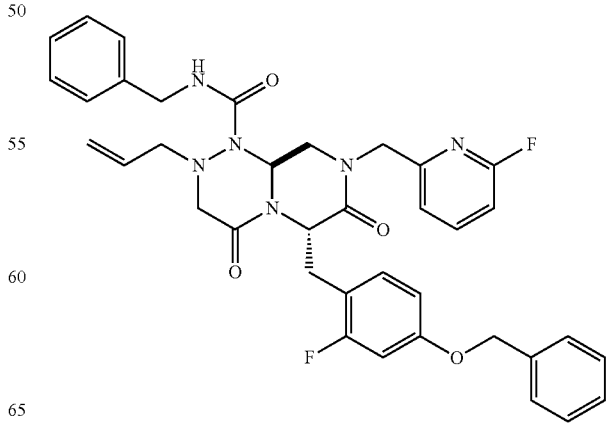

A mixed solution of (2S)-2-(2-(((benzylcarbamoyl)amino)(prop-2-en-1-yl)amino)acetamido)-3-(4-(benzyloxy)-2-fluorophenyl)-N-(2,2-diethoxyethyl)-N-((6-fluoropyridin-2-yl)methyl)propanamide (7.28 g, 9.48 mmol) described in Production Example 1-1-4 and formic acid (50 mL) was stirred at room temperature for 15 hours and 15 minutes. The reaction mixture was concentrated under a reduced pressure, an aqueous ammonia solution was added to the residue, and the resultant solution was extracted with ethyl acetate. An organic layer was dried over anhydrous magnesium sulfate and then filtrated. The solvent was evaporated under a reduced pressure, and the resultant residue was purified by NH silica gel column chromatography (heptane:ethyl acetate=1:1) to give the title compound (5.04 g, yield: 80%).

ESI-MS (m/z): 667.39 [M+H]$^+$.

Production Example 1-1-6

(6S,9aS)-N-Benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide

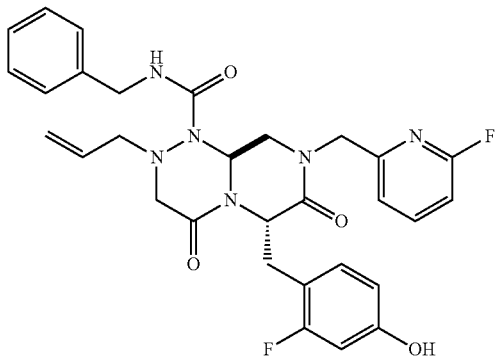

To a mixed solution of (6S,9aS)-N-benzyl-6-((4-(benzyloxy)-2-fluorophenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (5.04 g, 7.56 mmol) described in Production Example 1-1-5 and TFA (20 mL) was added thioanisole (3.55 mL, 30.2 mmol) at room temperature. The resultant mixture was stirred at room temperature for 13 hours and 50 minutes. The reaction mixture was concentrated under a reduced pressure, sodium hydrogen carbonate and water were added to the residue, and the resultant solution was extracted with ethyl acetate. An organic layer was dried over anhydrous magnesium sulfate and then filtrated. The solvent was evaporated under a reduced pressure, and the resultant residue was purified by NH silica gel column chromatography (ethyl acetate:methanol=20:1) to give the title compound (4.34 g, yield: quantitative).

ESI-MS (m/z): 577.31 [M+H]$^+$.

Production Example 1-2-1

Methyl(2S)-2-(((9H-fluoren-9-ylmethoxy)carbonyl)amino)-3-hydroxypropanoate

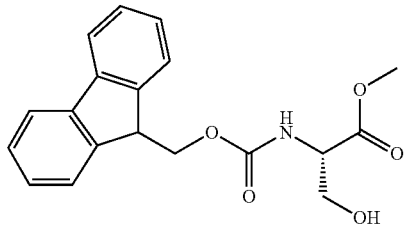 [SMILES: COC(=O)[C@H](CO)NC(=O)OCC1c2ccccc2-c2ccccc21]

To a mixed solution of a commercially available product of L-serine methyl ester hydrochloride (10.0 g, 64.3 mmol), 1,4-dioxane (15 mL) and water (90 mL) was added sodium hydrogen carbonate (10.8 g, 129 mmol) at room temperature. The resultant mixture was stirred at room temperature for 15 minutes. Subsequently, a solution of 2,5-dioxopyrrolidin-1-yl 9H-fluoren-9-ylmethylcarbonate (21.7 g 64.3 mmol) in 1,4-dioxane (60 mL) was added to the resultant solution at room temperature, and the resultant mixture was stirred at room temperature for 14 hours. Water was added to the reaction mixture, the resultant solution was extracted with ethyl acetate three times, and a combined organic layer was washed with water and saturated brine. An organic layer was dried over anhydrous magnesium sulfate and then filtrated. The solvent was evaporated under a reduced pressure, diethyl ether and heptane were added to the resultant residue, and a precipitate was collected by filtration to give the title compound (22.3 g, yield: quantitative).

$^1$H-NMR Spectrum (400 MHz, CDCl$_3$) δ(ppm): 2.00-2.15 (1H, m), 3.81 (3H, s), 3.89-4.07 (2H, m), 4.20-4.28 (1H, m), 4.39-4.53 (3H, m), 5.63-5.74 (1H, m), 7.29-7.37 (2-H, m), 7.38-7.46 (2H, m), 7.55-7.65 (2H, m), 7.74-7.82 (2H, m).

Production Example 1-2-2

Methyl(2S)-2-(((9H-fluoren-9-ylmethoxy)carbonyl)amino)-3-(((4-methylbenzene)sulfonyl)oxy)propanoate

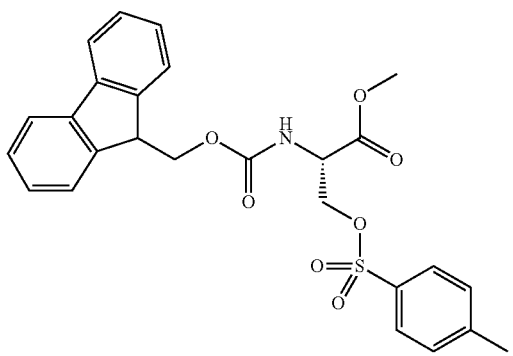 [SMILES: COC(=O)[C@H](COS(=O)(=O)c1ccc(C)cc1)NC(=O)OCC1c2ccccc2-c2ccccc21]

To a mixed solution of methyl(2S)-2-(((9H-fluoren-9-ylmethoxy)carbonyl)amino)-3-hydroxypropanoate (5.00 g, 14.6 mmol) described in Production Example 1-2-1 and pyridine (25 mL) were added 4-dimethylaminopyridine (18.0 mg, 0,146 mmol) and p-toluenesulfonyl chloride (5.58 g, 29.3 mmol) at 0° C., and the resultant mixture was stirred at 0° C. for 7 hours. Water was added to the reaction mixture, and the resultant solution was extracted with ethyl acetate two times. A combined organic layer was washed with 1 N hydrochloric acid three times, then with a saturated aqueous sodium hydrogen carbonate solution, and then with saturated brine. An organic layer was dried over anhydrous magnesium sulfate and then filtrated. The solvent was evaporated under a reduced pressure, then ethyl acetate, diethyl ether and heptane were added to the resultant residue, and then a precipitate was collected by filtration to give the title compound (6.20 g, yield: 85%).

$^1$H-NMR Spectrum (400 MHz, CDCl$_3$) δ(ppm): 2.37 (3H, s), 3.74 (31H, s), 4.16-4.23 (1H, m), 4.23-4.31 (1H, m), 432-4.40 (2H, m), 4.41-4.48 (1H, m), 4.54-4.62 (1H, m), 5.63-5.66 (1H, m), 7.26-7.37 (4H, m), 7.38-7.45 (2H, m), 7.56-7.64 (2H, m), 7.72-7.81 (4H, m).

Production Example 1-2-3

Methyl(2R)-2-(((9H-fluoren-9-ylmethoxy)carbonyl) amino)-3-iodopropanoate

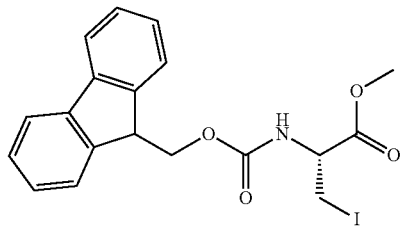 [SMILES: COC(=O)[C@H](CI)NC(=O)OCC1c2ccccc2-c2ccccc21]

To a mixed solution of methyl(2S)-2-(((9H-fluoren-9-yl-methoxy)carbonyl)amino)-3-(((4-methylbenzene)sulfonyl) oxy)propanoate (6.20 g, 12.5 mmol) described in Production Example 1-2-2 and acetone (50 mL) was added sodium iodide (9.38 g, 62.6 mmol) at room temperature. The resultant mixture was stirred at room temperature for 90 hours and 50 minutes. The reaction mixture was filtrated, and a filtrate was concentrated under a reduced pressure. Water was added to the residue, and the resultant solution was extracted with ethyl acetate. An organic layer was washed with water, then with a saturated aqueous sodium thiosulfate solution, and then saturated brine. An organic layer was dried over anhydrous magnesium sulfate and then filtrated. The solvent was evaporated under a reduced pressure, then diethyl ether and heptane were added to the resultant residue, and a precipitate was collected by filtration to give the title compound (3.82 g, yield: 68%).

$^1$H-NMR Spectrum (400 MHz, CDCl$_3$) δ(ppm): 3.55-3.66 (2H, m), 3.84 (3H, s), 4.20-4.30 (1H, m), 4.35-4.48 (2H, m), 4.56-4.62 (1H, m), 5.63-5.72 (1H, m), 7.30-7.37 (2H, m), 7.38-7.45 (2H, m), 7.62 (2H, d, J=7.2 Hz), 7.78 (2H, d, J=7.5 Hz).

Production Example 1-2-4

4-(Benzyloxy)-1-bromo-2-fluorobenzene

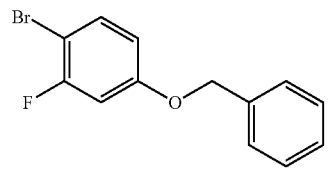 [SMILES: Fc1cc(OCc2ccccc2)ccc1Br]

To a mixed solution of a commercially available product of 4-bromo-3-fluorophenol (15.0 g, 78.5 mmol) and DMF (30 mL) were added potassium carbonate (21.7 g, 157 mmol) and benzyl bromide (10.2 mL, 86.4 mmol) at room temperature, and the resultant mixture was stirred at room temperature for 20 minutes and then at 70° C. for 40 minutes. The reaction mixture was cooled to room temperature, then water was added to the reaction mixture, and the resultant solution was extracted with ethyl acetate. An organic layer was washed with water and then with saturated brine. An organic layer was dried over anhydrous magnesium sulfate and then filtrated. The solvent was evaporated under a reduced pressure, and the resultant residue was purified by silica gel column chromatography (heptane:ethyl acetate=5:1) to give the title compound (22.7 g, yield: quantitative).

$^1$H-NMR Spectrum (400 MHz, CDCl$_3$) δ(ppm): 5.04 (2H, s), 6.65-6.72 (1H, m), 6.75-6.80 (14, m), 7.30-7.45 (6H, m).

Production Example 1-2-5

4-(Benzyloxy)-2-fluoro-1-iodobenzene

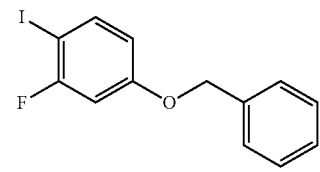 [SMILES: Fc1cc(OCc2ccccc2)ccc1I]

To a mixed solution of 4-(benzyloxy)-1-bromo-2-fluorobenzene (187 g, 665 mmol) described in Production Example 1-2-4 and 1,4-dioxane (300 mL) were added copper iodide (I) (12.6 g, 66.1 mmol), sodium iodide (200 g, 1.33 mol) and N,N'-dimethylethylenediamine (14.0 mL, 132 mmol) at room temperature, and the resultant mixture was stirred under a nitrogen atmosphere at 110 to 115° C. for 19 hours. The reaction mixture was cooled to room temperature, then water and ethyl acetate were added to the reaction mixture, the resultant mixture was filtrated using Celite, and a filtrate was partitioned between aqueous layer and organic layer. The aqueous layer was extracted with ethyl acetate. The combined organic layers were filtrated using a glass filter having silica gel laid thereon. The silica gel was washed with ethyl acetate, organic layers obtained were combined, and the solvent was evaporated under a reduced pressure. The resultant residue was purified by silica gel column chromatography (heptane:ethyl acetate=7:1 and then 4:1) to give the title compound (195 g, yield: 89%).

¹H-NMR Spectrum (400 MHz, CDCl₃) δ(ppm): 5.04 (2H, s), 6.57-6.62 (1H, m), 6.73 (1H, dd, J=2.8 Hz, 10.0 Hz), 7.31-7.43 (5H, m), 7.55-7.60 (1H, m).

Production Example 1-2-6

Methyl(2S)-3-(4-(benzyloxy)-2-fluorophenyl)-2-(((9H-fluoren-9-ylmethoxy)carbonyl)amino)propanoate

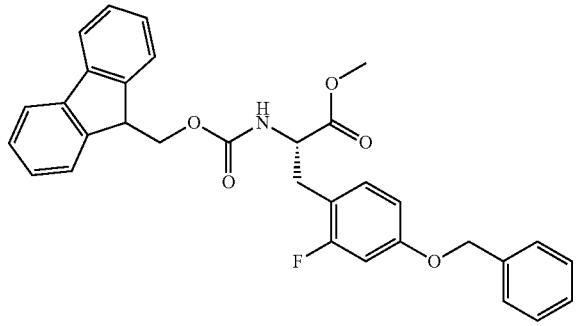 [SMILES: COC(=O)[C@H](Cc1ccc(OCc2ccccc2)cc1F)NC(=O)OCC1c2ccccc2-c2ccccc21]

A zinc powder (51.6 g, 789 mmol) was added to 1 N hydrochloric acid (100 mL), the resultant mixture was sonicated and then allowed to stand, and then a supernatant was removed therefrom. This procedure was repeated two times. Water (300 mL) was added to the resultant zinc residue, the resultant solution was stirred and then allowed to stand, and then a supernatant was removed therefrom. This procedure was repeated three times. Acetone (300 mL) was added to the resultant product, the mixture was stirred and then allowed to stand, a supernatant was removed therefrom, then diethyl ether (300 mL) was added to the solution, the resultant solution was stirred and then allowed to stand, a supernatant was removed therefrom, and a residue was then dried under reduced pressure to give activated zinc. To the activated zinc were added DMF (120 mL) and iodine (3.36 g, 13.2 mmol) under a nitrogen atmosphere at room temperature. The resultant mixture was stirred at room temperature for 45 minutes. To the reaction mixture was added a solution of methyl(2R)-2-(((9H-fluoren-9-ylmethoxy)carbonyl)amino)-3-iodopropanoate (120 g, 266 mmol) described in Production Example 1-2-3 in DMF (500 mL) over 30 minutes under a nitrogen atmosphere at room temperature. The resultant mixture was stirred at room temperature for 40 minutes. To the reaction mixture were added 4-(benzyloxy)-2-fluoro-1-iodobenzene (104 g 318 mmol) described in Production Example 1-2-5, tris(dibenzylideneacetone)palladium (0) (6.00 g, 6.55 mmol) and 2-dicyclohexylphosphino-2',6'-dimethoxybiphenyl (5.40 g, 13.2 mmol) under a nitrogen atmosphere at room temperature. The resultant mixture was stirred at room temperature for 20 hours and 40 minutes. Water and ethyl acetate were added to the reaction mixture, and the resultant solution was filtrated using Celite. A filtrate was partitioned, and an aqueous layer was further extracted with ethyl acetate three times. A combined organic layer was washed with water and saturated brine. An organic layer was dried over anhydrous magnesium sulfate and then filtrated. The solvent was evaporated under a reduced pressure, then diethyl ether (1.00 L) and heptane (1.00 L) were added to the resultant residue, and then a precipitate was collected by filtration. Diethyl ether (500 mL) and heptane (500 mL) were added to the filtrated solid, and a precipitate was collected by filtration to give the title compound (107 g, yield: 77%).

¹H-NMR Spectrum (400 MHz, CDCl₃) δ(ppm): 3.03-3.20 (2H, m), 3.75 (3H, s), 4.20 (1H, t, J=6.6 Hz), 4.25-4.38 (1H, m), 4.43 (1H, dd, J=7.1 Hz, 10.4 Hz), 4.58-4.70 (1H, m), 4.99 (2H, s), 5.33 (1H, d, J=8.4 Hz), 6.63-6.72 (2H, m), 6.94-7.03 (1H, m), 7.26-7.48 (9H, m), 7.52-7.62 (2H, m), 7.77 (2H, d, J=7.7 Hz).

Production Example 1-2-7

(2S)-3-(4-(Benzyloxy)-2-fluorophenyl)-2-(((9H-fluoren-9-ylmethoxy)carbonyl)amino)propanoic acid

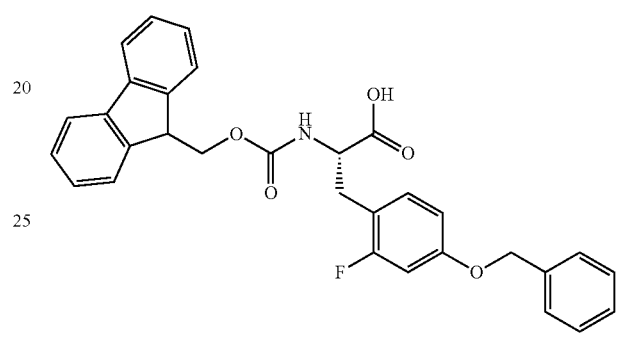

To a mixed solution of methyl(2S)-3-(4-(benzyloxy)-2-fluorophenyl)-2-(((9H-fluoren-9-ylmethoxy)carbonyl)amino)propanoate (60.0 g, 114 mmol) described in Production Example 1-2-6 and ethyl acetate (1331 mL) was added lithium iodide (92.0 g, 685 mmol) at room temperature. The resultant mixture was stirred under reflux for 23 hours and 45 minutes. The reaction mixture was cooled to 0° C., and a precipitate was collected by filtration. To the resultant solid was added 1 N hydrochloric acid (228 mL). The resultant solution was extracted with ethyl acetate. An organic layer was dried over anhydrous magnesium sulfate and then filtrated. The solvent was evaporated under a reduced pressure to give the title compound (42.2 g, yield: 72%).

¹H-NMR Spectrum (400 MHz, CDCl₃) δ(ppm): 3.05-3.15 (1H, m), 3.18-3.30 (1H, m), 4.15-4.23 (1H, m), 4.25-4.50 (2H, m), 4.60-4.70 (1H, m), 4.99 (2H, m), 5.29 (1H, d, J=7.6 Hz), 6.64-6.73 (2H, m), 7.06 (1H, dd, J=8.0 Hz, 9.6 Hz), 7.24-7.44 (9H, m), 7.55 (2H, dd, J=6.4 Hz, 6.4 Hz), 7.76 (2H, d, J=7.6 Hz).

ESI-MS (m/z): 512.30 [M+H]⁺.

Production Example 1-3-1

1-(1-(Diphenylmethyl)azetidin-3-yl)-4-ethylpiperazine

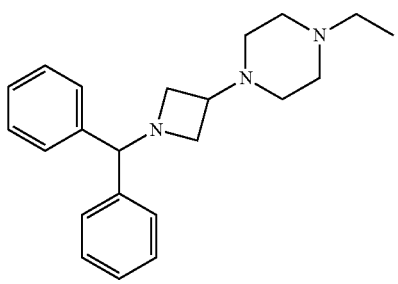 [SMILES: CCN1CCN(C2CN(C(c3ccccc3)c3ccccc3)C2)CC1]

To a mixed solution of a commercially available product of 1-(diphenylmethyl)azetidin-3-one (10.1 g, 42.6 mmol), THF (100 mL) and acetic acid (5.00 mL) was added ethylpiperazine (6.48 mL, 51.1 mmol) at room temperature. The resultant mixture was stirred at room temperature for 45 minutes. Sodium triacetoxyborohydride (18.1 g, 85.1 mmol) was added to the reaction mixture at room temperature and then stirred at room temperature for 15 hours. Sodium hydrogen carbonate and water were added to the reaction mixture, and the resultant solution was then extracted with ethyl acetate. An organic layer was washed with saturated brine, then dried over anhydrous magnesium sulfate, and then filtrated. The solvent was evaporated under a reduced pressure, and the resultant residue was purified by silica gel column chromatography (ethyl acetate-methanol) and was then further purified by NH silica gel column chromatography (heptane:ethyl acetate=2:1 and the 1:1) to give the title compound (12.7 g, yield: 89%).

$^1$H-NMR Spectrum (400 MHz, CDCl$_3$) δ(ppm): 1.07 (3H, t, J=7.6 Hz), 2.20-2.65 (10H, m), 2.85-2.93 (2H, m), 2.95-3.05 (1H, m), 3.35-3.45 (2H, m), 4.41 (1H, s), 7.15-7.20 (2H, m), 7.23-7.29 (4H, m), 7.37-7.42 (4H, m).

Production Example 1-3-2

1-(Azetidin-3-yl)-4-ethylpiperazine

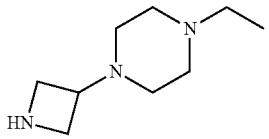

To a mixed solution of 1-(1-(diphenylmethyl)azetidin-3-yl)-4-ethylpiperazine (12.7 g, 37.9 mmol) described in Production Example 1-3-1 and methanol (50 mL) was added palladium hydroxide-carbon (5.00 g) at room temperature. The resultant mixture was stirred under a hydrogen atmosphere at room temperature and at 0.35 MPa to 0.40 MPa for 10 hours. The reaction mixture was purged with a nitrogen atmosphere and was then filtrated using Celite. A filtrate was concentrated under a reduced pressure to give the title compound in the form of a mixture (12.4 g) with benzylbenzene. The product was used in the subsequent reaction without further purification.

$^1$H-NMR Spectrum (400 MHz, CDCl$_3$) δ(ppm): 1.09 (3H, t, J=7.2 Hz), 2.10-2.80 (10H, m), 3.20-3.30 (1H, m), 3.53-3.60 (2H, m), 3.60-3.70 (2H, m).

Example 2

(6S,9aS)-N-Benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

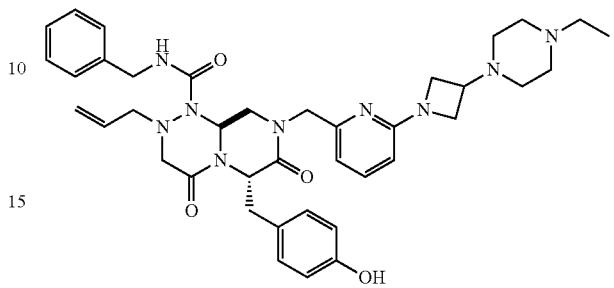

To a mixed solution of (6S,9aS)-N-benzyl-8-((6-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide (30.0 mg, 0.0537 mmol) described in Production Example 2-4 and NMP (2.0 mL) was added a mixture (45.0 mg) of 1-(azetidin-3-yl)-4-ethylpiperazine and benzylbenzene described in Production Example 1-3-2 at room temperature. The resultant mixture was irradiated with a microwave at 140° C. for 8 hours. Water was added to the reaction mixture, the resultant solution was extracted with ethyl acetate, and an organic layer was washed with saturated brine. An organic layer was dried over anhydrous magnesium sulfate and then filtrated. The solvent was evaporated under a reduced pressure, the resultant residue was purified by NH silica gel column chromatography (ethyl acetate:methanol=20:1), and was then further purified by NH silica gel thin-layer chromatography (ethyl acetate). The resultant product was further purified by silica gel thin-layer chromatography (methanol) and was then filtrated using a NH silica gel to give the title compound (14.0 mg, yield: 37%).

$^1$H-NMR Spectrum (400 MHz, CDCl$_3$) δ(ppm): 1.02 (3H, t, J=7.1 Hz), 2.30-2.70 (10H, m), 3.05-3.15 (1H, m), 3.15-3.30 (1H, m), 3.43 (2H, d, J=17.2 Hz), 3.50-3.70 (5H, m), 3.75-3.83 (1H, m), 3.83-3.90 (1H, m), 4.00-4.10 (2H, m), 4.15-4.30 (2H, m), 4.35-4.45 (1H, m), 5.00 (1H, d, J=13.4 Hz), 5.03-5.10 (1H, m), 5.15-5.30 (3H, m), 5.60-5.80 (1H, m), 6.30 (1H, d, J=8.1 Hz), 6.39 (2H, d, J=8.3 Hz), 6.56 (2H, d, J=8.4 Hz), 6.70-6.78 (2H, m), 7.18-7.24 (2H, m), 7.26-7.32 (1H, m), 7.34-7.40 (2H, m), 7.44-7.52 (1H, m).
ESI-MS (m/z): 708.67 [M+H]$^+$.

Production Example 2-1

9H-Fluoren-9-ylmethyl N-((1S)-2-(4-(tert-butoxy)phenyl)-1-((2,2-diethoxyethyl)((6-fluoropyridin-2-yl)methyl)carbamoyl)ethyl)carbamate

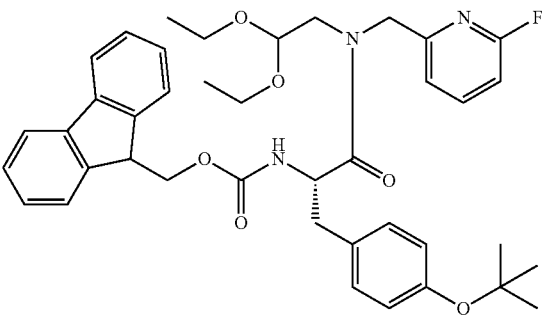 [SMILES: CCOC(CN(Cc1cccc(F)n1)C(=O)[C@H](Cc1ccc(OC(C)(C)C)cc1)NC(=O)OCC1c2ccccc2-c2ccccc21)OCC]

To a mixed solution of (2,2-diethoxyethyl)((6-fluoropyridin-2-yl)methyl)amine (514 mg, 2.12 mmol) described in Production Example 1-1-1 and DMF (10 mL) were added a commercially available product of (2S)-3-(4-(tert-butoxy)phenyl)-2-(((9H-fluoren-9-ylmethoxy)carbonyl)amino)propanoic acid (886 mg, 2.12 mmol), triethylamine (355 μL, 2.54 mmol) and HATU (968 mg, 2.54 mmol) at room temperature. The resultant mixture was stirred at room temperature for 45 minutes. Water was added to the reaction mixture, and the resultant mixture was then extracted with ethyl acetate. An organic layer was washed with water and saturated brine, was then dried over anhydrous magnesium sulfate, and was then filtrated. The solvent was evaporated under a reduced pressure, and the resultant residue was purified by silica gel column chromatography (heptane:ethyl acetate=1:1 and then ethyl acetate) to give the title compound (1.37 g, yield: 94%).

ESI-MS (m/z): 684.58 [M+H]$^+$.

Production Example 2-2

(2S)-2-Amino-3-(4-(tert-butoxy)phenyl)-N-(2,2-diethoxyethyl)-N-((6-fluoropyridin-2-yl)methyl)propanamide

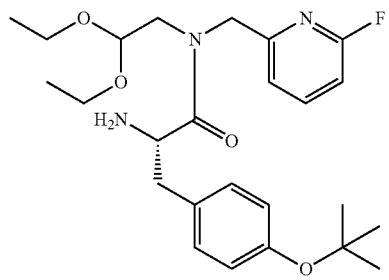 [SMILES: CCOC(CN(Cc1cccc(F)n1)C(=O)[C@@H](N)Cc1ccc(OC(C)(C)C)cc1)OCC]

To a mixed solution of 9H-fluoren-9-ylmethyl N-((1S)-2-(4-(tert-butoxy)phenyl)-1-((2,2-diethoxyethyl)((6-fluoropyridin-2-yl)methyl)carbamoyl)ethyl)carbamate (1.37 g, 2.00 mmol) described in Production Example 2-1 and dichloromethane (7.0 mL) was added piperidine (7.0 mL) at room temperature. The resultant mixture was stirred at room temperature for 30 minutes. The reaction mixture was concentrated under a reduced pressure, and the resultant residue was purified by NH silica gel column chromatography (ethyl acetate) to give the title compound (881 mg, yield: 95%).

ESI-MS (m/z): 462.49 [M+H]$^+$.

Production Example 2-3

(2S)-2-(2-(((Benzylcarbamoyl)amino)(prop-2-en-1-yl)amino)acetamido)-3-(4-(tert-butoxy)phenyl)-N-(2,2-diethoxyethyl)-N-((6-fluoropyridin-2-yl)methyl)propanamide

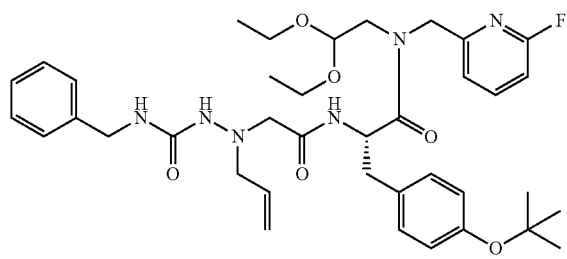 [SMILES: C=CCN(CC(=O)N[C@@H](Cc1ccc(OC(C)(C)C)cc1)C(=O)N(Cc1cccc(F)n1)CC(OCC)OCC)NC(=O)NCc1ccccc1]

To a mixed solution of (2S)-2-amino-3-(4-(tert-butoxy)phenyl)-N-(2,2-diethoxyethyl)-N-((6-fluoropyridin-2-yl)methyl)propanamide (881 mg, 1.91 mmol) described in Production Example 2-2 and DMF (10.0 mL) were added 2-(((benzylcarbamoyl)amino)(prop-2-en-1-yl)amino)acetic acid (503 mg, 1.91 mmol) described in International Publication No. 2009148192, triethylamine (532 μL, 3.82 mmol) and HATU (871 mg, 2.29 mmol) at room temperature. The resultant mixture was stirred at room temperature for 35 minutes. Water was added to the reaction mixture, and the resultant solution was extracted with ethyl acetate. An organic layer was washed with water and saturated brine, was then dried over anhydrous magnesium sulfate, and was then filtrated. The solvent was evaporated under a reduced pressure, the resultant residue was purified by NH silica gel column chromatography (ethyl acetate:methanol=20:1) to give the title compound (1.22 g, yield: 91%).

ESI-MS (m/z): 707.67 [M+H]$^+$.

Production Example 2-4

(6S,9aS)-N-Benzyl-8-((6-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

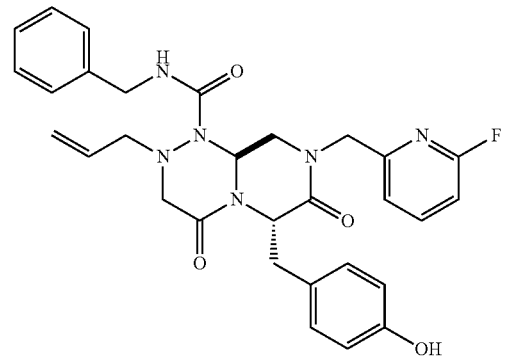

A mixed solution of (2S)-2-(2-(((benzylcarbamoyl)amino)(prop-2-en-1-yl)amino)acetamido)-3-(4-(tert-butoxy)phenyl)-N-(2,2-diethoxyethyl)-N-((6-fluoropyridin-2-yl)methyl)propanamide (1.22 g, 1.73 mmol) described in Production Example 2-3 and formic acid (26 mL) was stirred at 70° C. for 3 hours. The reaction mixture was concentrated under a reduced pressure, water was added to the residue, and the resultant solution was extracted with ethyl acetate. An organic layer was washed with water and then with saturated brine, then dried over anhydrous magnesium sulfate, and then filtrated. The solvent was evaporated under a reduced pressure, and the resultant residue was purified by NH silica gel column chromatography (ethyl acetate:methanol=20:1) to give the title compound (865 mg, yield: 90%).

$^1$H-NMR Spectrum (400 MHz, CDCl$_3$) δ(ppm): 3.30-3.42 (4H, m), 3.42-3.64 (3H, m), 3.81 (1H, dd, J=10.8 Hz, 11.2 Hz), 4.30-4.38 (1H, m), 4.40-4.48 (1H, m), 4.56-4.68 (2H, m), 5.16-5.24 (2H, m), 5.30 (1H, dd, J=4.8 Hz, 5.6 Hz), 5.35-5.44 (1H, m), 5.54-5.74 (2H, m), 6.66 (2H, d, J=8.0 Hz), 6.70-6.76 (1H, m), 6.82-6.88 (1H, m), 6.96-7.03 (2H, m), 7.06-7.12 (1H, m), 7.22-7.34 (2H, m), 7.35-7.42 (2H, m), 7.74-7.83 (1H, m).

ESI-MS (m/z): 559.41 [M+H]$^+$.

Example 3

(6S,9aS)-N-Benzyl-6-((2-fluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

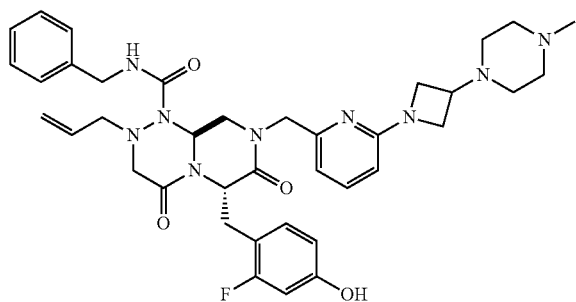

To a mixed solution of (6S,9aS)-N-benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (40.0 mg, 0.0694 mmol) described in Production Example 1-1-6 and NMP (2.0 mL) was added a mixture (112 mg) of 1-(azetidin-3-yl)-4-methylpiperazine and benzylbenzene described in Production Example 3-2 at room temperature, and the resultant mixture was irradiated with a microwave at 140° C. for 12 hours. After the mixture was cooled to room temperature, water was added to the reaction mixture, the resultant solution was extracted with ethyl acetate, and an organic layer was washed with water and then with saturated brine. An organic layer was dried over anhydrous magnesium sulfate and then filtrated. The solvent was evaporated under a reduced pressure, and the resultant residue was purified by NH silica gel column chromatography (ethyl acetate:methanol=20:1) and then further purified by NH silica gel thin-layer chromatography (ethyl acetate) to give the title compound (26.0 mg, yield: 53%).

$^1$H-NMR Spectrum (400 MHz, CDCl$_3$) δ(ppm): 2.20-2.60 (11H, m), 3.10-3.25 (2H, m), 3.43 (1H, d, J=17.1 Hz), 3.45-3.75 (7H, m), 3.86 (1H, dd, J=7.3 Hz, 9.9 Hz), 4.01 (2H, dd, J=3.5 Hz, 6.4 Hz), 4.15-4.30 (2H, m), 4.48 (1H, dd, J=6.8 Hz, 15.2 Hz), 4.95 (1H, d, J=13.8 Hz), 5.20-5.30 (3H, m), 5.53 (1H, dd, J=4.0 Hz, 10.8 Hz), 5.65-5.80 (1H, m), 5.85 (1H, dd, J=2.1 Hz, 8.5 Hz), 6.24 (1H, d, J=8.1 Hz), 6.41 (1H, dd, J=2.2 Hz, 11.6 Hz), 6.47 (1H, dd, J=8.4 Hz, 8.8 Hz), 6.69 (1H, d, J=7.3 Hz), 6.78-6.86 (1H, m), 7.20-7.32 (3H, m), 7.34-7.47 (3H, m).

ESI-MS (m/z): 712.57 [M+H]$^+$.

Production Example 3-1

1-(1-(Diphenylmethyl)azetidin-3-yl)-4-methylpiperazine

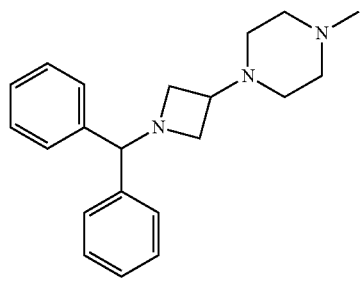 [SMILES: CN1CCN(C2CN(C(c3ccccc3)c3ccccc3)C2)CC1]

To a mixed solution of a commercially available product of 1-(diphenylmethyl)azetidin-3-one (1.00 g, 4.21 mmol), THF (20 mL) and acetic acid (1.00 mL) was added methylpiperazine (561 µL, 5.05 mmol) at room temperature. The resultant mixture was stirred at room temperature for 15 minutes. To the reaction mixture was added sodium triacetoxyborohydride (1.79 g, 8.42 mmol) at room temperature, and the resultant mixture was stirred at room temperature for 2 hours and 15 minutes. Sodium hydrogen carbonate and water were added to the reaction mixture, and the resultant mixture was extracted with ethyl acetate. An organic layer was washed with saturated brine, then dried over anhydrous magnesium sulfate, and then filtrated. The solvent was evaporated under a reduced pressure, and the resultant residue was purified by silica gel column chromatography (ethyl acetate-methanol) and then further purified by NH silica gel column chromatography (heptane:ethyl acetate=1:1) to give the title compound (1.21 g, yield: 89%).

$^1$H-NMR Spectrum (400 MHz, CDCl$_3$) δ(ppm): 2.20-2.55 (11H, m), 2.85-2.95 (2H, m), 2.95-3.05 (1H, m), 3.35-3.45 (2H, m), 4.41 (1H, s), 7.15-7.20 (2H, m), 7.23-7.30 (4H, m), 7.37-7.43 (4H, m).

ESI-MS (m/z): 322.29 [M+H]$^+$.

Production Example 3-2

1-(Azetidin-3-yl)-4-methylpiperazine

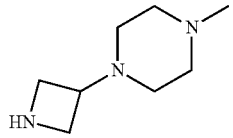

To a mixed solution of 1-(1-(diphenylmethyl)azetidin-3-yl)-4-methylpiperazine (1.21 g, 3.75 mmol) described in Production Example 3-1 and methanol (20 mL) was added palladium hydroxide-carbon (500 mg) at room temperature. The resultant mixture was stirred under a hydrogen atmosphere at room temperature and at 0.35 MPa to 0.40 MPa for 4 hours and 45 minutes. The reaction mixture was purged with a nitrogen atmosphere, and then filtrated using Celite. A filtrate was concentrated under a reduced pressure to give the title compound in the form of a mixture (1.00 g) with benzylbenzene. The product was used in the subsequent reaction without further purification.

$^1$H-NMR Spectrum (400 MHz, CDCl$_3$) δ(ppm): 2.25-2.60 (11H, m), 3.20-3.30 (1H, m), 3.50-3.70 (4H, m).

ESI-MS (m/z): 155.96 [M+H]$^+$.

Example 4

(6S,9aS)-N-Benzyl-8-((6-(3-((3S)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

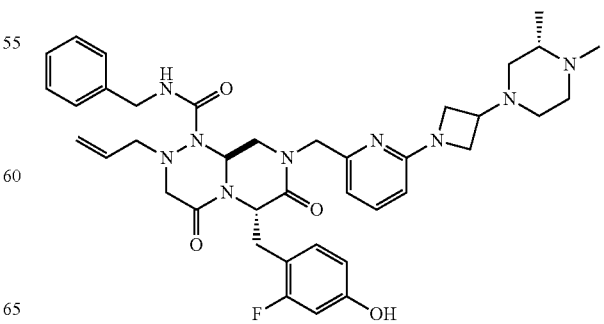

To a mixed solution of (6S,9aS)-N-benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (4.00 g 6.94 mmol) described in Production Example 1-1-6 and pyridine (100 mL) was added (2S)-4-(azetidin-3-yl)-1,2-dimethylpiperazine (2.35 g, 13.9 mmol) described in Production Example 4-3 at room temperature. The resultant mixture was stirred under reflux for 6 hours and 50 minutes. The reaction mixture was cooled to room temperature, and then concentrated under a reduced pressure. The resultant residue was purified by silica gel column chromatography (methanol), and then purified by NH silica gel column chromatography (ethyl acetate:methanol=20:1) to give the title compound (2.93 g, yield: 58%).

$^1$H-NMR Spectrum (400 MHz, CDCl$_3$) δ(ppm): 1.03 (3H, d, J=6.2 Hz), 1.76 (2H, t, J=10.8 Hz), 1.90-2.00 (1H, m), 2.10-2.35 (6H, m), 2.73 (1H, d, J=11.0 Hz), 3.08-3.20 (2H, m), 3.40-3.50 (2H, m), 3.50-3.62 (3H, m), 3.62-3.75 (3H, m), 3.85 (1H, dd, J=7.0 Hz, 9.9 Hz), 3.95-4.10 (2H, m), 4.18-4.26 (2H, m), 4.50 (1H, dd, J=7.1 Hz, 15.6 Hz), 4.95 (1H, d, J=13.5 Hz), 5.20-5.30 (3H, m), 5.55 (1H, dd, J=4.0 Hz, 10.6 Hz), 5.70-5.80 (1H, m), 5.84 (1H, dd, J=2.2 Hz, 8.4 Hz), 6.24 (1H, d, J=8.1 Hz), 6.40 (1H, dd, J=2.2 Hz, 11.7 Hz), 6.47 (1H, dd, J=8.8 Hz, 8.8 Hz), 6.69 (1H, d, J=7.3 Hz), 6.83 (1H, dd, J=6.0 Hz, 6.8 Hz), 7.22 (2H, d, J=7.3 Hz), 7.24-7.32 (1H, m), 7.34-7.46 (3H, m).

ESI-MS (m/z): 726.60 [M+H]$^+$.

Production Example 4-1

Tert-Butyl(2S)-4-(1-((benzyloxy)carbonyl)azetidin-3-yl)-2-methylpiperazine-1-carboxylate

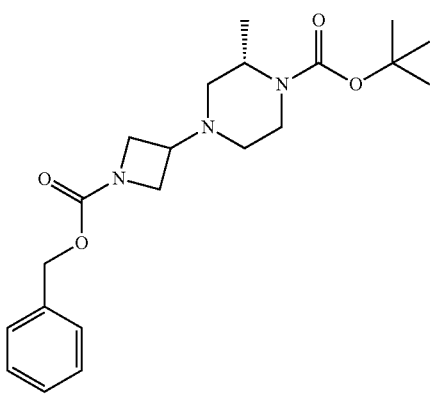 [SMILES: C[C@H]1CN(C2CN(C(=O)OCc3ccccc3)C2)CCN1C(=O)OC(C)(C)C]

To a mixed solution of benzyl 3-oxoazetidine-1-carboxylate (30.0 g, 146 mmol), which is a known and commercially available product, THF (100 mL) and acetic acid (60 mL) was added a commercially available product of tert-butyl(2S)-2-methylpiperazine-1-carboxylate (32.2 g, 161 mmol) at room temperature. The resultant mixture was stirred at room temperature for 1 hour. To the reaction mixture was added sodium triacetoxyborohydride (46.5 g, 219 mmol) at 0° C. The resultant mixture was stirred at room temperature for 1 hour and 30 minutes. To the reaction mixture were added sodium hydrogen carbonate and water at 0° C. The resultant solution was extracted with ethyl acetate. An organic layer was dried over anhydrous magnesium sulfate and then filtrated. The solvent was evaporated under a reduced pressure, and the resultant residue was purified by NH silica gel column chromatography (heptane:ethyl acetate=5:1) to give the title compound (36.7 g, yield: 64%).

ESI-MS (m/z): 390.31 [M+H]$^+$.

Production Example 4-2

Benzyl 3-((3S)-3,4-dimethylpiperazin-1-yl)azetidine-1-carboxylate

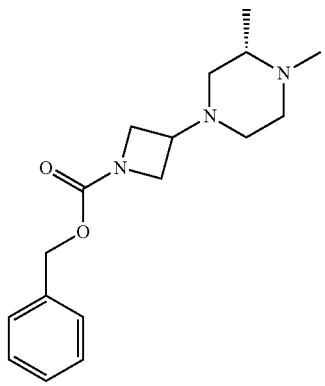 [SMILES: C[C@H]1CN(C2CN(C(=O)OCc3ccccc3)C2)CCN1C]

To a mixed solution of tert-butyl(2S)-4-(1-((benzyloxy)carbonyl)azetidin-3-yl)-2-methylpiperazine-1-carboxylate (36.7 g, 94.2 mmol) described in Production Example 4-1 and dichloromethane (20 mL) was added TFA (30 mL) at room temperature. The resultant mixture was stirred at room temperature for 35 minutes. The reaction mixture was concentrated under a reduced pressure. An aqueous formaldehyde solution (70.1 mL, 942 mmol) was added to a mixed solution of the resultant residue and THF (100 mL) at room temperature and then stirred at room temperature for 30 minutes. Sodium triacetoxyborohydride (29.9 g, 141 mmol) was added to the reaction mixture at 0° C., and the resultant mixture was stirred at room temperature for 12 hours and 45 minutes. An aqueous formaldehyde solution (10.0 mL) and sodium triacetoxyborohydride (17.5 g, 82.6 mmol) were further added to the reaction mixture at room temperature, and the resultant mixture was stirred at room temperature for 45 minutes. Sodium hydrogen carbonate and water were added to the reaction mixture at 0° C., and the resultant solution was extracted with ethyl acetate and then with dichloromethane. A combined organic layer was dried over anhydrous magnesium sulfate and then filtrated. The solvent was evaporated under a reduced pressure, and the resultant residue was purified by silica gel column chromatography (ethyl acetate:methanol=3:1) and then further purified by NH silica gel column chromatography (ethyl acetate) to give the title compound (28.6 g, yield: quantitative).

ESI-MS (m/z): 304.13 [M+H]$^+$.

Production Example 4-3

(2S)-4-(Azetidin-3-yl)-1,2-dimethylpiperazine

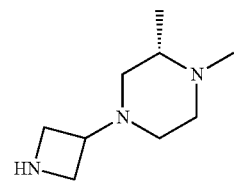

To a mixed solution of benzyl 3-((3S)-3,4-dimethylpiperazin-1-yl)azetidine-1-carboxylate (28.6 g, 94.3 mmol) described in Production Example 4-2 and methanol (150 mL) was added 10% palladium-carbon (50% aqueous, 10.0 g) at room temperature. The resultant mixture was stirred under a hydrogen atmosphere at room temperature and at 0.35 MPa to 0.40 MPa for 1 hour and 45 minutes. The reaction mixture was purged with a nitrogen atmosphere, and then filtrated using Celite. A filtrate was concentrated under a reduced pressure to give the title compound (21.2 g, yield: quantitative). The product was used in the subsequent reaction without further purification.

$^1$H-NMR Spectrum (400 MHz, CDCl$_3$) δ(ppm): 1.06 (3H, d, J=6.4 Hz), 1.70-1.82 (2H, m), 2.05-2.25 (2H, m), 2.25-2.50 (4H, m), 2.58 (1H, d, J=10.6 Hz), 2.67 (1H, dd, J=2.2 Hz, 10.6 Hz), 2.75-2.85 (1H, m), 3.25-3.38 (1H, m), 3.70-3.80 (4H, m).

Example 5

(6S,9aS)-N-Benzyl-8-((6-(3-((3R)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

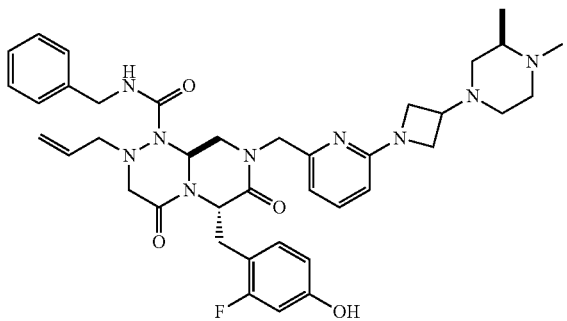

To a mixed solution of (6S,9aS)-N-benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (20.0 mg, 0.0347 mmol) described in Production Example 1-1-6 and NMP (2.0 mL) was added a mixture (59.0 mg) of (2R)-4-(azetidin-3-yl)-1,2-dimethylpiperazine and benzylbenzene described in Production Example 5-3 at room temperature. The resultant mixture was irradiated with a microwave at 140° C. for 12 hours. The reaction mixture was cooled to room temperature, and then water was added thereto, the resultant solution was extracted with ethyl acetate, and an organic layer was washed with water and then with saturated brine. An organic layer was dried over anhydrous magnesium sulfate and then filtrated. The solvent was evaporated under a reduced pressure, and the resultant residue was purified by NH silica gel column chromatography (ethyl acetate:methanol=20:1) and then further purified by NH silica gel thin-layer chromatography (ethyl acetate) to give the title compound (10.8 mg, yield: 43%).

$^1$H-NMR Spectrum (400 MHz, CDCl$_3$) δ(ppm): 0.884 (3H, d, J=6.1 Hz), 1.60-1.90 (1H, m), 2.13-2.25 (2H, m), 2.29 (3H, s), 2.33-2.42 (1H, m), 2.43-2.54 (1H, m), 2.75-2.92 (21H, m), 3.08-3.24 (2H, m), 3.25-3.35 (1H, m), 3.40 (1H, d, J=17.1 Hz), 3.45-3.77 (7H, m), 3.83-3.93 (1H, m), 4.00 (2H, d, J=7.2 Hz), 4.16-4.25 (1H, m), 4.32 (1H, dd, J=5.6 Hz, 14.4 Hz), 4.47 (1H, dd, J=7.1 Hz, 15.3 Hz), 4.95 (1H, d, J=13.8 Hz), 5.16-5.28 (2H, m), 5.56-5.66 (1H, m), 5.66-5.80 (1H, m), 5.82-5.91 (1H, m), 6.24 (1H, d, J=8.3 Hz), 6.39 (1H, d, J=11.4 Hz), 6.47-6.56 (1H, m), 6.67 (1H, d, J=7.0 Hz), 6.76-6.81 (1H, m), 7.20-7.33 (3H, m), 7.33-7.47 (3H, m).

ESI-MS (m/z): 726.71 [M+H]$^+$.

Production Example 5-1

Tert-Butyl(2R)-4-(1-(diphenylmethyl)azetidin-3-yl)-2-methylpiperazine-1-carboxylate

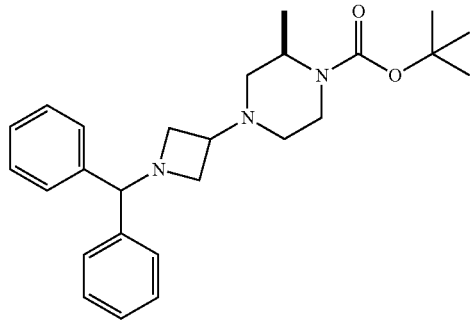 [SMILES: C[C@@H]1CN(C2CN(C(c3ccccc3)c3ccccc3)C2)CCN1C(=O)OC(C)(C)C]

To a mixed solution of a commercially available product of 1-(diphenylmethyl)azetidin-3-one (300 mg, 1.26 mmol), THF (6.0 mL) and acetic acid (500 μL) was added a commercially available product of tert-butyl(2R)-2-methylpiperazine-1-carboxylate (304 mg, 1.51 mmol) at room temperature. The resultant mixture was stirred at room temperature for 25 minutes. Sodium triacetoxyborohydride (536 mg, 2.52 mmol) was added to the reaction mixture at room temperature, and the resultant mixture was stirred at room temperature for 18 hours and 35 minutes. Sodium hydrogen carbonate and water were added to the reaction mixture, and the resultant solution was extracted with ethyl acetate. An organic layer was washed with saturated brine, then dried over anhydrous magnesium sulfate and then filtrated. The resultant residue was purified by NH silica gel column chromatography (heptane:ethyl acetate=5:1) to give the title compound (476 mg, yield: 90%).

$^1$H-NMR Spectrum (400 MHz, CDCl$_3$) δ(ppm): 1.20 (3H, d, J=6.8 Hz), 1.44 (9H, s), 1.77 (1H, td, J=3.4 Hz, 11.7 Hz), 1.96 (1H, dd, J=4.0 Hz, 11.2 Hz), 2.40 (1H, d, J=11.0 Hz), 2.56 (1H, d, J=11.2 Hz), 2.78 (1H, dd, J=6.8 Hz, 6.8 Hz), 2.83-2.95 (2H, m), 2.98-3.05 (1H, m), 3.39 (2H, dd, J=5.6 Hz, 6.4 Hz), 3.78 (1H, d, J=12.8 Hz), 4.12-4.22 (1H, m), 4.38 (1H, s), 7.15-7.21 (2H, m), 7.24-7.30 (4H, m), 7.41 (4H, d, J=7.2 Hz).

Production Example 5-2

(2R)-4-(1-(Diphenylmethyl)azetidin-3-yl)-1,2-dimethylpiperazine

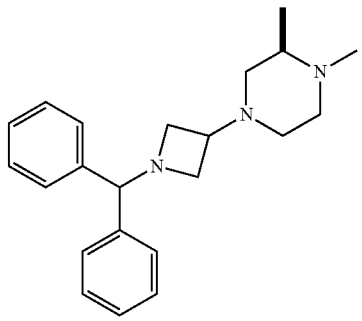 [SMILES: C[C@@H]1CN(C2CN(C(c3ccccc3)c3ccccc3)C2)CCN1C]

To a mixed solution of tert-butyl(2R)-4-(1-(diphenylmethyl)azetidin-3-yl)-2-methylpiperazine-1-carboxylate (476 mg, 1.13 mmol) described in Production Example 5-1 and THF (10.0 mL) was added lithium aluminum hydride (171 mg, 4.52 mmol) at 0° C., and the resultant mixture was stirred under reflux for 1 hour and 55 minutes. The reaction mixture was cooled to 0° C., water (171 µL) and a 5 N aqueous sodium hydroxide solution (171 µL) were added thereto, and water (513 µL) was additionally added thereto. The reaction mixture was filtrated using Celite and then washed with ethyl acetate. A filtrate was concentrated under a reduced pressure and the resultant residue was purified by NH silica gel column chromatography (heptane:ethyl acetate=2:1) to give the title compound (342 mg, yield: 90%).

$^1$H-NMR Spectrum (400 MHz, CDCl$_3$) δ(ppm): 1.01 (3H, d, J=6.0 Hz), 1.67 (1H, dd, J=10.4 Hz, 10.8 Hz), 2.00-2.10 (2H, m), 2.20-2.33 (4H, m), 2.54 (1H, d, J=10.8 Hz), 2.63 (1H, d, J=12.3 Hz), 2.75 (1H, d, J=11.6 Hz), 2.87-3.00 (31, m), 3.35-3.42 (2H, m), 4.14 (1H, s), 7.15-720 (2H, m), 7.23-7.29 (4H, m), 7.37-7.42 (41, m).

Production Example 5-3

(2R)-4-(Azetidin-3-yl)-1,2-dimethylpiperazine

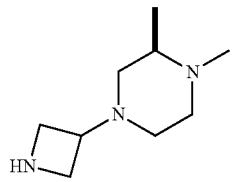

To a mixed solution of (2R)-4-(1-(diphenylmethyl)azetidin-3-yl)-1,2-dimethylpiperazine (342 mg, 1.02 mmol) described in Production Example 5-2 and methanol (10 mL) was added palladium hydroxide-carbon (200 mg) at room temperature. The resultant mixture was stirred under a hydrogen atmosphere at room temperature and at 0.35 MPa to 0.40 MPa for 5 hours. The reaction mixture was purged with a nitrogen atmosphere, and then filtrated using Celite. A filtrate was concentrated under a reduced pressure to give a mixture (287 mg) of the title compound and benzylbenzene. The product was used in the subsequent reaction without further purification.

$^1$H-NMR Spectrum (400 MHz, CDCl$_3$) δ(ppm): 1.06 (3H, d, J=6.0 Hz), 1.65-1.80 (21H, m), 1.90-2.20 (2H, m), 2.25-2.35 (4H, m), 2.58 (1H, d, J=10.6 Hz), 2.67 (114, d, J=9.2 Hz), 2.80 (1H, d, J=11.3 Hz), 3.22-3.30 (1H, m), 3.60-3.75 (4H, m).

Example 6

(6S,9aS)-N-Benzyl-8-((6-(3-((2S)-2,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

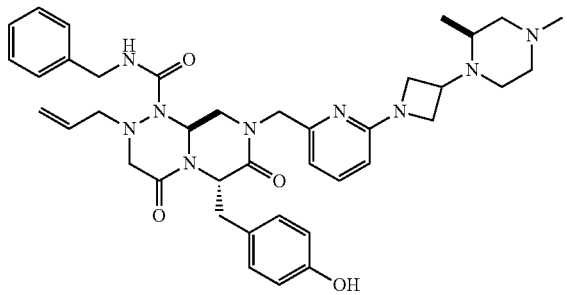

To a mixed solution of (6S,9aS)-N-benzyl-8-((6-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide (3.68 g, 6.59 mmol) described in Production Example 2-4 and pyridine (20 mL) was added a mixture (4.45 g) of (2S)-1-(azetidin-3-yl)-2,4-dimethylpiperazine and benzylbenzene described in Production Example 6-3 at room temperature. The resultant mixture was stirred under reflux for 5 hours and 45 minutes. The reaction mixture was cooled to room temperature, and was then concentrated under a reduced pressure. The resultant residue was purified by silica gel column chromatography (ethyl acetate:methanol=20:1 and subsequently methanol) and then further purified by NH silica gel column chromatography (ethyl acetate:methanol=20:1) to give a solid material. Ethyl acetate, diethyl ether and heptane were added to the solid material, and a precipitate was collected by filtration to give the title compound (3.44 g, yield: 74%).

$^1$H-NMR Spectrum (400 MHz, CDCl$_3$) δ(ppm): 1.07 (3H, d, J=6.2 Hz), 1.50-1.70 (1H, m), 1.95-2.10 (2H, m), 2.18 (3H, s), 2.25-2.40 (2H, m), 2.59 (1H, d, J=11.3 Hz), 3.10 (1H, dd, J=4.8 Hz, 13.9 Hz), 3.25-3.50 (4H, m), 3.52-3.75 (6H, m), 3.85-3.92 (1H, m), 4.10-4.26 (4H, m), 4.37 (1H, dd, J=6.6 Hz, 15.4 Hz), 4.99 (1H, d, J=13.1 Hz), 5.08-5.15 (1H, m), 5.16-5.30 (3H, m), 5.68-5.80 (1H, m), 6.33 (1H, d, J=8.4 Hz), 6.43 (2H, d, J=8.4 Hz), 6.55 (2H, d, J=8.1 Hz), 6.69 (1H, dd, J=6.0 Hz, J=6.4 Hz), 6.78 (1H, d, J=7.3 Hz), 7.19 (2H, d, J=7.0 Hz), 7.24-7.32 (1H, m), 7.34-7.40 (2H, m), 7.46-7.52 (1H, m).

ESI-MS (m/z): 708.56 [M+H]$^+$.

Production Example 6-1

Tert-Butyl(3S)-4-(1-(diphenylmethyl)azetidin-3-yl)-3-methylpiperazine-1-carboxylate

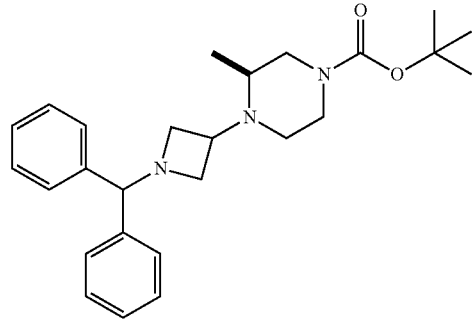 [SMILES: C[C@H]1CN(C(=O)OC(C)(C)C)CCN1C1CN(C(c2ccccc2)c2ccccc2)C1]

To a mixed solution of a commercially available product of 1-(diphenylmethyl)azetidin-3-one (300 mg, 1.26 mmol), THF (6.0 mL) and acetic acid (500 µL) was added a commercially available product of tert-butyl(3S)-3-methylpiperazine-1-carboxylate (304 mg, 1.51 mmol) at room temperature. The resultant mixture was stirred at room temperature for 1 hour and 40 minutes. Sodium triacetoxyborohydride (536 mg, 2.52 mmol) was added to the reaction mixture at room temperature, and the resultant mixture was stirred at room temperature for 13 hours and 45 minutes. Sodium hydrogen carbonate and water were added to the reaction mixture, and the resultant solution was extracted with ethyl acetate. An organic layer was washed with saturated brine and then dried over anhydrous magnesium sulfate and then filtrated. A filtrate was concentrated under a reduced pressure and the resultant residue was purified by NH silica gel column chromatography (heptane:ethyl acetate=5:1) to give the title compound (493 mg, yield: 93%).

¹H-NMR Spectrum (400 MHz, CDCl₃) δ(ppm): 0.89 (3H, d, J=6.4 Hz), 1.44 (9H, s), 1.90-2.05 (1H, m), 2.20-2.35 (1H, m), 2.54 (1H, d, J=10.6 Hz), 2.65-3.00 (4H, m), 3.08-3.23 (2H, m), 3.35-3.42 (1H, m), 3.43-3.52 (1H, m), 3.60-3.70 (1H, m), 4.37 (1H, s), 7.15-7.22 (2H, m), 7.23-7.30 (4H, m), 7.36-7.42 (4H, m).

Production Example 6-2

(2S)-1-(1-(Diphenylmethyl)azetidin-3-yl)-2,4-dimethylpiperazine

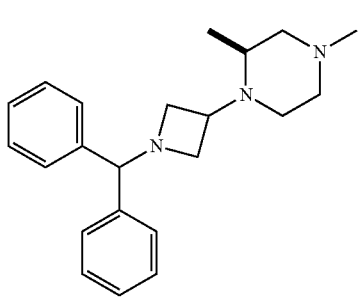 [SMILES: C[C@H]1CN(C)CCN1C1CN(C(c2ccccc2)c2ccccc2)C1]

To a mixed solution of tert-butyl(3S)-4-(1-(diphenylmethyl)azetidin-3-yl)-3-methylpiperazine-1-carboxylate (493 mg, 1.17 mmol) described in Production Example 6-1 and THF (10.0 mL) was added lithium aluminum hydride (178 mg, 4.68 mmol) at 0° C. The resultant mixture was stirred under reflux for 5 hours and 10 minutes. The reaction mixture was cooled to 0° C., then water (178 μL) and a 5 N aqueous sodium hydroxide solution (178 μL) were added thereto, and water (534 μL) was further added thereto. The reaction mixture was filtrated using Celite and then washed with ethyl acetate. A filtrate was concentrated under a reduced pressure, and the resultant residue was purified by NH silica gel column chromatography (heptane:ethyl acetate=2:1) to give the title compound (321 mg, yield: 82%).
¹H-NMR Spectrum (400 MHz, CDCl₃) δ(ppm): 0.90 (3H, d, J=6.4 Hz), 1.85-2.00 (1H, m), 2.03-2.13 (1H, m), 2.13-2.40 (5I, m), 2.52-2.70 (3H, m), 2.84 (1H, dd, J=7.2 Hz, 7.2 Hz), 2.94 (1H, dd, J=6.8 Hz, 7.2 Hz), 3.13 (1H, dt, J=6.7 Hz, 13.7 Hz), 3.39 (1H, td, J=2.6 Hz, 6.6 Hz), 3.49 (1H, td, J=2.7 Hz, 6.5 Hz), 4.38 (1H, s), 7.15-7.21 (2H, m), 7.23-7.30 (4H, m), 7.36-7.43 (4H, m).

Production Example 6-3

(2S)-1-(Azetidin-3-yl)-2,4-dimethylpiperazine

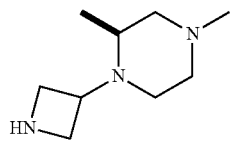

To a mixed solution of (2S)-1-(1-(diphenylmethyl)azetidin-3-yl)-2,4-dimethylpiperazine (321 mg, 0.957 mmol) described in Production Example 6-2 and methanol (7.0 mL) was added palladium hydroxide-carbon (150 mg) at room temperature. The resultant mixture was stirred under a hydrogen atmosphere at room temperature and at 0.35 MPa to 0.40 (263 mg) of the title compound and benzylbenzene. The product was used in the subsequent reaction without further purification.
ESI-MS (m/z): 170.00 [M+H]⁺.

Example 7

(6S,9aS)-N-Benzyl-8-((6-(3-(4-ethylpiperazin-1-yl)azetidin-1-yl)-5-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

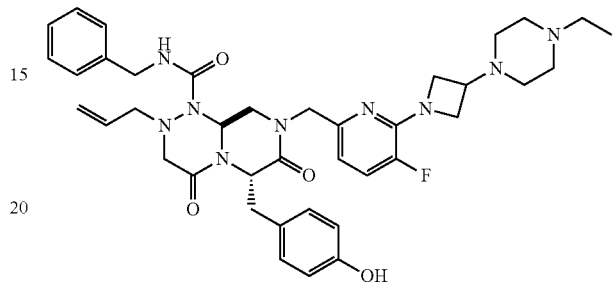

The title compound (39.0 mg, yield: 36%) was produced from (2S)-2-(2-(((benzylcarbamoyl)amino)(prop-2-en-1-yl)amino)acetamido)-3-(4-(tert-butoxy)phenyl)-N-(2,2-diethoxyethyl)-N-((6-(3-(4-ethylpiperazin-1-yl)azetidin-1-yl)-5-fluoropyridin-2-yl)methyl)propanamide (131 mg, 0.150 mmol) described in Production Example 7-5 employing the similar procedure as in Production Example 2-4.
¹H-NMR Spectrum (400 MHz, CDCl₃) δ(ppm): 1.00 (3H, t, J=7.1 Hz), 2.25-2.72 (10H, m), 3.14 (1H, dd, J=5.1 Hz, 13.7 Hz), 3.17-3.25 (1H, m), 3.40-3.70 (9H, m), 3.80-3.89 (2, m), 4.08 (1H, dd, J=4.5 Hz, 11.1 Hz), 4.18 (1H, dd, J=5.6 Hz, 15.3 Hz), 4.39-4.48 (1H, m), 4.95 (1H, d, J=13.9 Hz), 5.00-5.56 (1H, m), 5.15-5.29 (3H, m), 5.67-5.79 (1H, m), 6.46-6.61 (4H, m), 6.67 (1H, dd, J=2.7 Hz, 7.8 Hz), 6.69-6.75 (1H, m), 7.12 (1H, dd, J=7.9 Hz, 11.8 Hz), 7.18-7.42 (5H, m).
ESI-MS (m/z): 726.53 [M+H]⁺.

Production Example 7-1

(6-(3-(4-Ethylpiperazin-1-yl)azetidin-1-yl)-5-fluoropyridin-2-yl)methanol

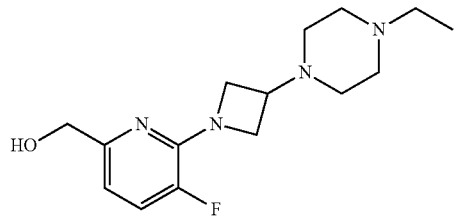 [SMILES: CCN1CCN(C2CN(c3nc(CO)ccc3F)C2)CC1]

To a mixed solution of a commercially available product of (6-chloro-5-fluoropyridin-2-yl)methanol (200 mg, 1.24 mmol) and NMP (2.00 mL) were added a mixture (627 mg) of 1-(azetidin-3-yl)-4-ethylpiperazine and benzylbenzene described in Production Example 1-3-2 and DBU (565 mg, 3.71 mmol) at room temperature. The resultant mixture was irradiated with a microwave at 180° C. for 8 hours. The reaction mixture was cooled to room temperature, then water was added thereto, and the resultant solution was extracted with dichloromethane. An organic layer was dried over anhydrous magnesium sulfate and then filtrated. The solvent was evaporated under a reduced pressure, and the resultant residue was purified by NH silica gel column chromatography (ethyl acetate:heptane=1:4 and subsequently ethyl acetate) to give a crude product (402 mg) of the title compound.

¹H-NMR Spectrum (400 MHz, CDCl₃) δ(ppm): 1.10 (3H, t, J=7.2 Hz), 2.37-2.66 (10H, m), 3.26-3.36 (1H, m), 4.00-4.08 (2H, m), 4.18-4.29 (2H, m), 4.56 (2H, s), 6.39-6.50 (1H, m), 7.05-7.18 (1H, m).

Production Example 7-2

6-(3-(4-Ethylpiperazin-1-yl)azetidin-1-yl)-5-fluoro-pyridine-2-carbaldehyde

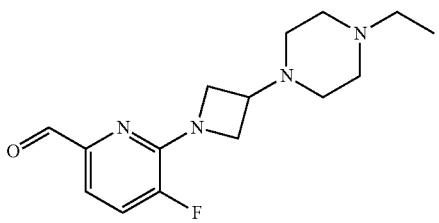 [SMILES: CCN1CCN(C2CN(c3nc(C=O)ccc3F)C2)CC1]

To a mixed solution of the crude product (402 mg) of (6-(3-(4-ethylpiperazin-1-yl)azetidin-1-yl)-5-fluoropyridin-2-yl)methanol described in Production Example 7-1 and dichloromethane (10.0 mL) was added Dess-Martin periodinane (787 mg, 1.86 mmol) at room temperature. The resultant mixture was stirred at room temperature for 2 hours. A saturated aqueous sodium thiosulfate solution and a saturated aqueous sodium hydrogen carbonate solution were added to the reaction mixture, and the resultant solution was extracted with dichloromethane. An organic layer was dried over anhydrous magnesium sulfate and then filtrated. The solvent was evaporated under a reduced pressure to give a crude product (362 mg) of the title compound. The product was used in the subsequent reaction without further purification.

Production Example 7-3

(2,2-Diethoxyethyl)((6-(3-(4-ethylpiperazin-1-yl)azetidin-1-yl)-5-fluoropyridin-2-yl)methyl)amine

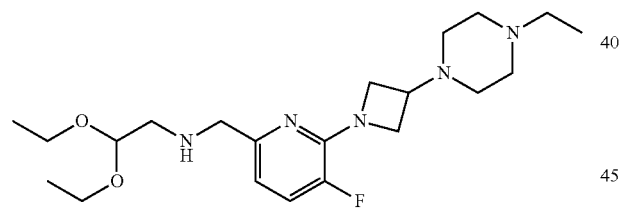

The title compound (271 mg, yield: 53%) was produced from the crude product (362 mg) of 6-(3-(4-ethylpiperazin-1-yl)azetidin-1-yl)-5-fluoropyridine-2-carbaldehyde described in Production Example 7-2 employing the similar procedure as in Production Example 1-1-1.

ESI-MS (m/z): 410.28 [M+H]⁺.

Production Example 7-4

(2S)-2-Amino-3-(4-(tert-butoxy)phenyl)-N-(2,2-diethoxyethyl)-N-((6-(3-(4-ethylpiperazin-1-yl)azetidin-1-yl)-5-fluoropyridin-2-yl)methyl)propanamide

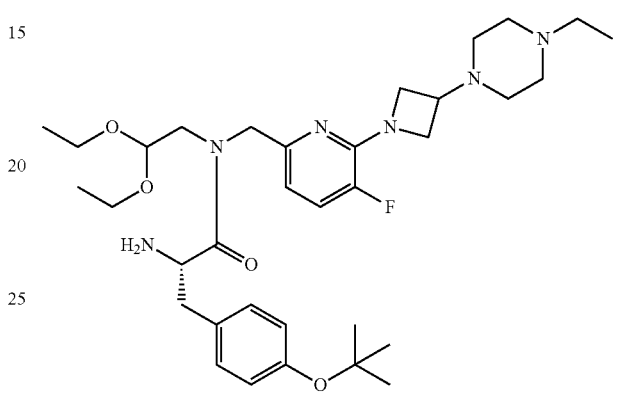

The title compound (118 mg, yield: 86%) was produced from (2,2-diethoxyethyl)((6-(3-(4-ethylpiperazin-1-yl)azetidin-1-yl)-5-fluoropyridin-2-yl)methyl)amine (90.0 mg 0.220 mmol) described in Production Example 7-3 employing the similar procedures as in Production Example 2-1 and Production Example 2-2.

ESI-MS (m/z): 629.59 [M+H]⁺.

Production Example 7-5

(2S)-2-(2-((Benzylcarbamoyl)amino)(prop-2-en-1-yl)amino)acetamido)-3-(4-(tert-butoxy)phenyl)-N-(2,2-diethoxyethyl)-N-((6-(3-(4-ethylpiperazin-1-yl)azetidin-1-yl)-5-fluoropyridin-2-yl)methyl)propanamide

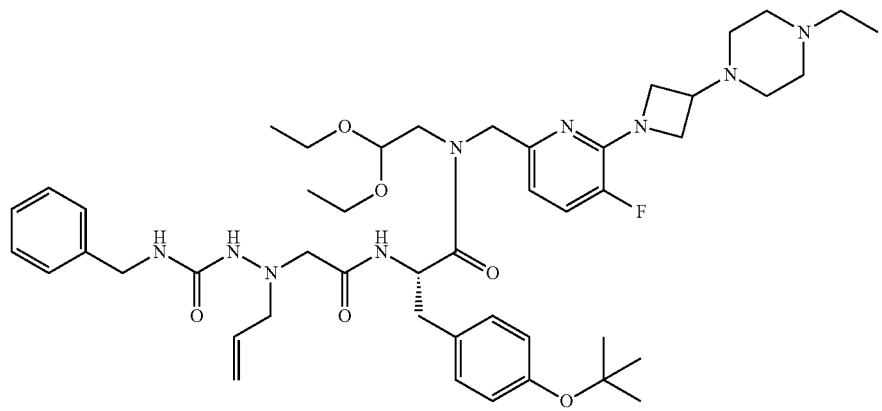 [SMILES: C=CCN(CC(=O)N[C@@H](Cc1ccc(OC(C)(C)C)cc1)C(=O)N(Cc1ccc(F)c(N2CC(N3CCN(CC)CC3)C2)n1)CC(OCC)OCC)NC(=O)NCc1ccccc1]

The title compound (131 mg, yield: 79%) was produced from (2S)-2-amino-3-(4-(tert-butoxy)phenyl)-N-(2,2-diethoxyethyl)-N-((6-(3-(4-ethylpiperazin-1-yl)azetidin-1-yl)-5-fluoropyridin-2-yl)methyl)propanamide (118 mg, 0,188 mmol) described in Production Example 7-4 employing the similar procedure as in Production Example 2-3.

ESI-MS (m/z): 874.81 [M+H]$^+$.

Example 8

(6S,9aS)-N-Benzyl-8-((5-fluoro-6-(3-(4-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

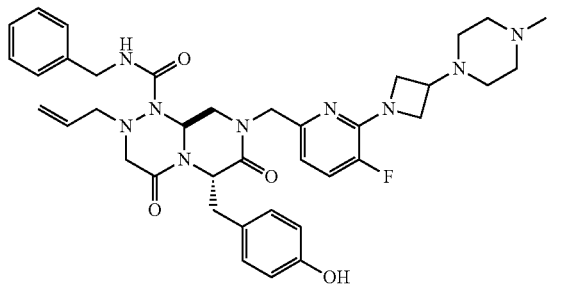

The title compound (65.0 mg, yield: 57%) was produced from (2S)-2-(2-(2-((benzylcarbamoyl)amino)(prop-2-en-1-yl)amino)acetamido)-3-(4-(tert-butoxy)phenyl)-N-(2,2-diethoxyethyl)-N-((5-fluoro-6-(3-(4-methylpiperazin-1-yl)azetidin-1-yl)pyridin-2-yl)methyl)propanamide (134 mg, 0.156 mmol) described in Production Example 8-5 employing the similar procedure as in Production Example 2-4.

$^1$H-NMR Spectrum (400 MHz, CDCl$_3$) δ(ppm): 2.25 (3H, s), 2.29-2.78 (8H, m), 3.14 (1H, dd, J=5.0 Hz, 13.8 Hz), 3.18-3.25 (1H, m), 3.38-3.70 (9H, m), 3.78-3.89 (2H, m), 4.08 (1H, dd, J=4.3 Hz, 11.3 Hz), 4.20 (1H, dd, J=5.6 Hz, 15.7 Hz), 4.35-4.46 (1H, m), 4.95 (1H, d, J=13.9 Hz), 4.99-5.06 (1H, m), 5.14-5.29 (3H, m), 5.66-5.79 (1H, m), 6.47-6.53 (2H, m), 6.55-6.61 (2H, m), 6.64-6.74 (2H, m), 7.13 (1H, dd, J=7.8 Hz, 11.9 Hz), 7.18-7.23 (2H, m), 7.28-7.42 (3H, m).

ESI-MS (m/z): 712.60 [M+H]$^+$.

Production Example 8-1

(5-Fluoro-6-(3-(4-methylpiperazin-1-yl)azetidin-1-yl)pyridin-2-yl)methanol

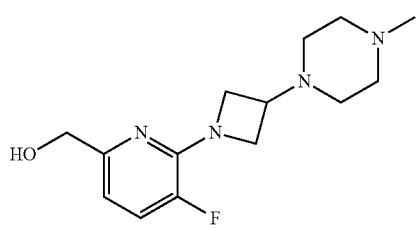 [SMILES: CN1CCN(C2CN(c3nc(CO)ccc3F)C2)CC1]

The title compound (267 mg, yield: 77%) was produced from a commercially available product of (6-chloro-5-fluoropyridin-2-yl)methanol (200 mg, 1.24 mmol) and a mixture (450 mg) of 1-(azetidin-3-yl)-4-methylpiperazine and benzylbenzene described in Production Example 3-2 employing the similar procedure as in Production Example 7-1.

$^1$H-NMR Spectrum (400 MHz, CDCl$_3$) δ(ppm): 2.31 (3H, s), 2.36-2.63 (8H, m), 3.20 (1H, m), 3.97-4.07 (2H, m), 4.18-4.27 (2H, m), 4.56 (2H, m), 6.40-6.50 (1H, m), 7.06-7.18 (1H, m).

Production Example 8-2

5-Fluoro-6-(3-(4-methylpiperazin-1-yl)azetidin-1-yl)pyridine-2-carbaldehyde

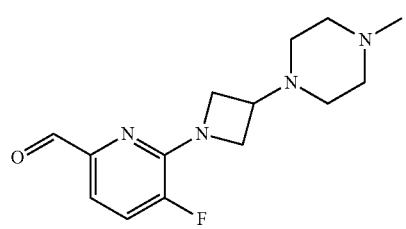 [SMILES: CN1CCN(C2CN(c3nc(C=O)ccc3F)C2)CC1]

A crude product (265 mg) of the title compound was produced from (5-fluoro-6-(3-(4-methylpiperazin-1-yl)azetidin-1-yl)pyridin-2-yl)methanol (267 mg, 0.952 mmol) described in Production Example 8-1 employing the similar procedure as in Production Example 7-2. The product was used in the subsequent reaction without further purification.

Production Example 8-3

(2,2-Diethoxyethyl)((5-fluoro-6-(3-(4-methylpiperazin-1-yl)azetidin-1-yl)pyridin-2-yl)methyl)amine

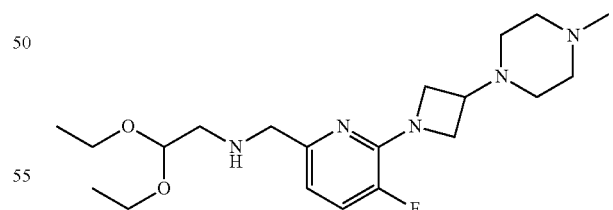

The title compound (240 mg, yield: 64%) was produced from the crude product (265 mg) of 5-fluoro-6-(3-(4-methylpiperazin-1-yl)azetidin-1-yl)pyridine-2-carbaldehyde described in Production Example 8-2 employing the similar procedure as in Production Example 1-1-1.

ESI-MS (m/z): 396.24 [M+H]$^+$.

Production Example 8-4

(2S)-2-Amino-3-(4-(tert-butoxy)phenyl)-N-(2,2-diethoxyethyl)-N-((5-fluoro-6-(3-(4-methylpiperazin-1-yl)azetidin-1-yl)pyridin-2-yl)methyl)propanamide

Example 9

(6S,9aS)-N-Benzyl-6-((4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide

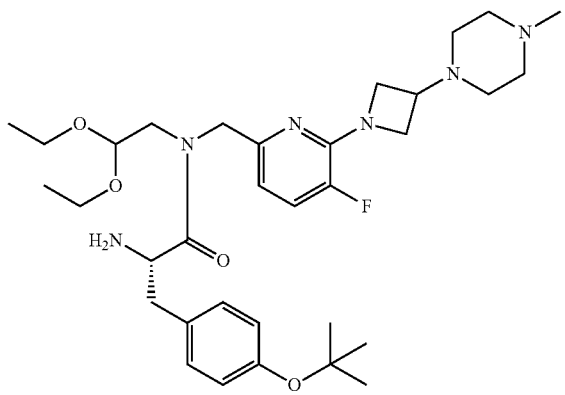 [SMILES: CCOC(CN(Cc1ccc(F)c(N2CC(N3CCN(C)CC3)C2)n1)C(=O)[C@@H](N)Cc1ccc(OC(C)(C)C)cc1)OCC]

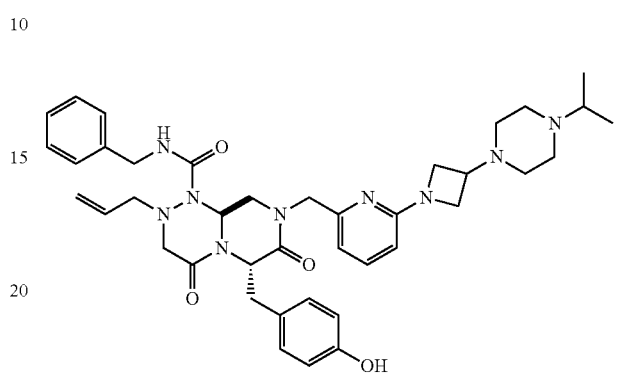

The title compound (120 mg, yield: quantitative) was produced from (2,2-diethoxyethyl)((5-fluoro-6-(3-(4-methylpiperazin-1-yl)azetidin-1-yl)pyridin-2-yl)methyl)amine (80.0 mg, 0.202 mmol) described in Production Example 8-3 employing the similar procedure as in Production Example 2-1 and Production Example 2-2.
ESI-MS (m/z): 615.58 [M+H]$^+$.

The title compound (28.5 mg, yield: 37%) was produced from (6S,9aS)-N-benzyl-8-((6-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide (60 mg, 0.107 mmol) described in Production Example 2-4 and a mixture (164 mg) of 1-(azetidin-3-yl)-4-(propan-2-yl)piperazine and benzylbenzene described in Production Example 9-2 employing the similar procedure as in Example 2.

$^1$H-NMR Spectrum (400 MHz, CDCl$_3$) δ(ppm): 0.94-1.01 (6H, m), 2.20-2.80 (9H, m), 3.10 (1H, dd, J=13.7 Hz, 5.1 Hz), 3.20 (11-1, ddd, J=6.6 Hz, 6.6 Hz, 6.6 Hz), 3.37-3.47 (2H, m), 3.50-3.70 (5H, m), 3.79 (1H, dd, J=9.8 Hz, 6.6 Hz), 3.88 (1H, dd, J=9.8 Hz, 7.0 Hz), 3.98-4.09 (2H, m), 4.14-4.23 (2H, m), 4.43 (1H, dd, J=15.2 Hz, 7.0 Hz), 4.99 (1H, d, J=13.3 Hz),

Production Example 8-5

(2S)-2-(2-((Benzylcarbamoyl)amino)(prop-2-en-1-yl)amino)acetamido)-3-(4-(tert-butoxy)phenyl)-N-(2,2-diethoxyethyl)-N-((5-fluoro-6-(3-(4-methylpiperazin-1-yl)azetidin-1-yl)pyridin-2-yl)methyl) propanamide

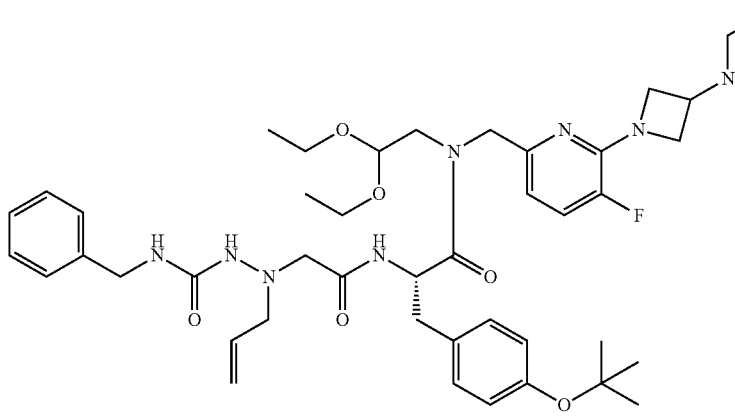

The title compound (134 mg, yield: 80%) was produced from (2S)-2-amino-3-(4-(tert-butoxy)phenyl)-N-(2,2-diethoxyethyl)-N-((5-fluoro-6-(3-(4-methylpiperazin-1-yl)azetidin-1-yl)pyridin-2-yl)methyl)propanamide (120 mg, 0.202 mmol) described in Production Example 8-4 employing the similar procedure as in Production Example 2-3.
ESI-MS (m/z): 860.94 [M+H]$^+$.

5.05 (1H, dd, J=10.9 Hz, 4.3 Hz), 5.17 (1H, dd, J=4.7 Hz, 3.1 Hz), 5.20-5.23 (1H, m), 5.23-5.27 (1H, m), 5.66-5.78 (1H, m), 6.29 (1H, d, J=7.8 Hz), 6.36-6.43 (21H, m), 6.52-6.58 (2H, m), 6.69-6.77 (2H, m), 7.19-7.23 (2H, m), 7.28-7.32 (1H, m), 7.34-7.40 (2H, m), 7.47 (1H, dd, J=8.4 Hz, 7.2 Hz)
ESI-MS (m/z): 722.59 [M+H]$^+$.

Production Example 9-1

1-(1-(Diphenylmethyl)azetidin-3-yl)-4-(propan-2-yl)piperazine

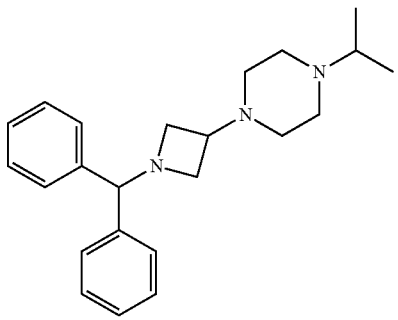 [SMILES: CC(C)N1CCN(C2CN(C(c3ccccc3)c3ccccc3)C2)CC1]

The title compound (800 mg, yield: 91%) was produced from a commercially available product of 1-(diphenylmethyl)azetidin-3-one (600 mg, 2.53 mmol) and 1-(propan-2-yl)piperazine (389 mg, 3.03 mmol) employing the similar procedure as in Production Example 1-3-1.

ESI-MS (m/z): 350.30 [M+H]$^+$.

Production Example 9-2

1-(Azetidin-3-yl)-4-(propan-2-yl)piperazine

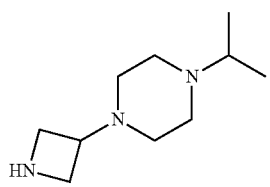

The title compound was produced in the form of a mixture (680 mg) with benzylbenzene from 1-(1-(diphenylmethyl)azetidin-3-yl)-4-(propan-2-yl)piperazine (550 mg, 1.57 mmol) described in Production Example 9-1 employing the similar procedure as in Production Example 1-3-2.

ESI-MS (m/z): 184.03 [M+H]$^+$.

Example 10

(6S,9aS)-N-Benzyl-6-((2-fluoro-4-hydroxyphenyl)methyl)-8-((5-fluoro-6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

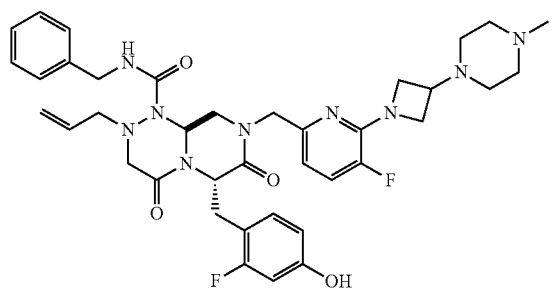

The title compound (15.0 mg, yield: 33%) was produced from (6S,9aS)-N-benzyl-6-((4-(benzyloxy)-2-fluorophenyl)methyl)-8-((5-fluoro-6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide (52.0 mg, 0.0634 mmol) described in Production Example 10-3 employing the similar procedure as in Production Example 1-1-6.

$^1$H-NMR Spectrum (400 MHz, CDCl$_3$) δ(ppm): 2.21 (3H, s), 2.22-2.76 (8H, m), 3.09-3.21 (2H, m), 3.39-3.87 (11H, m), 4.08 (1H, dd, J=4.3 Hz, 11.1 Hz), 4.16-4.23 (1H, m), 4.50 (1H, dd, J=7.2 Hz, 15.4 Hz), 4.91 (1H, d, J=13.9 Hz), 5.19-5.29 (3H, m), 5.52 (1H, dd, J=4.0 Hz, 10.8 Hz), 5.69-5.81 (1H, m), 6.01 (1H, dd, J=2.3 Hz, 8.2 Hz), 6.42-6.54 (2H, m), 6.61 (1H, dd, J=2.8 Hz, 7.9 Hz), 6.78-6.86 (1H, m), 7.09 (1H, dd, J=7.8 Hz, 11.9 Hz), 7.19-7.42 (5H, m).

ESI-MS (m/z): 730.62 [M+H]$^+$.

Production Example 10-1

(2S)-2-Amino-3-(4-(benzyloxy)-2-fluorophenyl)-N-(2,2-diethoxyethyl)-N-((5-fluoro-6-(3-(4-methylpiperazin-1-yl)azetidin-1-yl)pyridin-2-yl)methyl)propanamide

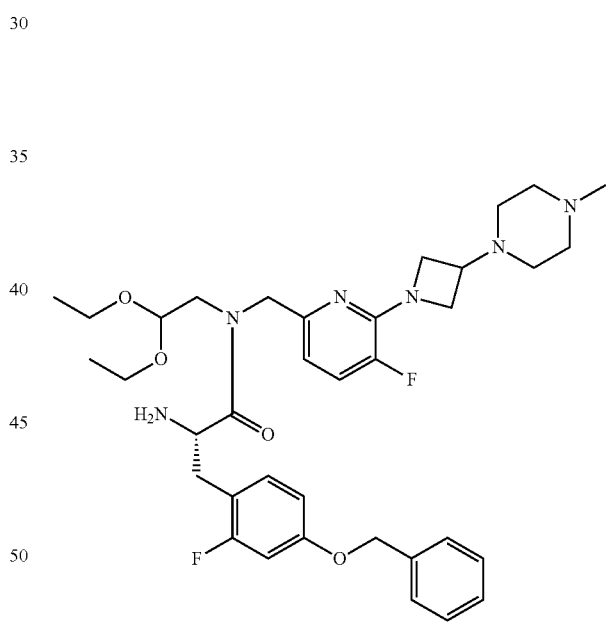

The title compound (63.0 mg, yield: 24%) was produced from (2,2-diethoxyethyl)((5-fluoro-6-(3-(4-methylpiperazin-1-yl)azetidin-1-yl)pyridin-2-yl)methyl)amine (160 mg, 0.405 mmol) described in Production Example 8-3 employing the similar procedures as in Production Example 1-1-2 and Production Example 1-1-3.

ESI-MS (m/z): 667.66 [M+H]$^+$.

Production Example 10-2

(2S)-2-(2-((Benzylcarbamoyl)amino)(prop-2-en-1-yl)amino)acetamido)-3-(4-(benzyloxy)-2-fluorophenyl)-N-(2,2-diethoxyethyl)-N-((5-fluoro-6-(3-(4-methylpiperazin-1-yl)azedin-1-yl)pyridin-2-yl)methyl)propanamide

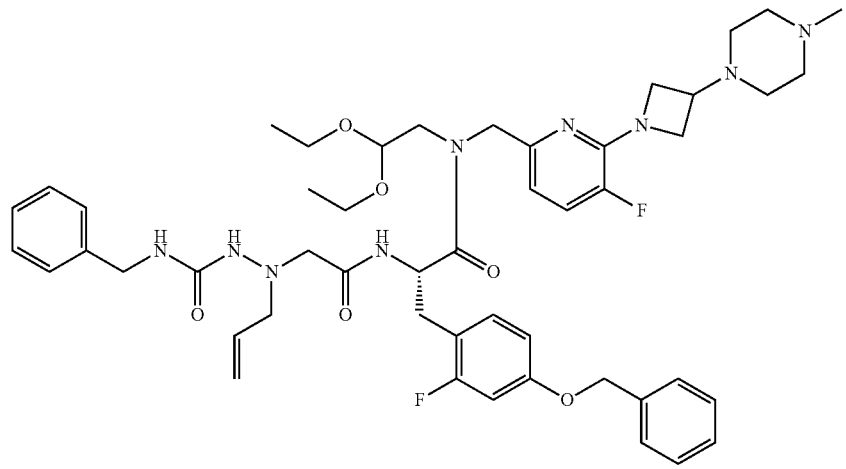 [SMILES: C=CCN(CC(=O)N[C@@H](Cc1ccc(OCc2ccccc2)cc1F)C(=O)N(Cc1ccc(F)c(N2CC(N3CCN(C)CC3)C2)n1)CC(OCC)OCC)NC(=O)NCc1ccccc1]

The title compound (58.0 mg, yield: 68%) was produced from (2S)-2-amino-3-(4-(benzyloxy)-2-fluorophenyl)-N-(2,2-diethoxyethyl)-N-((5-fluoro-6-(3-(4-methylpiperazin-1-yl)azetidin-1-yl)pyridin-2-yl)methyl)propanamide (63.0 mg, 0.0945 mmol) described in Production Example 10-1 employing the similar procedure as in Production Example 1-1-4.

ESI-MS (m/z): 912.93 [M+H]$^+$.

Production Example 10-3

(6S,9aS)-N-benzyl-6-((4-(benzyloxy)-2-fluorophenyl)methyl)-8-((5-fluoro-6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

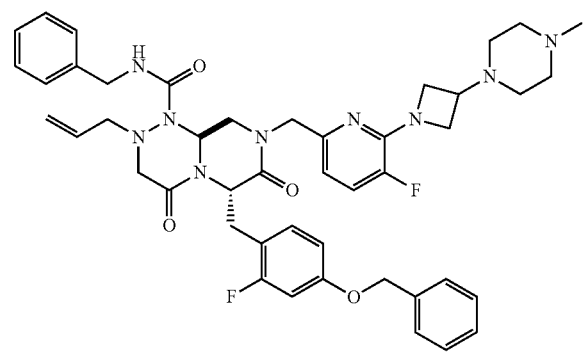

The title compound (52.0 mg, yield: quantitative) was produced from (2S)-2-(2-((benzylcarbamoyl)amino)(prop-2-en-1-yl)amino)acetamido)-3-(4-(benzyloxy)-2-fluorophenyl)-N-(2,2-diethoxyethyl)-N-((5-fluoro-6-(3-(4-methylpiperazin-1-yl)azedin-1-yl)pyridin-2-yl)methyl)propanamide (58.0 mg, 0.0634 mmol) described in Production Example 10-2 employing the similar procedure as in Production Example 1-1-5.

ESI-MS (m/z): 820.74 [M+H]$^+$.

The compounds of Examples 11 to 23 described below were synthesized by the similar procedure as in Example 1 using the below-mentioned combinations in Table 1 of the compounds of Production Examples 12-2-4, 18-3 and 19-3 described below and the compounds of Production Examples 1-1-6, 1-3-2, 2-4, 3-2, 4-3, 6-3 and 9-2 described above.

TABLE 1

| Examples | Starting materials | Starting materials |
|---|---|---|
| 11 | Production Example 1-1-6 | Production Example 9-2 |
| 12 | Production Example 9-2 | Production Example 12-2-4 |
| 13 | Production Example 1-3-2 | Production Example 12-2-4 |
| 14 | Production Example 3-2 | Production Example 12-2-4 |
| 15 | Production Example 1-1-6 | Production Example 6-3 |
| 16 | Production Example 4-3 | Production Example 12-2-4 |
| 17 | Production Example 6-3 | Production Example 12-2-4 |
| 18 | Production Example 2-4 | Production Example 18-3 |
| 19 | Production Example 2-4 | Production Example 19-3 |
| 20 | Production Example 1-1-6 | Production Example 18-3 |
| 21 | Production Example 1-1-6 | Production Example 19-3 |
| 22 | Production Example 12-2-4 | Production Example 18-3 |
| 23 | Production Example 12-2-4 | Production Example 19-3 |

Example 11

(6S,9aS)-N-Benzyl-6-((2-fluoro-4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide

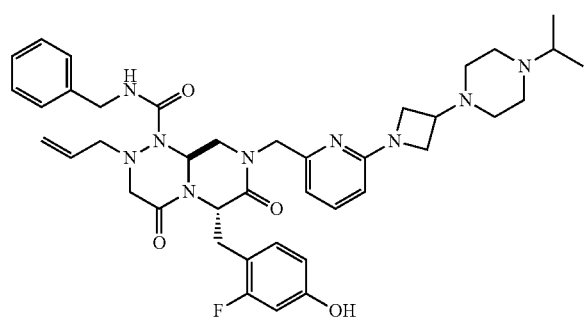

$^1$H-NMR Spectrum (400 MHz, CDCl$_3$) δ(ppm): 0.97 (6H, t, J=6.6 Hz), 2.10-2.80 (9H, m), 3.05-3.25 (2H, m), 3.35-3.75 (8H, m), 3.87 (1H, dd, J=7.4, 10 Hz), 3.95-4.05 (2H, m), 4.14-4.23 (2H, m), 4.54 (1H, dd, J=15.6 Hz, 7.4 Hz), 4.95 (1H, d, J=13.3 Hz), 5.19-5.29 (3H, m), 5.52 (1H, dd, J=10.9 Hz, 3.9 Hz), 5.75 (1H, m), 5.86 (1H, dd, J=8.2 Hz, 2.3 Hz), 6.25 (1H, d, J=8.2 Hz), 6.41 (1H, dd, J=11.7 Hz, 2.3 Hz), 6.46 (1H, dd, J=8.6 Hz, 8.6 Hz), 6.70 (1H, d, J=7.0 Hz), 6.84 (1H, dd, J=7.0 Hz, 5.9 Hz), 7.21-7.33 (3H, m), 7.38 (2H, m), 7.43 (1H, dd, J=8.4 Hz, 7.2 Hz).

ESI-MS (m/z): 740.66 [M+H]$^+$.

Example 12

(6S,9aS)-N-Benzyl-6-((2,6-difluoro-4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide

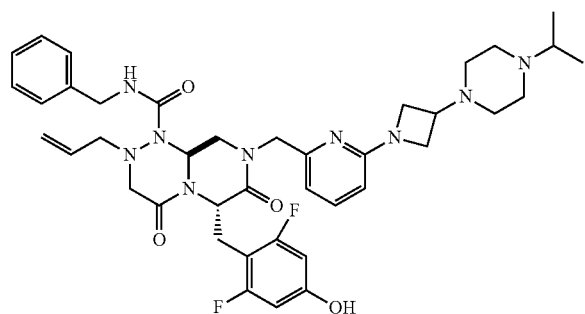

$^1$H-NMR Spectrum (400 MHz, CDCl$_3$) δ(ppm): 0.93-1.00 (6H, m), 2.25-2.75 (9H, m), 3.21 (1H, ddd, J=6.5 Hz, 6.5 Hz, 6.5 Hz), 3.27-3.42 (3H, m), 3.50-3.86 (6H, m), 3.88-4.03 (3H, m), 4.03-4.13 (1H, m), 4.24 (1H, dd, J=15.6 Hz, 5.5 Hz), 4.55 (1H, dd, J=15.4 Hz, 7.2 Hz), 4.87 (1H, m), 5.13-5.28 (2H, m), 5.31 (1H, dd, J=4.5 Hz, 4.5 Hz), 5.74 (1H, m), 5.89 (1H, m), 6.05 (2H, d, J=10.2 Hz), 6.20 (1H, d, J=8.2 Hz), 6.62 (1H, d, J=7.0 Hz), 6.83 (1H, dd, J=6.2 Hz, 6.2 Hz), 7.22-7.32 (3H, m), 7.32-7.44 (3H, m)

ESI-MS (m/z): 758.67 [M+H]$^+$.

Production Example 12-1-1

5-(Benzyloxy)-2-bromo-1,3-difluorobenzene

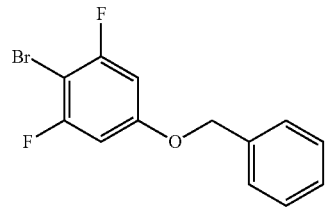 [SMILES: Fc1cc(OCc2ccccc2)cc(F)c1Br]

A crude product (2.68 g) of the title compound was produced from a commercially available product of 4-bromo-3,5-difluorophenol (1.00 g, 4.79 mmol) employing the similar procedure as in Production Example 1-2-4. The product was used in the subsequent reaction without further purification.

Production Example 12-1-2

5-(Benzyloxy)-1,3-difluoro-2-iodobenzene

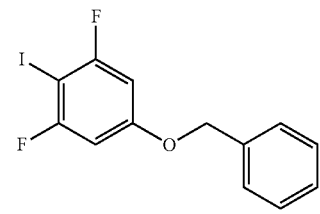 [SMILES: Fc1cc(OCc2ccccc2)cc(F)c1I]

A crude product (1.66 g) of the title compound was produced from 5-(benzyloxy)-2-bromo-1,3-difluorobenzene (1.43 g) described in Production Example 12-1-1 employing the similar procedure as in Production Example 1-2-5. The product was used in the subsequent reaction without further purification.

Production Example 12-1-3

Methyl(2S)-3-(4-(benzyloxy)-2,6-difluorophenyl)-2-((((9H-fluoren-9-ylmethoxy)carbonyl)amino)propanoate

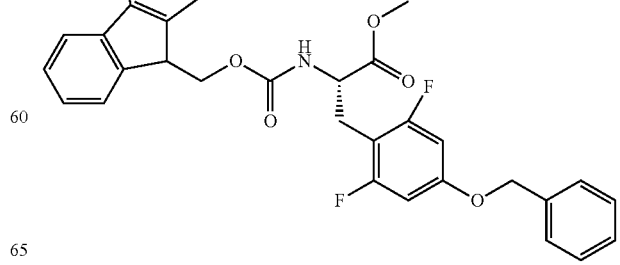

The title compound (264 mg, yield: 22%) was produced from 5-(benzyloxy)-1,3-difluoro-2-iodobenzene (844 mg, 2.44 mmol) described in Production Example 12-1-2 and methyl(2R)-2-(((9H-fluoren-9-ylmethoxy)carbonyl)amino)-3-iodopropanoate (1.15 g, 2.22 mmol) described in Production Example 1-2-3 employing the similar procedure as in Production Example 1-2-6.

ESI-MS (m/z): 545.2 [M+H]⁺.

Production Example 12-1-4

(2S)-3-(4-(Benzyloxy)-2,6-difluorophenyl)-2-(((9H-fluoren-9-ylmethoxy)carbonyl)amino)propanoic acid

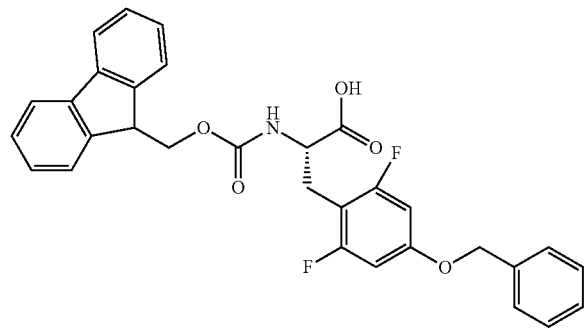 [SMILES: O=C(N[C@@H](Cc1c(F)cc(OCc2ccccc2)cc1F)C(=O)O)OCC1c2ccccc2-c2ccccc21]

The title compound (80.0 mg, yield: 31%) was produced from methyl(2S)-3-(4-(benzyloxy)-2,6-difluorophenyl)-2-(((9H-fluoren-9-ylmethoxy)carbonyl)amino)propanoate (264 mg, 0.486 mmol) described in Production Example 12-1-3 employing the similar procedure as in Production Example 1-2-7.

ESI-MS (m/z): 531.3 [M+H]⁺.

Production Example 12-2-1

(2S)-2-Amino-3-(4-(benzyloxy)-2,6-difluorophenyl)-N-(2,2-diethoxyethyl)-N-((6-fluoropyridin-2-yl)methyl)propanamide

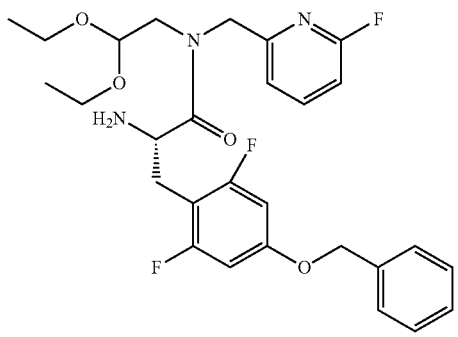 [SMILES: CCOC(CN(Cc1cccc(F)n1)C(=O)[C@@H](N)Cc1c(F)cc(OCc2ccccc2)cc1F)OCC]

The title compound (1.64 g, yield: 91%) was produced from (2,2-diethoxyethyl)((6-fluoropyridin-2-yl)methyl)amine (821 mg, 3.39 mmol) described in Production Example 1-1-1 and (2S)-3-(4-(benzyloxy)-2,6-difluorophenyl)-2-(((9H-fluoren-9-ylmethoxy)carbonyl)amino)propanoic acid (1.67 g, 3.39 mmol) described in Production Example 12-1-4 employing the similar procedures as in Production Example 1-1-2 and Production Example 1-1-3.

ESI-MS (m/z): 532.46 [M+H]⁺.

Production Example 12-2-2

(2S)-2-(2-(((Benzylcarbamoyl)amino)(prop-2-en-1-yl)amino)acetamido)-3-(4-(benzyloxy)-2,6-difluorophenyl)-N-(2,2-diethoxyethyl)-N-((6-fluoropyridin-2-yl)methyl)propanamide

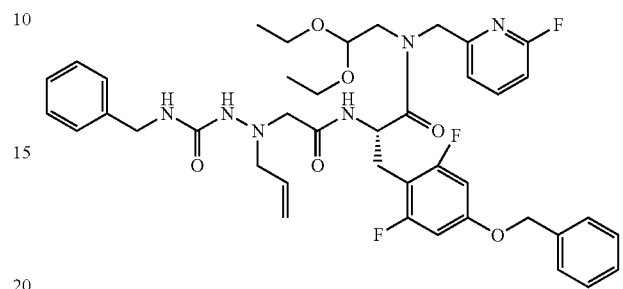

The title compound (1.51 g, yield: 63%) was produced from (2S)-2-amino-3-(4-(benzyloxy)-2,6-difluorophenyl)-N-(2,2-diethoxyethyl)-N-((6-fluoropyridin-2-yl)methyl)propanamide (1.64 g, 3.08 mmol) described in Production Example 12-2-1 employing the similar procedure as in Production Example 1-1-4.

ESI-MS (m/z): 777.61 [M+H]⁺.

Production Example 12-2-3

(6S,9aS)-N-Benzyl-6-((4-(benzyloxy)-2,6-difluorophenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide

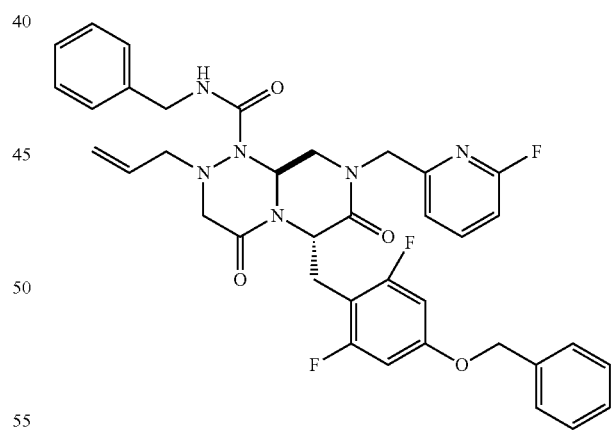

The title compound (1.08 g, yield: 81%) was produced from (2S)-2-(2-(((benzylcarbamoyl)amino)(prop-2-en-1-yl)amino)acetamido)-3-(4-(benzyloxy)-2,6-difluorophenyl)-N-(2,2-diethoxyethyl)-N-((6-fluoropyridin-2-yl)methyl)propanamide (1.51 g, 1.95 mmol) described in Production Example 12-2-2 employing the similar procedure as in Production Example 1-1-5.

¹H-NMR Spectrum (400 MHz, CDCl₃) δ(ppm): 3.20-3.30 (2H, m), 3.35-3.50 (2H, m), 3.51-3.60 (2H, m), 3.61-3.69 (1H, m), 3.93 (1H, dd, J=11.2 Hz, 11.6 Hz), 4.36-4.56 (3H, m), 4.76 (1H, d, J=15.0 Hz), 4.94 (2H, d, J=2.4 Hz), 5.17-5.26 (2H, m), 5.45 (1H, dd, 1=4.9 Hz, 9.0 Hz), 5.64-5.76 (1H, m), 6.16 (1H, dd, J=4.0 Hz, 11.0 Hz), 6.45 (2H, d, J=9.5 Hz), 6.76 (1H, dd, J=6.0 Hz, 6.0 Hz), 6.85 (1H, dd, J=2.4 Hz, 8.2 Hz), 7.20 (1H, dd, J=2.4 Hz, 7.5 Hz), 7.24-7.33 (3H, m), 7.33-7.42 (7H, m), 7.77 (1H, dd, J=8.0 Hz, 8.0 Hz).

Production Example 12-2-4

(6S,9aS)-N-Benzyl-6-((2,6-difluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide

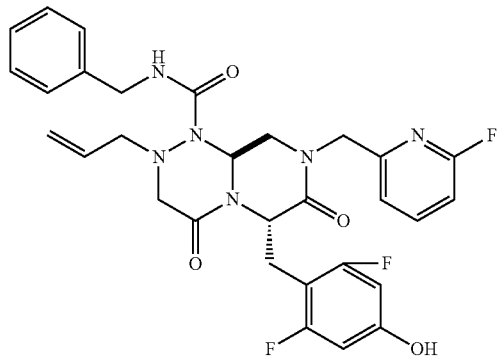

The title compound (755 mg, yield: 80%) was produced from (6S,9aS)-N-benzyl-6-((4-(benzyloxy)-2,6-difluorophenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (1.08 g, 1.58 mmol) described in Production Example 12-2-3 employing the similar procedure as in Production Example 1-1-6.

¹H-NMR Spectrum (400 MHz, CDCl₃) δ(ppm): 3.20-3.30 (1H, m), 3.40-3.70 (5H, m), 3.97 (1H, dd, J=10.4 Hz, 12.0 Hz), 4.35-4.55 (3H, m), 4.84 (1H, d, J=14.9 Hz), 5.18-5.28 (2H, m), 5.45 (1H, dd, J=4.6 Hz, 9.0 Hz), 5.65-5.75 (1H, m), 6.14-6.26 (3H, m), 6.76 (1H, dd, J=6.0 Hz, 6.4 Hz), 6.82-6.88 (1H, m), 7.18-7.24 (1H, m), 7.24-7.34 (3H, m), 7.34-7.42 (2H, m), 7.76-7.90 (2H, m).

Example 13

(6S,9aS)-N-Benzyl-6-((2,6-difluoro-4-hydroxyphenyl)methyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

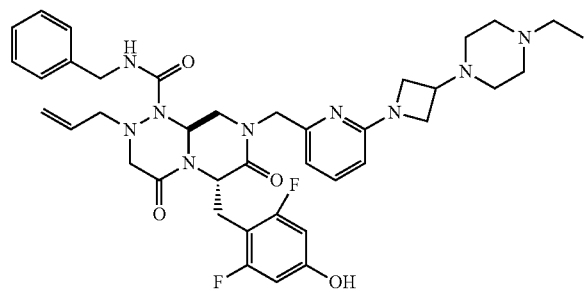

¹H-NMR Spectrum (400 MHz, CDCl₃) δ(ppm): 1.01 (3H, t, J=7.1 Hz), 2.25-2.70 (10H, m), 3.18-3.28 (1H, m), 3.35-3.50 (3H, m), 3.50-3.80 (6H, m), 3.85-3.92 (1H, m), 3.92-4.05 (2H, m), 4.18-4.28 (2H, m), 4.54 (1H, dd, J=6.8 Hz, 15.9 Hz), 5.01 (1H, d, J=13.9 Hz), 5.20-5.30 (3H, m), 5.70-5.80 (2, m), 6.00 (2H, d, J=9.5 Hz), 6.22 (1H, d, J=8.1 Hz), 6.67 (1H, d, J=7.3 Hz), 6.85 (114, dd, J=5.2 Hz, 7.2 Hz), 7.20-7.32 (3H, m), 7.34-7.46 (3H, m).

ESI-MS (m/z): 744.60 [M+H]⁺.

Example 14

(6S,9aS)-N-Benzyl-6-((2,6-difluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

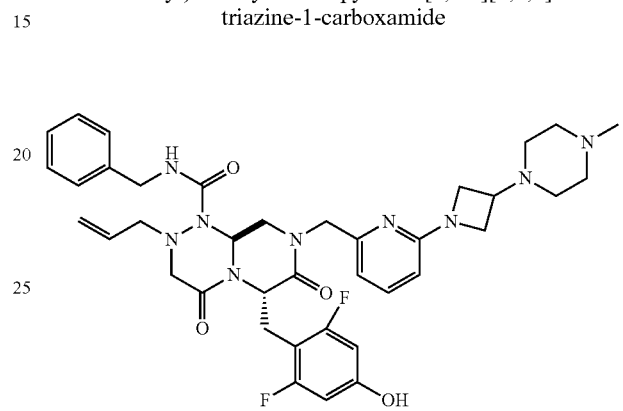

¹H-NMR Spectrum (400 MHz, CDCl₃) δ(ppm): 2.18-2.30 (5H, m), 2.30-2.60 (6H, m), 3.18-3.25 (1H, m), 3.30-3.45 (3H, m), 3.50-3.80 (6H, m), 3.85-3.95 (1H, m), 3.95-4.03 (2H, m), 4.18-4.28 (2H, m), 4.51 (1H, dd, J=7.1 Hz, 15.9 Hz), 5.06 (1H, d, J=13.9 Hz), 5.20-5.30 (3H, m), 5.70-5.80 (2H, m), 6.00 (2H, d, J=9.9 Hz), 6.22 (1H, d, J=8.4 Hz), 6.67 (1H, d, J=7.3 Hz), 6.84 (1H, dd, J=6.0 Hz, 6.4 Hz), 7.20-7.32 (3H, m), 7.34-7.46 (3H, m).

ESI-MS (m/z): 730.62 [M+H]⁺.

Example 15

(6S,9aS)-N-Benzyl-8-((6-(3-((2S)-2,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

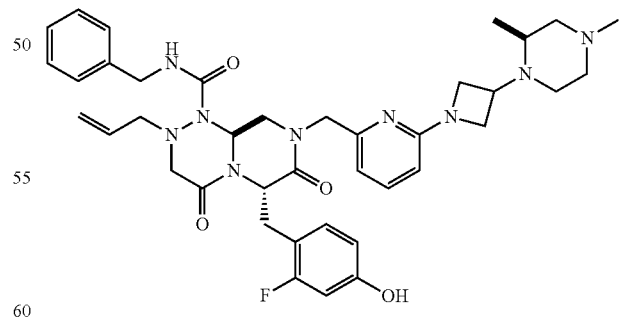

¹H-NMR Spectrum (400 MHz, CDCl₃) δ(ppm): 105 (3H, d, J=6.0 Hz), 1.95-2.10 (2H, m), 2.10-2.35 (5H, m), 2.40-2.65 (1H, m), 3.10-3.20 (1H, m), 3.30-3.50 (3H, m), 3.50-3.75 (8H, m), 3.88 (1H, dd, J=7.2 Hz, 9.6 Hz), 4.05 (1H, dd, J=6.8 Hz, 6.8 Hz), 4.13 (1H, dd, J=6.8 Hz, 7.2 Hz), 4.18-4.25 (2H, m), 4.49 (1H, dd, J=7.0 Hz, 15.7 Hz), 4.94 (1H, d, J=13.5 Hz), 5.18-5.30 (3H, m), 5.56 (1H, dd, J=4.2 Hz, 10.4 Hz), 5.70-

5.80 (1H, m), 5.90 (1H, dd, J=2.4 Hz, 8.2 Hz), 6.27 (1H, d, J=8.1 Hz), 6.40-6.48 (2H, m), 6.74 (1H, d, J=7.2 Hz), 6.81 (1H, dd, J=5.6 Hz, 7.2 Hz), 7.22 (2H, d, J=7.2 Hz), 7.24-7.32 (1H, m), 7.38 (2H, dd, J=7.2 Hz, 8.0 Hz), 7.45 (1H, dd, J=8.0 Hz, 8.0 Hz).

ESI-MS (m/z): 726.67 [M+H]+.

Example 16

(6S,9aS)-N-Benzyl-6-((2,6-difluoro-4-hydroxyphenyl)methyl)-8-((6-(3-((3S)-3,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

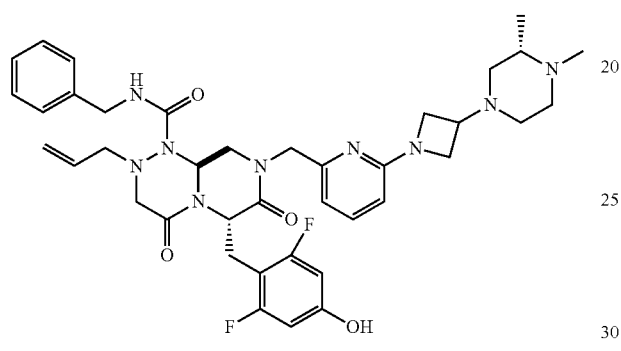

1H-NMR Spectrum (400 MHz, CDCl3) δ(ppm): 1.04 (3H, d, J=6.2 Hz), 1.60-1.85 (2H, m), 1.90-2.00 (1H, m), 2.15-2.30 (6H, m), 2.74 (1H, d, J=11.7 Hz), 3.10-3.20 (1H, m), 3.35-3.50 (3H, m), 3.50-3.80 (6H, m), 3.89 (1H, dd, J=7.1 Hz, 10.1 Hz), 3.98 (2H, dd, J=3.1 Hz, 6.4 Hz), 4.24 (2H, dd, J=4.6 Hz, 14.8 Hz), 4.52 (1H, dd, J=7.1 Hz, 16.3 Hz), 5.00 (1H, d, J=13.9 Hz), 5.20-5.30 (3H, m), 5.75-5.81 (2H, m), 5.99 (2H, d, J=9.5 Hz), 6.22 (1H, d, J=8.4 Hz), 6.67 (1H, d, J=7.3 Hz), 6.85 (1H, dd, J=6.0 Hz, 6.4 Hz), 7.20-7.32 (3H, m), 7.34-7.46 (3H, m).

ESI-MS (m/z): 744.69 [M+H]+.

Example 17

(6S,9aS)-N-Benzyl-6-((2,6-difluoro-4-hydroxyphenyl)methyl)-8-((6-(3-((2S)-2,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

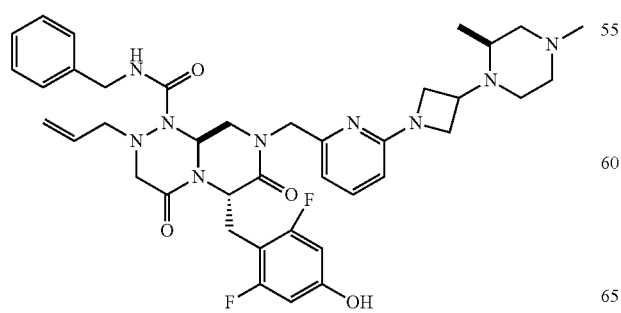

1H-NMR Spectrum (400 MHz, CDCl3) δ(ppm): 1.05 (3H, d, J=6.6 Hz), 1.50-1.90 (2H, m), 1.93-2.05 (1H, m), 2.10-2.25 (5H, m), 2.50-2.65 (2H, m), 3.30-3.50 (4H, m), 3.50-3.78 (6H, m), 3.91 (1H, dd, J=7.1 Hz, 9.7 Hz), 4.02-4.12 (2H, m), 4.18-4.30 (2H, m), 4.52 (1H, dd, J=7.3 Hz, 15.7 Hz), 5.00 (1H, d, J=13.5 Hz), 5.20-5.30 (3H, m), 5.70-5.81 (2H, m), 6.03 (2H, d, J=9.5 Hz), 6.25 (1H, d, J=8.4 Hz), 6.71 (1H, d, J=7.3 Hz), 6.83 (1H, dd, J=6.4 Hz, 6.4 Hz), 7.20-7.32 (3H, m), 7.34-7.48 (3H, m).

ESI-MS (m/z): 744.65 [M+H]+.

Example 18

(6S,9aS)-N-Benzyl-8-((6-(3-((3S)-4-ethyl-3-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

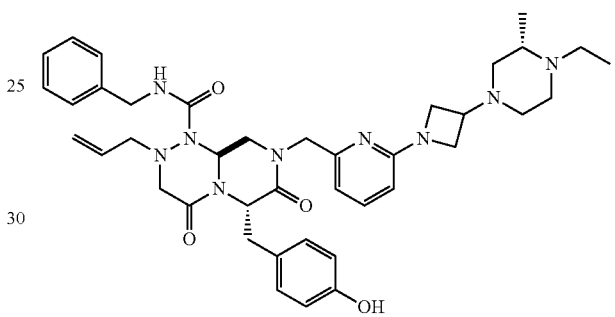

1H-NMR Spectrum (400 MHz, CDCl3) δ(ppm): 0.948 (3H, t, J=6.8 Hz), 1.05 (3H, d, J=6.4 Hz), 1.70-2.00 (2H, m), 2.27-2.60 (4H, m), 2.70-2.90 (2H, m), 3.05-3.22 (2H, m), 3.30-3.70 (8H, m), 3.70-3.90 (2H, m), 4.00-4.10 (2H, m), 4.19 (2H, d, J=10.4 Hz), 4.35-4.50 (1H, m), 4.99 (1H, d, J=13.6 Hz), 5.03-5.12 (1H, m), 5.13-5.30 (3H, m), 5.68-5.80 (1H, m), 6.29 (1H, d, J=8.8 Hz), 6.39 (2H, d, J=8.0 Hz), 6.56 (2H, d, J=7.6 Hz), 6.68-6.78 (2H, m), 7.14-7.32 (3H, m), 7.32-7.42 (2H, m), 7.44-7.50 (1H, m).

ESI-MS (m/z): 722.72 [M+H]+.

Production Example 18-1

Tert-Butyl(2S)-4-(1-(diphenylmethyl)azetidin-3-yl)-2-methylpiperazine-1-carboxylate

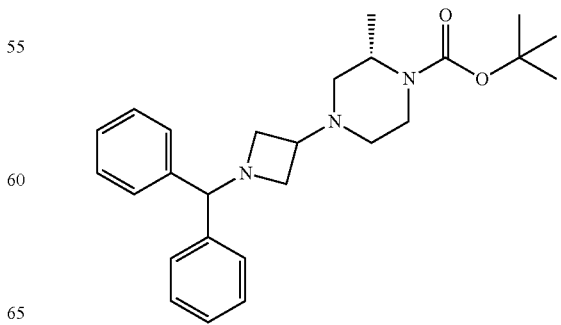

The title compound (451 mg, 85%) was produced from a commercially available product of 1-(diphenylmethyl)azetidin-3-one (300 mg, 1.26 mmol) and a commercially available product of tert-butyl(2S)-2-methylpiperazine-1-carboxylate (304 mg, 1.51 mmol) employing the similar procedure as in Production Example 6-1.

¹H-NMR Spectrum (400 MHz, CDCl₃) δ(ppm): 1.20 (3H, d, J=6.8 Hz), 1.44 (9H, s), 1.73-1.82 (1H, m), 1.96 (1H, dd, J=4.0 Hz, 11.0 Hz), 2.40 (1H, d, J=11.0 Hz), 2.56 (1H, d, J=11.0 Hz), 2.78 (1H, dd, J=6.4 Hz, 7.6 Hz), 2.83-2.95 (2H, m), 3.01 (1H, td, J=3.3 Hz, 12.8 Hz), 3.35-3.43 (2H, m), 3.78 (1H, d, J=12.8 Hz), 4.13-4.22 (1H, m), 4.38 (1H, s), 7.15-7.21 (2H, m), 7.23-7.30 (4H, m), 7.38-7.43 (4H, m).

Production Example 18-2

(2S)-4-(1-(Diphenylmethyl)azetidin-3-yl)-1-ethyl-2-methylpiperazine

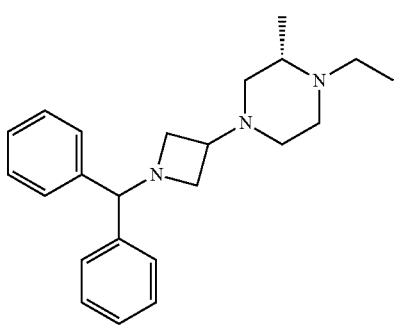 [SMILES: CCN1CCN(C2CN(C(c3ccccc3)c3ccccc3)C2)C[C@@H]1C]

The title compound (381 mg, yield: quantitative) was produced from tert-butyl(2S)-4-(1-(diphenylmethyl)azetidin-3-yl)-2-methylpiperazine-1-carboxylate (451 mg, 1.07 mmol) described in Production Example 18-1 and acetaldehyde (180 μL, 3.21 mmol) employing the similar procedure as in Production Example 4-2.

¹H-NMR Spectrum (400 MHz, CDCl₃) δ(ppm): 0.95-1.05 (6H, m), 1.73 (1H, dd, J=10.4 Hz, 10.4 Hz), 1.98-2.10 (1H, m), 2.30-2.45 (3H, m), 2.53 (1H, d, J=11.0 Hz), 2.64 (1H, d, J=11.0 Hz), 2.78-2.98 (5H, m), 3.39 (2H, dd, J=5.6 Hz, 7.2 Hz), 4.42 (1H, s), 7.18 (2H, td, J=0.80 Hz, 8.0 Hz), 7.23-7.29 (4H, m), 7.64 (4H, dd, J=1.6 Hz, 8.0 Hz).

Production Example 18-3

(2S)-4-(azetidin-3-yl)-1-ethyl-2-methylpiperazine

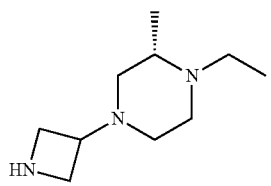

The title compound was produced in the form of a mixture (288 mg) with benzylbenzene from (2S)-4-(1-(diphenylmethyl)azetidin-3-yl)-1-ethyl-2-methylpiperazine (381 mg, 1.09 mmol) described in Production Example 18-2 employing the similar procedure as in Production Example 6-3. The product was used in the subsequent reaction without further purification.

Example 19

(6S,9aS)-N-Benzyl-8-((6-3-((3R)-4-ethyl-3-methylpiperazin-1-yl)azetidin-1-yl)pyridin-2-yl)methyl-6-((4-hydroxyphenyl)methyl)-4,7-dioxo-2-(prop-2-en-1-yl)-octahydro-1H-pyrazino[2,1-c][1,2,4]triazine-1-carboxamide

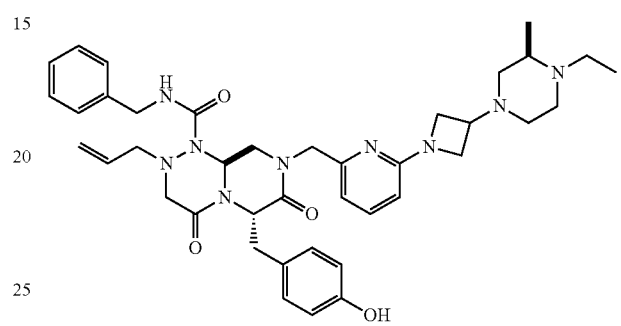

¹H-NMR Spectrum (400 MHz, CDCl₃) δ(ppm): 0.91 (3H, d, J=5.9 Hz), 1.03 (3H, t, J=6.8 Hz), 1.50-1.95 (1H, m), 2.13-2.25 (1H, m), 2.35-2.55 (2H, m), 2.60-2.75 (1H, m), 2.80-2.95 (3H, m), 3.05-3.25 (3H, m), 3.35-3.48 (2H, m), 3.50-3.60 (5H, m), 3.75 (1H, dd, J=6.4 Hz, 9.2 Hz), 3.89 (1H, dd, J=7.0 Hz, 9.5 Hz), 4.03 (2H, d, J=6.6 Hz), 4.19 (1H, dd, J=4.2 Hz, 11.2 Hz), 4.25-4.42 (2H, m), 4.98 (1H, d, J=13.5 Hz), 5.15-5.30 (4H, m), 5.65-5.78 (1H, m), 6.28 (1H, d, J=8.4 Hz), 6.39 (2H, d, J=8.4 Hz), 6.59 (2H, d, J=8.4 Hz), 6.68-6.76 (2H, m), 7.20-7.33 (3H, m), 7.37 (2H, dd, J=7.2 Hz, 8.0 Hz), 7.46 (1H, dd, J=7.6 Hz, 8.0 Hz).

ESI-MS (m/z): 722.68 [M+H]⁺.

Production Example 19-1

Tert-Butyl(2R)-4-(1-(diphenylmethyl)azetidin-3-yl)-2-methylpiperazine-1-carboxylate

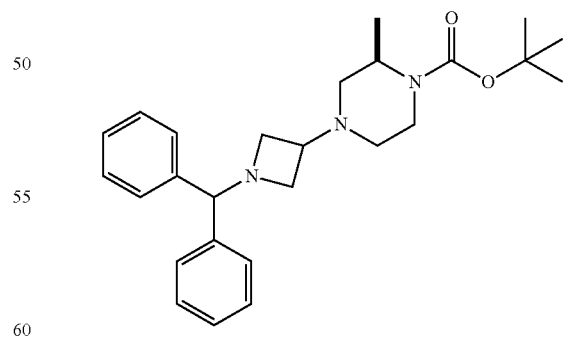

The title compound (491 mg, yield: 92%) was produced from a commercially available product of 1-(diphenylmethyl)azetidin-3-one (300 mg, 1.26 mmol) and a commercially available product of tert-butyl(2R)-2-methylpiperazine-1-carboxylate (304 mg, 1.51 mmol) employing the similar procedure as in Production Example 6-1, ¹H-NMR Spectrum (400 MHz, CDCl₃) δ(ppm): 1.20 (3H, d, J=6.8 Hz), 1.44 (9H, s), 1.77 (1H, td, J=3.5 Hz, 11.6 Hz), 1.96 (1H, dd, J=4.0 Hz, 11.3 Hz), 2.40 (1H, d, J=11.3 Hz), 2.56 (1H, d, J=11.0 Hz), 2.78 (1H, dd, J=6.4 Hz, 6.8 Hz), 2.83-2.95 (2H, m), 3.01 (1H, td, J=2.9 Hz, 12.6 Hz), 3.35-3.45 (2H, m), 3.78 (1H, d, J=13.5 Hz), 4.10-4.22 (1H, m), 4.38 (1H, s), 7.18 (2H, dd, J=7.2 Hz, 7.2 Hz), 7.23-7.30 (4H, m), 7.41 (4H, d, J=7.2 Hz).

Production Example 19-2

(2R)-4-(1-(Diphenylmethyl)azetidin-3-yl)-1-ethyl-2-methylpiperazine

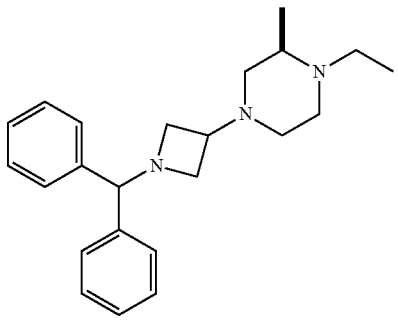 [SMILES: CCN1CCN(C2CN(C(c3ccccc3)c3ccccc3)C2)C[C@H]1C]

The title compound (410 mg, yield: quantitative) was produced from tert-butyl(2R)-4-(1-(diphenylmethyl)azetidin-3-yl)-2-methylpiperazine-1-carboxylate (491 mg, 1.16 mmol) described in Production Example 19-1 and acetaldehyde (196 μL, 3.48 mmol) employing the similar procedure as in Production Example 4-2.

¹H-NMR Spectrum (400 MHz, CDCl₃) δ(ppm): 0.95-1.05 (6H, m), 1.73 (1H, dd, J=10.0 Hz, 10.4 Hz), 1.98-2.10 (1H, m), 2.28-2.48 (3H, m), 2.53 (1H, d, J=10.3 Hz), 2.64 (1H, d, J=10.3 Hz), 2.78-3.00 (5H, m), 3.39 (2H, dd, J=5.6 Hz, 6.8 Hz), 4.42 (1H, s), 7.18 (2H, dd, J=6.8 Hz, 7.2 Hz), 7.23-7.29 (4H, m), 7.37-7.42 (4H, m).

Production Example 19-3

(2R)-4-(Azetidin-3-yl)-1-ethyl-2-methylpiperazine

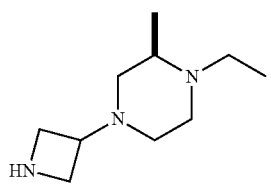

The title compound was produced in the form of a mixture (343 mg) with benzylbenzene from (2R)-4-(1-(diphenylmethyl)azetidin-3-yl)-1-ethyl-2-methylpiperazine (410 mg, 1.17 mmol) described in Production Example 19-2 employing the similar procedure as in Production Example 6-3. The product was used in the subsequent reaction without further purification.

Example 20

(6S,9aS)-N-Benzyl-8-((6-(3-((3S)-4-ethyl-3-methylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

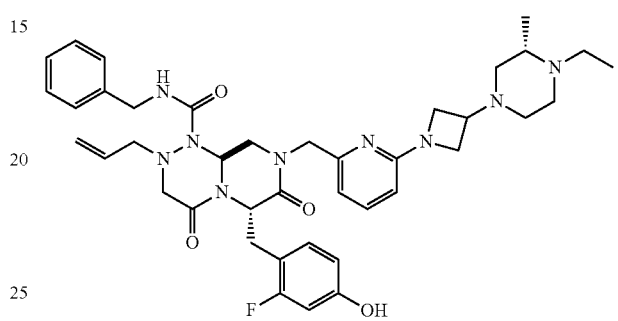

¹H-NMR Spectrum (400 MHz, CDCl₃) δ(ppm): 0.926 (3H, t, J=7.2 Hz), 1.04 (3H d, J=5.9 Hz), 1.70-1.85 (1H, m), 1.88-1.98 (1H, m), 2.25-2.40 (3H, m), 2.45-2.55 (1H, m), 2.70-2.85 (2H, m), 3.10-3.20 (2H, m), 3.38-3.75 (9H, m), 3.80-3.90 (1H, m), 3.95-4.05 (2H, m), 4.15-4.25 (2H, m), 4.53 (1H, dd, J=7.1 Hz, 15.9 Hz), 4.95 (1H, d, J=13.5 Hz), 5.20-5.30 (3H, m), 5.50-5.60 (1H, m), 5.65-5.80 (1H, m), 5.80-5.90 (1H, m), 6.24 (1H, d, J=8.4 Hz), 6.40 (1H, dd, J=2.8 Hz, 11.6 Hz), 6.47 (1H, dd, J=8.8 Hz, 8.8 Hz), 6.69 (1H, d, J=7.2 Hz), 6.84 (1H, dd, J=5.6 Hz, 6.4 Hz), 7.20-7.32 (3H, m), 7.34-7.46 (3H, m).
ESI-MS (m/z): 740.70 [M+H]⁺.

Example 21

(6S,9aS)-N-Benzyl-8-((6-(3-((3R)-4-ethyl-3-methylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

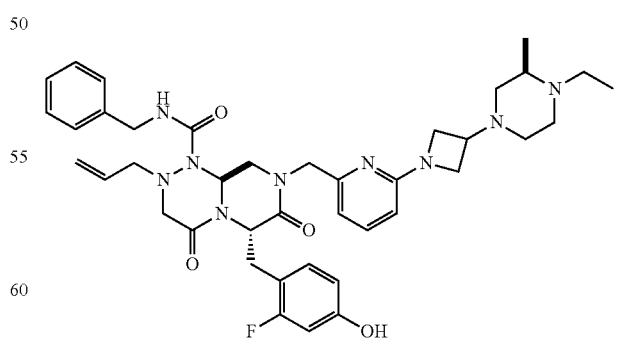

¹H-NMR Spectrum (400 MHz, CDCl₃) δ(ppm): 0.89 (3H, d, J=8.0 Hz), 1.03 (3H, t, J=7.3 Hz), 1.50-1.90 (1H, m), 2.15-2.25 (1H, m), 2.35-2.50 (2H, m), 2.60-2.70 (1H, m), 2.80-2.95 (3H, m), 3.10-3.30 (3H, m), 3.35-3.75 (8H, m), 3.88 (1H, dd, J=7.1 Hz, 10.1 Hz), 4.00 (2H-1, dd, J=3.8 Hz, 6.4 Hz), 4.21 (1H, dd, J=4.4 Hz, 11.0 Hz), 4.32 (1H, dd, J=5.3 Hz, 15.2 Hz), 4.47 (1H, dd, J=6.6 Hz, 15.4 Hz), 4.95 (1H, d, J=13, 9 Hz), 5.20-5.30 (3H, m), 5.62 (1H, dd, J=3.5 Hz, 7.5 Hz), 5.65-5.80 (1H, m), 5.85-5.90 (1H, m), 6.24 (1H, d, J=8.1 Hz), 6.39 (1H, dd, J=2.4 Hz, 11.5 Hz), 6.51 (1H, dd, J=8.4 Hz, 8.8 Hz), 6.67 (1H, d, J=7.0 Hz), 6.82 (1H, dd, J=6.0 Hz, 6.4 Hz), 7.22-7.32 (3H, m), 7.37 (2H, dd, J=6.8 Hz, 7.2 Hz), 7.43 (1H, dd, J=7.6 Hz, 8.0 Hz).

ESI-MS (m/z): 740.66 [M+H]⁺.

Example 22

(6S,9aS)-N-Benzyl-6-((2,6-difluoro-4-hydroxyphenyl)methyl)-8-((6-(3-((3S)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

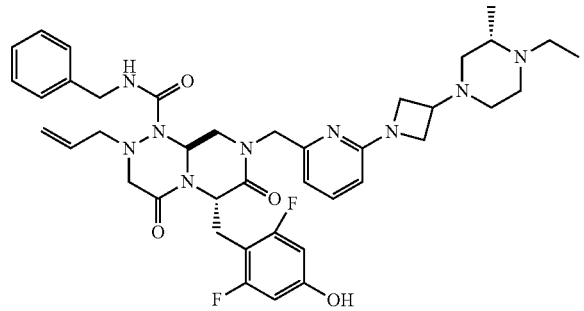

¹H-NMR Spectrum (400 MHz, CDCl₃) δ(ppm): 0.93 (3H, t, J=6.8 Hz), 1.05 (3H, d, J=6.2 Hz), 1.70-2.10 (2H, m), 2.25-2.40 (3H, m), 2.45-2.55 (1H, m), 2.70-2.85 (2H, m), 3.15-3.30 (1H, m), 3.30-3.82 (11H, m), 3.85-3.95 (1H, m), 3.95-4.05 (2H, m), 4.15-4.25 (2H, m), 4.55 (1H, dd, J=7.0 Hz, 15.4 Hz), 5.00 (1H, d, J=13.9 Hz), 5.20-5.30 (3H, m), 5.70-5.82 (2H, m), 6.00 (2H-1, d, J=9.9 Hz), 6.22 (1H, d, J=8.1 Hz), 6.67 (1H, d, J=7.3 Hz), 6.86 (1H, dd, J=6.0 Hz, 6.8 Hz), 7.20-7.26 (1H, m), 7.26-7.32 (1H, m), 7.35-7.46 (3H, m).

ESI-MS (m/z): 758.76 [M+H]⁺.

Example 23

(6S,9aS)-N-Benzyl-6-((2,6-difluoro-4-hydroxyphenyl)methyl)-8-((6-(3-((3R)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

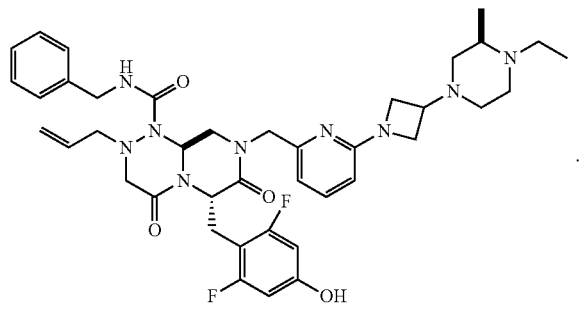

¹H-NMR Spectrum (400 MHz, CDCl₃) δ(ppm): 0.893 (3H, d, J=6.4 Hz), 1.02 (3H, t, J=6.8 Hz), 1.50-1.90 (1H, m), 2.15-2.40 (1H, m), 2.35-2.50 (2H, m), 2.55-2.68 (1H, m), 2.80-2.95 (3H, m), 3.15-3.25 (2H, m), 3.30-3.80 (10H, m), 3.90-4.02 (3H, m), 4.21 (1H, dd, J=4.2 Hz, 11.2 Hz), 4.32 (1H, dd, J=5.8 Hz, 15.2 Hz), 4.50 (1H, dd, J=6.8 Hz, 14.8 Hz), 4.99 (1H, d, J=13.9 Hz), 5.20-5.30 (3H, m), 5.66-5.84 (2H, m), 6.02 (2H, d, J=9.9 Hz), 6.22 (1H, d, J=8.1 Hz), 6.65 (1H, d, J=7.3 Hz), 6.83 (1H, dd, J=5.6 Hz, 6.4 Hz), 7.22-7.33 (2H, m), 7.35-7.46 (3H, m).

ESI-MS (m/z): 758.72 [M+H]⁺.

Example 24

(6S,9aS)-N-Benzyl-8-((6-(3-((3R)-3,4-dimethylpiperazin-1-yl)azetidine-1-yl)-5-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

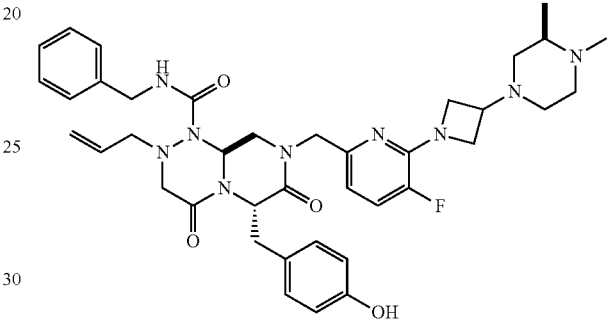

The title compound (47.0 mg, yield: 24%) was produced from (2S)-2-(2-((benzylcarbamoyl)amino)(prop-2-en-1-yl)amino)acetamido)-3-(4-(tert-butoxy)phenyl)-N-(2,2-diethoxyethyl)-N-((6-(3-((3R)-3,4-dimethylpiperazin-1-yl)azetidin-1-yl)-5-fluoropyridin-2-yl)methyl)propanamide (241 mg, 0.276 mmol) described in Production Example 24-1-6 employing the similar procedure as in Production Example 2-4.

¹H-NMR Spectrum (400 MHz, CDCl₃) δ(ppm): 0.91 (3H, d, J=6.2 Hz), 1.65-1.76 (1H, m), 2.10-2.21 (2H, m), 2.30 (3H, s), 2.38-2.56 (2H, m), 2.77-2.91 (2H, m), 3.12 (1H, dd, J=4.7 Hz, 13.9 Hz), 3.17-3.24 (2H, m), 3.39-3.70 (8H, m), 3.74-3.81 (1H, m), 3.84-3.91 (1H, m), 4.07 (1H, dd, J=4.4 Hz, 11.2 Hz), 4.26-4.44 (3H, m), 4.94 (1H, d, J=13.8 Hz), 5.17-5.27 (3H, m), 5.64-5.77 (1H, m), 6.47-6.53 (2H, m), 6.59-6.66 (3H, m), 6.69-6.74 (1H, m), 7.11 (1H, dd, J=7.8 Hz, 12.1 Hz), 7.21-7.42 (5H, m).

ESI-MS (m/z): 726.59 [M+H]⁺.

Production Example 24-1-1

2-Chloro-6-(diethoxymethyl)-3-fluoropyridine

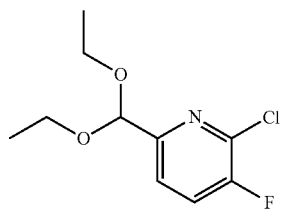

To a mixed solution of a commercially available product of 6-chloro-5-fluoropyridine-2-carbaldehyde (820 mg, 5.14 mmol) and ethanol (10.0 mL) were added triethyl orthoformate (2.56 mL, 15.4 mmol) and pyridinium p-toluenesulfonate (64.6 mg, 0.257 mmol) at room temperature. The resultant mixture was stirred at 80° C. for 5 hours. The reaction mixture was concentrated under a reduced pressure, water was added to the residue, and the resultant solution was extracted with ethyl acetate two times. An organic layer was dried over anhydrous magnesium sulfate and then filtrated. The solvent was evaporated under a reduced pressure, to give a crude product (977 mg) of the title compound. The product was used in the subsequent reaction without further purification.

ESI-MS (m/z): 234.91 [M+H]+.

Production Example 24-1-2

(2R)-4-(1-(6-(Diethoxymethyl)-3-fluoropyridin-2-yl)azetidin-3-yl)-1,2-dimethylpiperazine

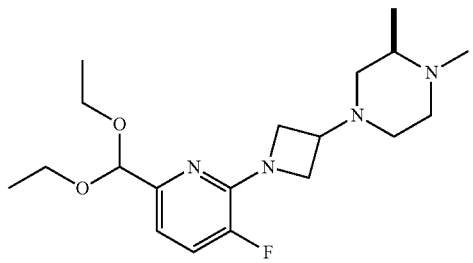 [SMILES: CCOC(OCC)c1ccc(F)c(N2CC(N3CCN(C)[C@H](C)C3)C2)n1]

A crude product (157 mg) of the title compound was produced from 2-chloro-6-(diethoxymethyl)-3-fluoropyridine (100 mg, 0.428 mmol) described in Production Example 24-1-1 and a crude product (229 mg) of (2R)-4-(azetidin-3-yl)-1,2-dimethylpiperazine described in Production Example 24-2-3 employing the similar procedure as in Production Example 7-1. The product was used in the subsequent reaction without further purification.

ESI-MS (m/z): 367.24 [M+H]+.

Production Example 24-1-3

6-(3-((3R)-3,4-Dimethylpiperazin-1-yl)azetidin-1-yl)-5-fluoropyridine-2-carbaldehyde

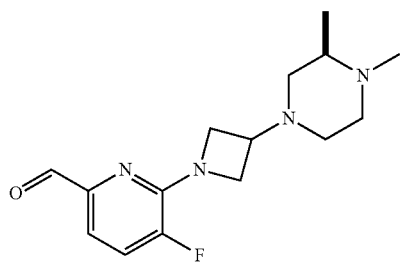 [SMILES: C[C@@H]1CN(C2CN(c3nc(C=O)ccc3F)C2)CCN1C]

To (2R)-4-(1-(6-(diethoxymethyl)-3-fluoropyridin-2-yl)azetidin-3-yl)-1,2-dimethylpiperazine (157 mg, 0.428 mmol) described in Production Example 24-1-2 was added formic acid (5.00 mL) at room temperature. The resultant mixture was stirred at room temperature for 30 minutes. The reaction mixture was concentrated under a reduced pressure, to give a crude product (125 mg) of the title compound. The product was used in the subsequent reaction without further purification.

ESI-MS (m/z): 293.13 [M+H]+.

Production Example 24-1-4

(2,2-Diethoxyethyl)((6-(3-((3R)-3,4-dimethylpiperazin-1-yl)azetidin-1-yl)-5-fluoropyridin-2-yl)methyl)amine

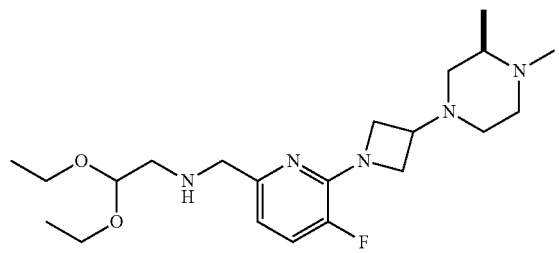 [SMILES: CCOC(CNCc1ccc(F)c(N2CC(N3CCN(C)[C@H](C)C3)C2)n1)OCC]

The title compound (176 mg, yield: quantitative) was produced from a crude product (125 mg) of 6-(3-((3R)-3,4-dimethylpiperazin-1-yl)azetidin-1-yl)-5-fluoropyridine-2-carbaldehyde described in Production Example 24-1-3 employing the similar procedure as in Production Example 1-1-1.

ESI-MS (m/z): 410.35 [M+H]+.

Production Example 24-1-5

(2S)-2-Amino-3-(4-(tert-butoxy)phenyl)-N-(2,2-diethoxyethyl)-N-((6-(3-((3R)-3,4-dimethylpiperazin-1-yl)azetidin-1-yl)-5-fluoropyridin-2-yl)methyl)propanamide

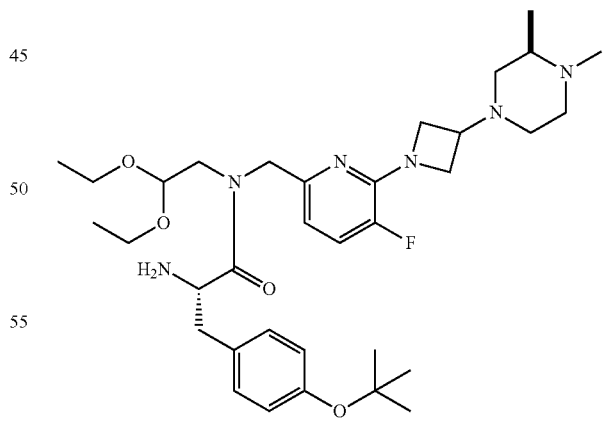

The title compound (206 mg, yield: 77%) was produced from (2,2-diethoxyethyl)((6-(3-((3R)-3,4-dimethylpiperazin-1-yl)azetidin-1-yl)-5-fluoropyridin-2-yl)methyl)amine (176 mg, 0.430 mmol) described in Production Example 24-1-4 employing the similar procedures as in Production Example 2-1 and Production Example 2-2.

ESI-MS (m/z): 629.57 [M+H]+.

Production Example 24-1-6

(2S)-2-(2-((Benzylcarbamoyl)amino)(prop-2-en-1-yl)amino)acetamido)-3-(4-(tert-butoxy)phenyl)-N-(2,2-diethoxyethyl)-N-((6-(3-((3R)-3,4-dimethylpiperazin-1-yl)azetidin-1-yl)-5-fluoropyridin-2-yl)methyl)propanamide

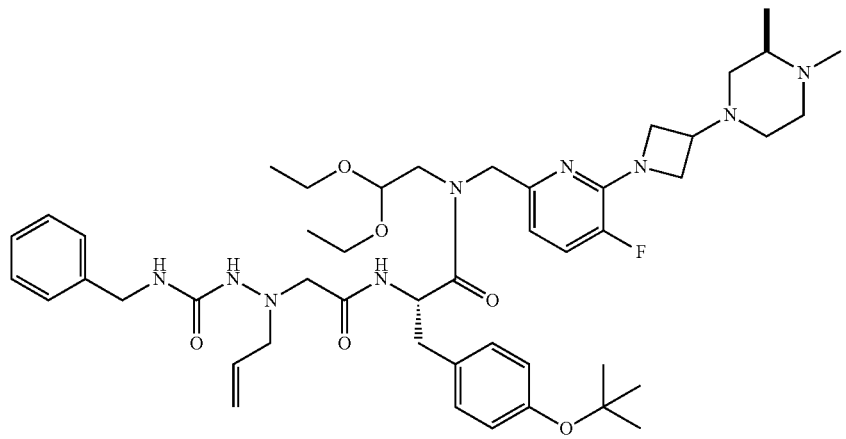 [SMILES: C=CCN(CC(=O)N[C@@H](Cc1ccc(OC(C)(C)C)cc1)C(=O)N(Cc1ccc(F)c(N2CC(N3CCN(C)[C@H](C)C3)C2)n1)CC(OCC)OCC)NC(=O)NCc1ccccc1]

The title compound (241 mg, yield: 82%) was produced from (2S)-2-amino-3-(4-(tert-butoxy)phenyl)-N-(2,2-diethoxyethyl)-N-((6-(3-((3R)-3,4-dimethylpiperazin-1-yl)azetidin-1-yl)-5-fluoropyridin-2-yl)methyl)propanamide (206 mg, 0.328 mmol) described in Production Example 24-1-5 employing the similar procedure as in Production Example 2-3.

ESI-MS (m/z): 874.84 [M+H]$^+$.

Production Example 24-2-1

Tert-Butyl(2R)-4-(1-((benzyloxy)carbonyl)azetidin-3-yl)-2-methylpiperazine-1-carboxylate

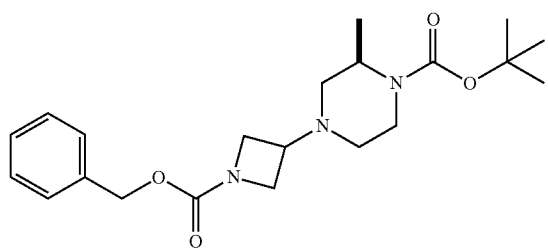 [SMILES: C[C@@H]1CN(C2CN(C(=O)OCc3ccccc3)C2)CCN1C(=O)OC(C)(C)C]

The title compound (610 mg, yield: 83%) was produced from a commercially available product of tert-butyl(2R)-2-methylpiperazine-1-carboxylate (451 mg, 2.25 mmol) and benzyl 3-oxoazetidine-1-carboxylate (500 mg, 1.88 mmol) employing the similar procedure as in Production Example 4-1.

ESI-MS (m/z): 390.35 [M+H]$^+$.

Production Example 24-2-2

Benzyl 3-((3R)-3,4-dimethylpiperazin-1-yl)azetidine-1-carboxylate

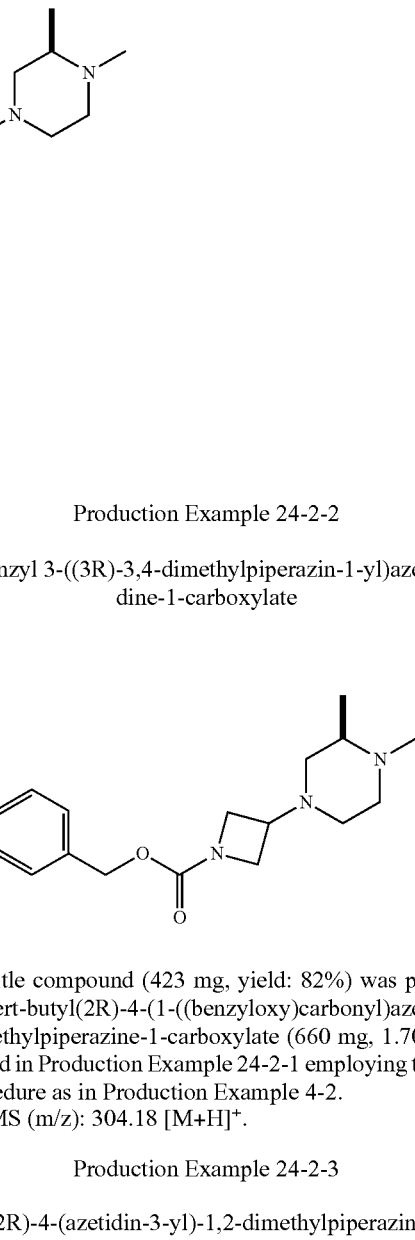

The title compound (423 mg, yield: 82%) was produced from tert-butyl(2R)-4-(1-((benzyloxy)carbonyl)azetidin-3-yl)-2-methylpiperazine-1-carboxylate (660 mg, 1.70 mmol) described in Production Example 24-2-1 employing the similar procedure as in Production Example 4-2.

ESI-MS (m/z): 304.18 [M+H]$^+$.

Production Example 24-2-3

(2R)-4-(azetidin-3-yl)-1,2-dimethylpiperazine

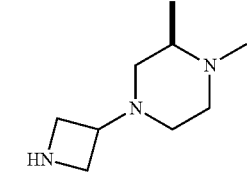

A crude product (236 mg) of the title compound was produced from benzyl 3-((3R)-3,4-dimethylpiperazin-1-yl)azetidine-1-carboxylate (423 mg, 1.39 mmol) described in Production Example 24-2-2 employing the similar procedure as in Production Example 4-3. The product was used in the subsequent reaction without further purification.
ESI-MS (m/z): 169.83 [M+H]+.

Reference Example 1

(6S,9aS)-N-Benzyl-8-((6-(3-(4-(dimethylamino)piperidin-1-yl)azetidin-1-yl)-5-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

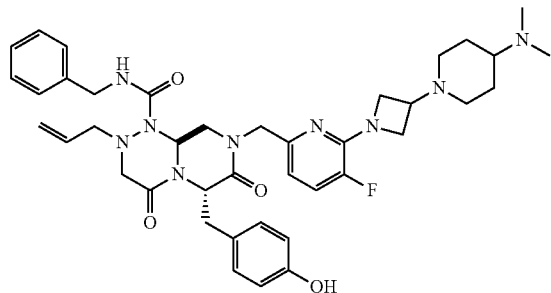

The title compound (37.1 mg, yield: 22%) was produced from (2S)-2-(2-(((Benzylcarbamoyl)amino)(prop-2-en-1-yl)amino)acetamido)-3-(4-(tert-butoxy)phenyl)-N-(2,2-diethoxyethyl)-N-((6-(3-(4-(dimethylamino)piperidin-1-yl)azetidin-1-yl)-5-fluoropyridin-2-yl)methyl)propanamide (200 mg, 0,225 mmol) described in Production Example 25-7 employing the similar procedure as in Production Example 2-4.
¹H-NMR Spectrum (400 MHz, CDCl₃) δ(ppm): 1.60-2.00 (6H, m), 2.08-2.18 (1H, m), 2.21 (6H, s), 2.95 (1H, d, J=10.7 Hz), 3.09-3.22 (2H, m), 3.35-3.71 (8H, m), 3.86 (2H, d, J=7.0 Hz), 4.09 (1H, dd, J=4.1 Hz, 11.1 Hz), 4.20 (1H, dd, J=5.3 Hz, 15.2 Hz), 4.27-4.47 (3H, m), 4.90-5.02 (2H, m), 5.12-5.33 (3H, m), 5.64-5.79 (1H, m), 6.45-6.62 (4H, m), 6.63-6.73 (2H, m), 7.13 (1H, dd, J=7.9 Hz, 11.4 Hz), 7.19-7.44 (5H, m), 9.82 (1H, brs).
ESI-MS (m/z): 740.70 [M+H]+.

Production Example 25-1

1-(1-(Diphenylmethyl)azetidin-3-yl)-N,N-dimethylpiperidine-4-amine

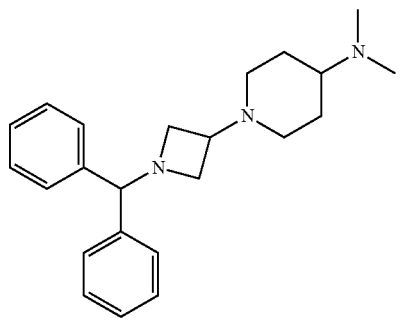 [SMILES: CN(C)C1CCN(C2CN(C(c3ccccc3)c3ccccc3)C2)CC1]

The title compound (1.30 g, yield: 89%) was produced from a commercially available product of N,N-dimethylpiperidine-4-amine (640 mg, 5.00 mmol) employing the similar procedure as in Production Example 1-3-1.
ESI-MS (m/z): 350.35 [M+H]+.

Production Example 25-2

1-(Azetidin-3-yl)-N,N-dimethylpiperidine-4-amine

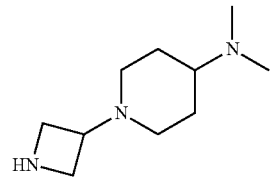

The title compound was produced in the form of a mixture (1.24 g) with benzylbenzene from 1-(1-(diphenylmethyl)azetidin-3-yl)-N,N-dimethylpiperidine-4-amine (1.30 g, 3.71 mmol) described in Production Example 25-1 employing the similar procedure as in Production Example 1-3-2.
¹H-NMR Spectrum (400 MHz, CDCl₃) δ(ppm): 1.46-1.60 (2H, m), 1.73-1.87 (4H, m), 2.07-2.22 (1H, m), 2.28 (6H, s), 2.77-2.87 (2H, m), 3.12-3.21 (1H, m), 3.50-3.58 (2H, m), 3.59-3.66 (2H, m).

Production Example 25-3

(6-(3-(4-(Dimethylamino)piperidin-1-yl)azetidin-1-yl)-5-fluoropyridin-2-yl)methanol

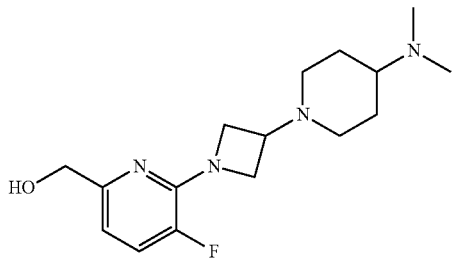 [SMILES: CN(C)C1CCN(C2CN(c3nc(CO)ccc3F)C2)CC1]

The title compound (240 mg, yield: 63%) was produced from a commercially available product of (6-chloro-5-fluoropyridin-2-yl)methanol (200 mg, 1.24 mmol) and a mixture (650 mg) of 1-(azetidin-3-yl)-N,N-dimethylpiperidine-4-amine and benzylbenzene described in Production Example 25-2 employing the similar procedure as in Example 1.
ESI-MS (m/z): 309.11 [M+H]+.

Production Example 25-4

6-(3-(4-(Dimethylamino)piperidin-1-yl)azetidin-1-yl)-5-fluoropyridine-2-carbaldehyde

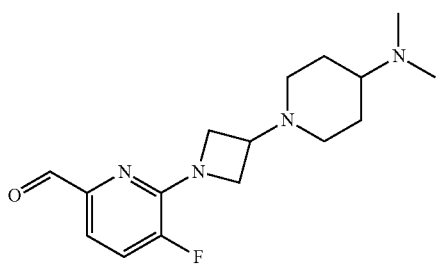 [SMILES: CN(C)C1CCN(C2CN(c3nc(C=O)ccc3F)C2)CC1]

To a mixed solution of (6-(3-(4-(dimethylamino)piperidin-1-yl)azetidin-1-yl)-5-fluoropyridin-2-yl)methanol (240 mg, 0.779 mmol) described in Production Example 25-3 and dichloromethane (6.00 mL) was added Dess-Martin periodinane (400 mg) at 0° C. The resultant mixture was stirred for 1.5 hours. Quenched with an aqueous sodium hydrogen carbonate solution and sodium thiosulfate, and the reaction solution was extracted with chloroform. An organic layer was dried over sodium sulfate and then filtrated, and the solvent was then evaporated under a reduced pressure to give the title compound (320 mg). The product was used in the subsequent reaction without further purification.

Production Example 25-5

1-(1-(6-(((2,2-Diethoxyethyl)amino)methyl)-3-fluoropyridin-2-yl)azetidin-3-yl)-N,N-dimethylpiperidine-4-amine

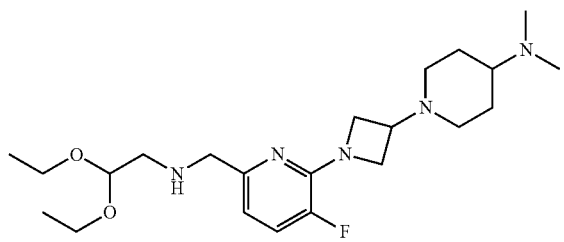 [SMILES: CCOC(CNCc1ccc(F)c(N2CC(N3CCC(N(C)C)CC3)C2)n1)OCC]

The title compound (230 mg, yield: 54%) was produced from 6-(3-(4-(dimethylamino)piperidin-1-yl)azetidin-1-yl)-5-fluoropyridine-2-carbaldehyde (320 mg, 1.04 mmol) described in Production Example 25-4 and a commercially available product of 2,2-diethoxyethan-1-amine (170 mg, 1.28 mmol) employing the similar procedure as in Production Example 1-1-1.
ESI-MS (m/z): 424.42 [M+H]$^+$.

Production Example 25-6

(2S)-2-Amino-3-(4-(tert-butoxy)phenyl)-N-(2,2-diethoxyethyl)-N-((6-(3-(4-(dimethylamino)piperazin-1-yl)azetidin-1-yl)-5-fluoropyridin-2-yl)methyl)propanamide

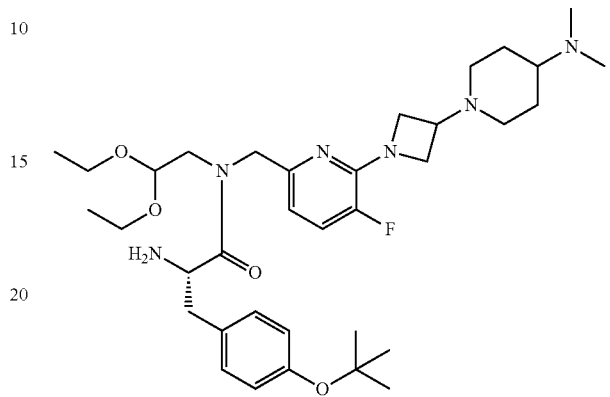

The title compound (250 mg, yield: 72%) was produced from 1-(1-(6-(((2,2-diethoxyethyl)amino)methyl)-3-fluoropyridin-2-yl)azetidin-3-yl)-N,N-dimethylpiperidine-4-amine (230 mg, 0.542 mmol) described in Production Example 25-5 employing the similar procedures as in Production Example 2-1 and Production Example 2-2 (wherein the condensing agent used was HBTU instead of HATU).
ESI-MS (m/z): 643.64 [M+H]$^+$.

Production Example 25-7

(2S)-2-(2-(((Benzylcarbamoyl)amino)(prop-2-en-1-yl)amino)acetamido)-3-(4-(tert-butoxy)phenyl)-N-(2,2-diethoxyethyl)-N-((6-(3-(4-(dimethylamino)piperidin-1-yl)azetidin-1-yl)-5-fluoropyridin-2-yl)methyl)propanamide

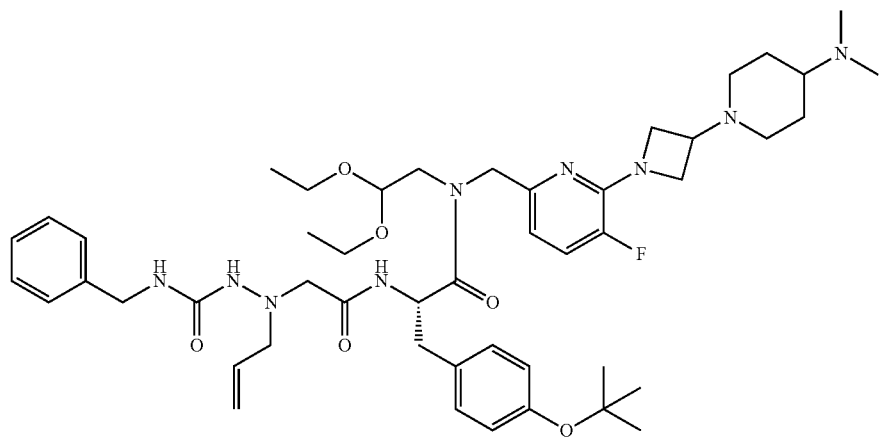 [SMILES: C=CCN(CC(=O)N[C@@H](Cc1ccc(OC(C)(C)C)cc1)C(=O)N(Cc1ccc(F)c(N2CC(N3CCC(N(C)C)CC3)C2)n1)CC(OCC)OCC)NC(=O)NCc1ccccc1]

95

The title compound (290 mg, yield: 84%) was produced from (2S)-2-amino-3-(4-(tert-butoxy)phenyl)-N-(2,2-diethoxyethyl)-N-((6-(3-(4-(dimethylamino)piperidin-1-yl)azetidin-1-yl)-5-fluoropyridin-2-yl)methyl)propanamide (250 mg, 0.389 mmol) described in Production Example 25-6 employing the similar procedure as in Production Example 1-1-4.

ESI-MS (m/z): 888.99 [M+H]⁺.

Reference Example 2

(6S,9aS)-N-Benzyl-8-((6-(3-((3R)-3-(dimethylamino)pyrrolidin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

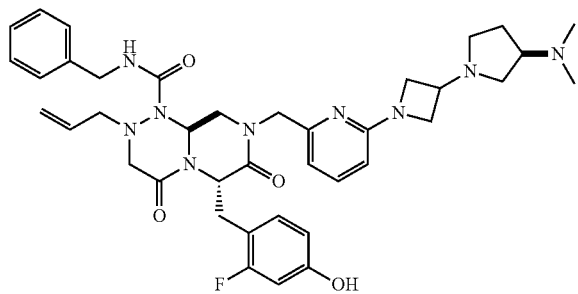

The title compound (5.90 mg, yield: 16%) was produced from (6S,9aS)-N-benzyl-6-((2-fluoro-4-hydroxyphenyl)methyl)-8-((6-fluoropyridin-2-yl)methyl)-4,7-dioxo-2-(prop-2-en-1-yl)-octahydro-1H-pyrazino[2,1-c][1,2,4]triazine-1-carboxamide (30.0 mg, 0.0520 mmol) described in Production Example 1-1-6 and (3R)-1-(azetidin-3-yl)-N,N-dimethylpyrrolidine-3-amine (88.0 mg, 0.260 mmol) described in Production Example 26-2 employing the similar procedure as in Example 1.

¹H-NMR Spectrum (400 MHz, CDCl₃) δ(ppm): 1.56-1.69 (1H, m), 1.84-1.96 (1H, m), 2.18 (6H, s), 2.27-2.36 (1H, m), 2.71-2.87 (2H, m), 2.92-3.00 (1H, m), 3.08-3.18 (2H, m), 3.29-3.35 (1H, m), 3.48-3.60 (3H, m), 3.60-3.72 (2H, m), 3.75-3.82 (1H, m), 3.84-3.91 (1H, m), 3.94-4.00 (1H, m), 4.01-4.07 (1H, m), 4.17-4.30 (2H, m), 4.37-4.50 (1H, m), 4.93-5.01 (1H, m), 5.17-5.24 (2H, m), 5.24-5.28 (1H, m), 5.38-5.47 (1H, m), 5.65-5.80 (2H, m), 5.86-5.93 (1H, m), 6.22-6.25 (1H, m), 6.37-6.39 (1H, m), 6.44-6.48 (1H, m), 6.68-6.72 (1H, m), 6.75-6.81 (1H, m), 7.21-7.26 (2H, m), 7.28-7.32 (1H, m), 7.34-7.40 (2H, m), 7.41-7.47 (1H, m).

ESI-MS (m/z): 726.59 [M+H]⁺.

96

Production Example 26-1

(3R)-1-(1-(Diphenylmethyl)azetidin-3-yl)-N,N-dimethylpyrrolidine-3-amine

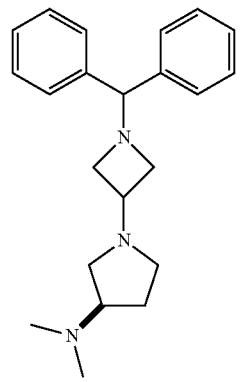 [SMILES: CN(C)[C@@H]1CCN(C2CN(C(c3ccccc3)c3ccccc3)C2)C1]

The title compound (458 mg, yield: 65%) was produced from a commercially available product of 1-(diphenylmethyl)azetidin-3-one (500 mg, 2.11 mmol) and a commercially available product of (3R)-(+)-3-(dimethylamino)-pyrrolidine (289 mg, 2.53 mmol) employing the similar procedure as in Production Example 1-3-1.

¹H-NMR Spectrum (400 MHz, CDCl₃) δ(ppm): 1.63-1.74 (1H, m), 1.91-2.03 (1H, m), 2.09-2.15 (1H, m), 2.18 (6H, s), 2.27-2.37 (1H, m), 2.66-2.76 (2H, m), 2.79-2.83 (1H, m), 2.92-2.96 (2H, m), 3.06-3.13 (1H, m), 3.33-3.38 (2H, m), 4.40 (1H, s), 7.15-7.20 (2H, m), 7.24-7.29 (4H, m), 7.38-7.42 (4H, m).

Production Example 26-2

(3R)-1-(azetidin-3-yl)-N,N-dimethylpyrrolidine-3-amine

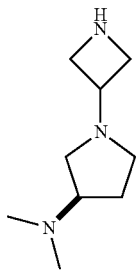

The title compound was produced in the form of a mixture (408 mg) with benzylbenzene from (3R)-1-(1-(diphenylmethyl)azetidin-3-yl)-N,N-dimethylpyrrolidine-3-amine (458 mg, 1.37 mmol) described in Production Example 26-1 employing the similar procedure as in Production Example 1-3-2. The product was used in the subsequent reaction without further purification.

ESI-MS (m/z): 170.0 [M+H]⁺.

Reference Example 3

(6S,9aS)-N-Benzyl-8-((6-(3-(4-(dimethylamino)piperidin-1-yl)azetidin-1-yl)-5-fluoropyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

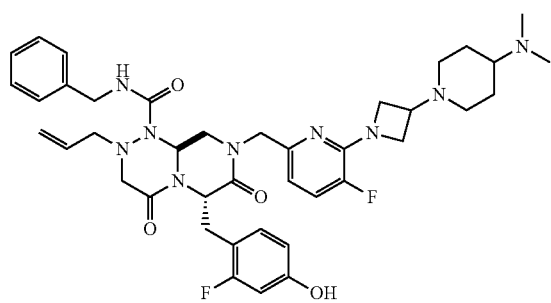

The title compound (19.0 mg, yield: 39%) was produced from (6S,9aS)-N-benzyl-8-((6-chloro-5-fluoropyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide (40.0 mg, 0.0655 mmol) described in Production Example 27-4 and 1-(azetidin-3-yl)-N,N-dimethylpiperidine-4-amine (40.0 mg, 0.0655 mmol) described in Production Example 25-2 employing the similar procedure as in Example 1.

$^1$H-NMR Spectrum (400 MHz, CDCl$_3$) δ(ppm): 1.21-2.16 (7H, m), 2.20 (6H, s), 2.88-2.98 (1H, m), 3.09-3.20 (1H, m), 3.35-3.78 (10H, m), 3.81-3.89 (1H, m), 4.09 (1H, dd, J=4.2 Hz, 11.2 Hz), 4.16-4.31 (2H, m), 4.34-4.42 (1H, m), 4.52 (1H, dd, J=7.4 Hz, 15.6 Hz), 4.91 (1H, d, J=13.9 Hz), 5.19-5.29 (3H, m), 5.45-5.53 (1H, m), 5.67-5.81 (1H, m), 6.00-6.07 (1H, m), 6.42-6.51 (2H, m), 6.62 (1H, dd, J=2.7 Hz, 7.8 Hz), 6.77-6.83 (1H, m), 7.09 (1H, dd, J=8.0 Hz, 11.9 Hz), 7.23-7.43 (5H, m).

ESI-MS (m/z): 758.67 [M+H]$^+$.

Production Example 27-1

((6-Chloro-5-fluoropyridin-2-yl)methyl)(2,2-diethoxyethyl)amine

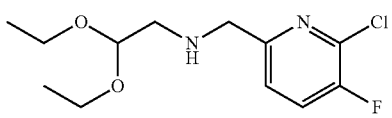 [SMILES: CCOC(CNCc1ccc(F)c(Cl)n1)OCC]

The title compound (233 mg, yield: 68%) was produced from a commercially available product of 6-chloro-5-fluoropyridine-2-carbaldehyde (198 mg) employing the similar procedure as in Production Example 1-1-1.

$^1$H-NMR Spectrum (400 MHz, CDCl$_3$) δ(ppm): 1.22 (6H, t, J=7.1 Hz), 2.75 (2H, d, J=5.5 Hz), 3.47-3.61 (2H, m), 3.64-3.77 (2H, m), 3.90 (2H, s), 4.63 (1H, t, J=5.5 Hz), 7.32 (1H, dd, J=3.3 Hz, 8.2 Hz), 7.40-7.49 (1H, m).

Production Example 27-2

(2S)-2-Amino-3-(4-(benzyloxy)-2-fluorophenyl)-N-((6-chloro-5-fluoropyridin-2-yl)methyl)-N-(2,2-diethoxyethyl)propanamide

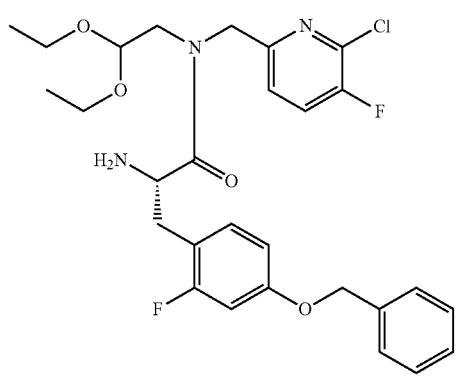 [SMILES: CCOC(CN(Cc1ccc(F)c(Cl)n1)C(=O)[C@@H](N)Cc1ccc(OCc2ccccc2)cc1F)OCC]

The title compound (445 mg, yield: 97%) was produced from ((6-chloro-5-fluoropyridin-2-yl)methyl)(2,2-diethoxyethyl)amine (233 mg, 0.842 mmol) described in Production Example 27-1 employing the similar procedures as in Production Example 1-1-2 and Production Example 1-1-3.

ESI-MS (m/z): 548.38 [M+H]$^+$.

Production Example 27-3

(2S)-2-(2-((Benzylcarbamoyl)amino)(prop-2-en-1-yl)amino)acetamido)-3-(4-(benzyloxy)-2-fluorophenyl)-N-((6-chloro-5-fluoropyridin-2-yl)methyl)-N-(2,2-diethoxyethyl)propanamide

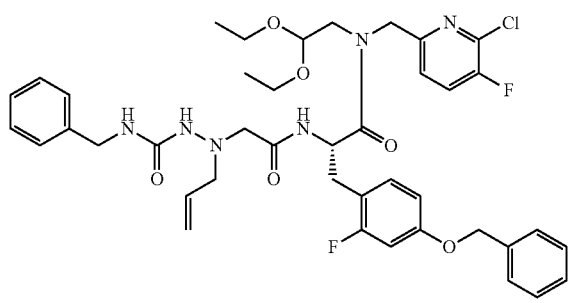 [SMILES: C=CCN(CC(=O)N[C@@H](Cc1ccc(OCc2ccccc2)cc1F)C(=O)N(Cc1ccc(F)c(Cl)n1)CC(OCC)OCC)NC(=O)NCc1ccccc1]

The title compound (579 mg, yield: 90%) was produced from (2S)-2-amino-3-(4-(benzyloxy)-2-fluorophenyl)-N-((6-chloro-5-fluoropyridin-2-yl)methyl)-N-(2,2-diethoxyethyl)propanamide (445 mg, 0.812 mmol) described in Production Example 27-2 employing the similar procedure as in Production Example 1-1-4.

ESI-MS (m/z): 793.62 [M+H]$^+$.

Production Example 27-4

(6S,9aS)-N-Benzyl-8-((6-chloro-5-fluoropyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

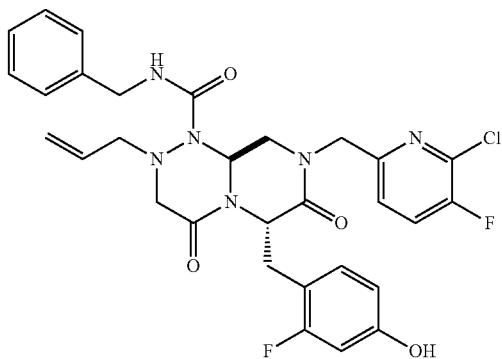

The title compound (288 mg, yield: 65%) was produced from (2S)-2-(2-((benzylcarbamoyl)amino)(prop-2-en-1-yl)amino)acetamido)-3-(4-(benzyloxy)-2-fluorophenyl)-N-((6-chloro-5-fluoropyridin-2-yl)methyl)-N-(2,2-diethoxyethyl)propanamide (579 mg, 0.730 mmol) described in Production Example 27-3 employing the similar procedures as in Production Example 1-1-5 and Production Example 1-1-6.

ESI-MS (m/z): 611.34 [M+H]$^+$.

Reference Example 4

(6S,9aS)-N-Benzyl-6-((2-fluoro-4-hydroxyphenyl)methyl)-8-((5-fluoro-6-(3-((1S,4S)-5-(propan-2-yl)-2,5-diazabicyclo[2.2.1]heptan-2-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

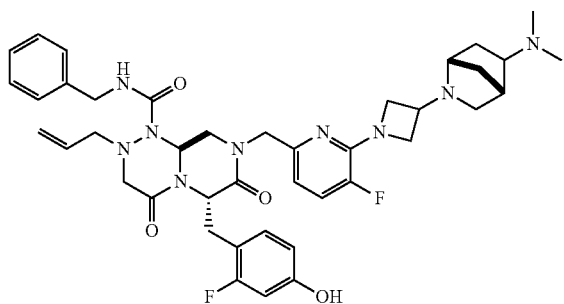

The title compound (14.6 mg, yield: 16%) was produced from (2S)-2-(2-((benzylcarbamoyl)amino)(prop-2-en-1-yl)amino)acetamido)-3-(4-(benzyloxy)-2-fluorophenyl)-N-(2,2-diethoxyethyl)-N-((5-fluoro-6-(3-((1S,4S)-5-(propan-2-yl)-2,5-diazabicyclo[2.2.1]heptan-2-yl)azetidin-1-yl)pyridin-2-yl)methyl)propanamide (116 mg) described in Production Example 28-7 employing the similar procedures as in Production Example 1-1-5 and Production Example 1-1-6.

$^1$H-NMR Spectrum (400 MHz, CDCl$_3$) δ(ppm): 0.97 (3H, d, J=6.3 Hz), 1.04 (3H, d, J=5.9 Hz), 1.61-1.70 (1H, m), 1.73-1.81 (1H, m), 2.36-2.46 (1H, m), 2.59-2.83 (4H, m), 2.98-3.05 (1H, m), 3.10-3.18 (1H, m), 3.39-3.79 (101H, m), 3.82-3.90 (1H, m), 4.08 (1H, dd, J=4.3 Hz, 11.1 Hz), 4.13-4.21 (1H, m), 4.21-4.34 (2H, m), 4.49 (1H, dd, J=7.1 Hz, 15.9 Hz), 4.91 (1H, d, J=13.9 Hz), 5.18-5.30 (3H, m), 5.49 (1H, dd, J=4.2 Hz, 10.8 Hz), 5.69-5.82 (1H, m), 6.03-6.09 (1H, m), 6.42-6.52 (2H, m), 6.57-6.63 (1H, m), 6.80-6.88 (1H, m), 7.08 (1H, dd, J=7.8 Hz, 11.9 Hz), 7.18-7.42 (5H, m).

ESI-MS (m/z): 770.73 [M+H]$^+$.

Production Example 28-1

1-(6-(Diethoxymethyl)-3-fluoropyridin-2-yl)azetidin-3-ol

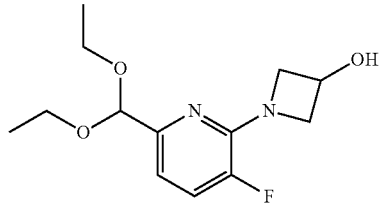 [SMILES: CCOC(OCC)c1ccc(F)c(N2CC(O)C2)n1]

The title compound (89.0 mg, yield: 51%) was produced from 2-chloro-6-(diethoxymethyl)-3-fluoropyridine (150 mg, 0.642 mol) described in Production Example 24-1-1 and a commercially available product of azetidin-3-ol hydrochloride (105 mg, 0.963 mmol) employing the similar procedure as in Production Example 24-1-2.

$^1$H-NMR Spectrum (400 MHz, CDCl$_3$) δ(ppm): 1.19-1.31 (6H, m), 3.51-3.76 (4H, m), 3.93-4.04 (2H, m), 4.34-4.47 (2H, m), 4.68-4.81 (1H, m), 5.29 (1H, s), 6.85-6.94 (1H, m), 7.10-7.21 (1H, m).

Production Example 28-2

1-(6-(Diethoxymethyl)-3-fluoropyridin-2-yl)azetidin-3-one

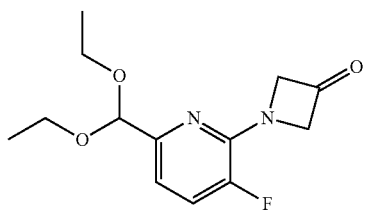 [SMILES: CCOC(OCC)c1ccc(F)c(N2CC(=O)C2)n1]

A crude product (212 mg) of the title compound was produced from 1-(6-(diethoxymethyl)-3-fluoropyridin-2-yl)azetidin-3-ol (214 mg, 0.792 mmol) described in Production Example 28-1 employing the similar procedure as in Production Example 7-2. The product was used in the subsequent reaction without further purification.

¹H-NMR Spectrum (400 MHz, CDCl₃) δ(ppm): 1.20-1.32 (6H, m), 3.53-3.77 (4H, m), 4.92 (4H, d, J=2.0 Hz), 5.32 (1H, s), 7.01-7.09 (1H, m), 7.27-7.32 (1H, m).

Production Example 28-3

(1S,4S)-2-(1-(6-Diethoxymethyl)-3-fluoropyridin-2-yl)azetidin-3-yl)-5-(propan-2-yl)-2,5-diazabicyclo[2.2.1]heptane

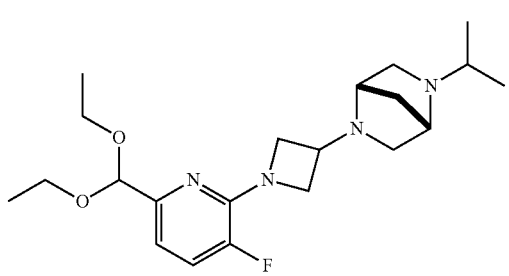

The title compound (66.0 mg, yield: 78%) was produced from 1-(6-(diethoxymethyl)-3-fluoropyridin-2-yl)azetidin-3-one (57.6 mg, 0.215 mmol) described in Production Example 28-2 and a commercially available product of (1S,4S)-2-(propan-2-yl)-2,5-diazabicyclo[2.2.1]heptane (95.0 mg, 0.258 mmol) employing the similar procedure as in Production Example 1-3-1.

ESI-MS (m/z): 393.33 [M+H]⁺.

Production Example 28-4

5-Fluoro-6-(3-((1S,4S)-5-(propan-2-yl)-2,5-diazabicyclo[2.2.1]heptan-2-yl)azetidin-1-yl)pyridine-2-carbaldehyde

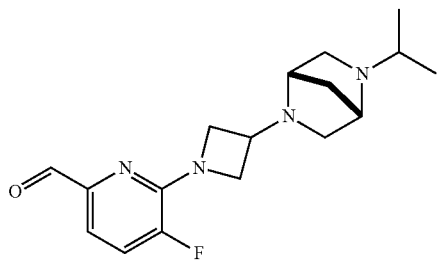

A crude product (53.5 mg) of the title compound was produced from (1S,4S)-2-(1-(6-diethoxymethyl)-3-fluoropyridin-2-yl)azetidin-3-yl)-5-(propan-2-yl)-2,5-diazabicyclo[2.2.1]heptane (157 mg, 0.428 mmol) described in Production Example 28-3 employing the similar procedure as in Production Example 24-1-3. The product was used in the subsequent reaction without further purification.

ESI-MS (m/z): 319.18 [M+H]⁺.

Production Example 28-5

(2,2-Diethoxyethyl)((5-fluoro-6-(3-((1S,4S)-5-(propan-2-yl)-2,5-diazabicyclo[2.2.1]heptan-2-yl)azetidin-1-yl)pyridin-2-yl)methyl)amine

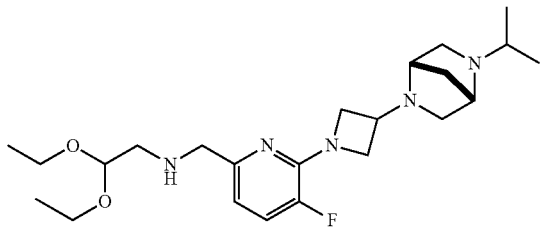

The title compound (62.0 mg, yield: 82%) was produced from the crude product (53.5 mg) of 5-fluoro-6-(3-((1S,4S)-5-(propan-2-yl)-2,5-diazabicyclo[2.2.1]heptan-2-yl)azetidin-1-yl)pyridine-2-carbaldehyde described in Production Example 28-4 employing the similar procedure as in Production Example 1-1-1.

ESI-MS (m/z): 436.39 [M+H]⁺.

Production Example 28-6

(2S)-2-Amino-3-(4-(benzyloxy)-2-fluorophenyl)-N-(2,2-diethoxyethyl)-N-((5-fluoro-6-(3-((1S,4S)-5-(propan-2-yl)-2,5-diazabicyclo[2.2.1]heptan-2-yl)azetidin-1-yl)pyridin-2-yl)methyl)propanamide

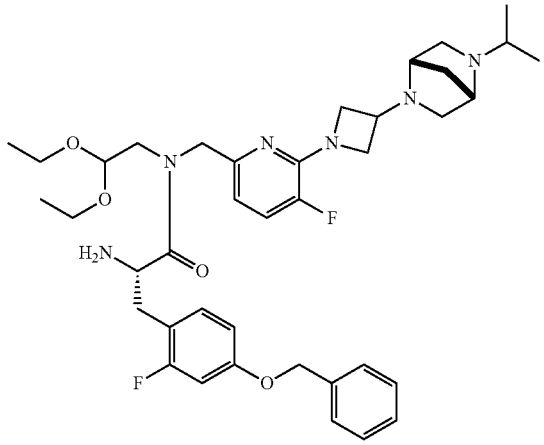

The title compound (84.0 mg, yield: 86%) was produced from (2,2-diethoxyethyl)((5-fluoro-6-(3-((1S,4S)-5-(propan-2-yl)-2,5-diazabicyclo[2.2.1]heptan-2-yl)azetidin-1-yl)pyridin-2-yl)methyl)amine (62.0 mg, 0.142 mmol) described in Production Example 28-5 employing the similar procedures as in Production Example 1-1-2 and Production Example 1-1-3.

ESI-MS (m/z): 707.69 [M+H]⁺.

Production Example 28-7

(2S)-2-(2-((Benzylcarbamoyl)amino)(prop-2-en-1-yl)amino)acetamido)-3-(4-(benzyloxy)-2-fluorophenyl)-N-(2,2-diethoxyethyl)-N-((5-fluoro-6-(3-((1S,4S)-5-(propan-2-yl)-2,5-diazabicyclo[2.2.1]heptan-2-yl)azetidin-1-yl)pyridin-2-yl)methyl)propanamide

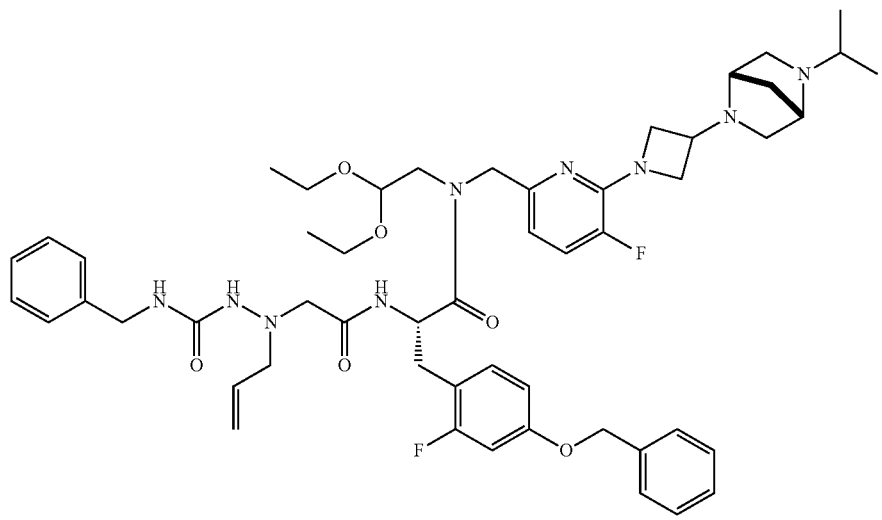 [SMILES: C=CCN(CC(=O)N[C@@H](Cc1ccc(OCc2ccccc2)cc1F)C(=O)N(Cc1ccc(F)c(N2CC(N3C[C@@H]4C[C@H]3CN4C(C)C)C2)n1)CC(OCC)OCC)NC(=O)NCc1ccccc1]

The title compound (116 mg, yield: quantitative) was produced from (2S)-2-amino-3-(4-(benzyloxy)-2-fluorophenyl)-N-(2,2-diethoxyethyl)-N-((5-fluoro-6-(3-((1S,4S)-5-(propan-2-yl)-2,5-diazabicyclo[2.2.1]heptan-2-yl)azetidin-1-yl)pyridin-2-yl)methyl)propanamide (84.0 mg, 0.119 mmol) described in Production Example 28-6 employing the similar procedure as in Production Example 1-1-4.

ESI-MS (m/z): 952.95 [M+H]$^+$.

Reference Example 5

(6S,9aS)-N-Benzyl-6-((2-fluoro-4-hydroxyphenyl)methyl)-8-((6-(3-(methyl(2-(morpholin-4-yl)ethyl)amino)azetidin-1-yl)pyridin-2-yl)methyl)-4,7-dioxo-2-(prop-2-en-1-yl)-octahydro-1H-pyrazino[2,1-c][1,2,4]triazine-1-carboxamide The title compound (35.0 mg, yield: 39%) was produced from (2S)-2-(2-(((benzylcarbamoyl)amino)(prop-2-en-1-yl)amino)acetamido)-3-(4-(benzyloxy)-2-fluorophenyl)-N-(2,2-diethoxyethyl)-N-((6-(3-(methyl(2-(morpholin-4-yl)ethyl)amino)azetidin-1-yl)pyridin-2-yl)methyl)propanamide (110 mg, 0.117 mmol) described in Production Example 29-7 employing the similar procedures as in Production Example 1-1-5 and Production Example 1-1-6.

$^1$H-NMR Spectrum (400 MHz, CDCl$_3$) δ(ppm): 2.27 (3H, s), 2.37-2.52 (6H, m), 2.54-2.71 (2H, m), 3.11-3.20 (1H, m), 3.34-3.44 (2H, m), 3.48-3.77 (11H, m), 3.87-3.95 (2H, m), 3.99-4.06 (1H, m), 4.16-4.30 (2H, m), 4.43 (1H, dd, J=6.7 Hz, 15.3 Hz), 4.97 (1H, d, J=13.9 Hz), 5.18-5.28 (3H, m), 5.39 (1H, dd, J=4.2 Hz, 10.6 Hz), 5.66-5.78 (1H, m), 5.93 (1H, dd, J=2.1 Hz, 8.4 Hz), 6.25 (1H, d, J=8.4 Hz), 6.33-6.39 (1H, m), 6.40-6.47 (1H, m), 6.68-6.77 (2H, m), 7.21-7.47 (6H, m).

ESI-MS (m/z): 756.62 [M+H]$^+$.

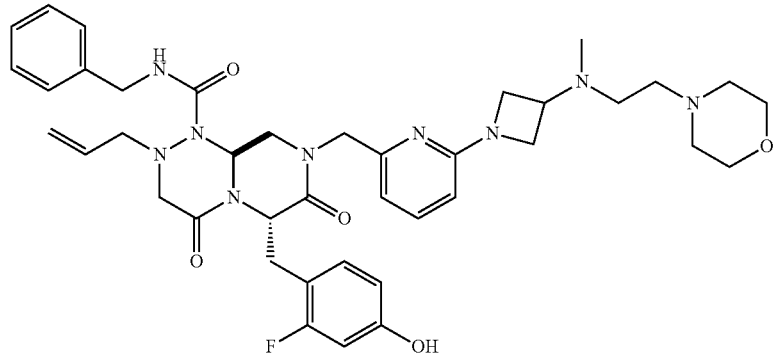

Production Example 29-1

1-(6-(1,3-Dioxolan-2-yl)pyridin-2-yl)azetidin-3-ol

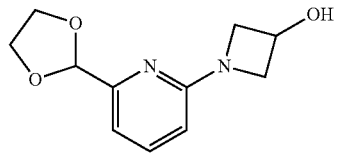 [SMILES: OC1CN(c2cccc(C3OCCO3)n2)C1]

The title compound (263 mg, yield: quantitative) was produced from a commercially available product of 2-(1,3-dioxolan-2-yl)-6-fluoropyridine (200 mg, 1.18 mol) and a commercially available product of azetidin-3-ol hydrochloride (194 mg, 1.77 mmol) employing the similar procedure as in Production Example 24-1-2.

$^1$H-NMR Spectrum (400 MHz, CDCl$_3$) δ(ppm): 3.83-3.91 (2H, m), 4.00-4.20 (4H, m), 4.26-4.35 (2H, m), 4.70-4.83 (1H, m), 5.72 (1H, s), 6.24-6.31 (1H, m), 6.80-6.89 (1H, m), 7.42-7.53 (1H, m).

Production Example 29-2

1-(6-(1,3-Dioxolan-2-yl)pyridin-2-yl)azetidin-3-one

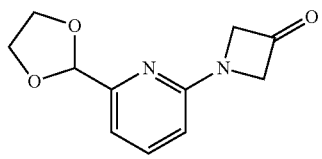 [SMILES: O=C1CN(c2cccc(C3OCCO3)n2)C1]

A crude product (261 mg) of the title compound was produced from 1-(6-(1,3-dioxolan-2-yl)pyridin-2-yl)azetidin-3-ol (263 mg, 1.18 mmol) described in Production Example 29-1 employing the similar procedure as in Production Example 7-2. The product was used in the subsequent reaction without further purification.

$^1$H-NMR Spectrum (400 MHz, CDCl$_3$) δ(ppm): 3.99-4.23 (4H, m), 4.82 (4H, s), 5.75 (1H, s), 6.47-6.57 (1H, m), 6.98-7.04 (1H, m), 7.55-7.65 (1H, m).

Production Example 29-3

1-(6-(1,3-Dioxolan-2-yl)pyridin-2-yl)-N-methyl-N-(2-(morpholin-4-yl)ethyl)azetidine-3-amine

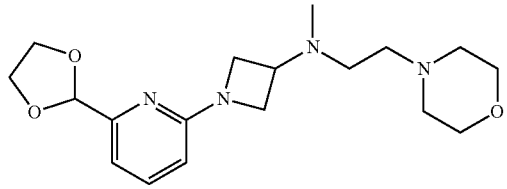 [SMILES: CN(CCN1CCOCC1)C1CN(c2cccc(C3OCCO3)n2)C1]

The title compound (157 mg, yield: 76%) was produced from 1-(6-(1,3-dioxolan-2-yl)pyridin-2-yl)azetidin-3-one (130 mg, 0.590 mmol) described in Production Example 29-2 and a commercially available product of methyl(2-(morpholin-4-yl)ethyl)amine (176 mg, 0.767 mmol) employing the similar procedure as in Production Example 1-3-1.

ESI-MS (m/z): 349.22 [M+H]$^+$.

Production Example 29-4

6-(3-(Methyl(2-(morpholin-4-yl)ethyl)amino)azetidin-1-yl)pyridine-2-carbaldehyde

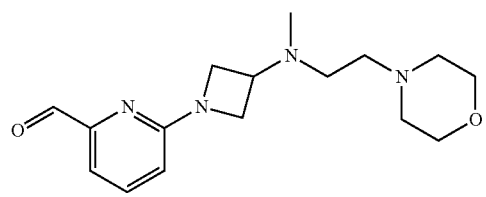 [SMILES: CN(CCN1CCOCC1)C1CN(c2cccc(C=O)n2)C1]

To a mixed solution of 1-(6-(1,3-dioxolan-2-yl)pyridin-2-yl)-N-methyl-N-(2-(morpholin-4-yl)ethyl)azetidine-3-amine (157 mg, 0.451 mmol) described in Production Example 29-3, acetonitrile (5.00 mL) and water (0.500 mL) was added p-toluenesulfonic acid monohydrate (386 mg, 2.03 mmol). The resultant mixture was stirred at 100° C. for 5 hours. The mixture was cooled to room temperature, and then the solvent was evaporated under a reduced pressure. A saturated aqueous sodium hydrogen carbonate solution was added to the residue, and the resultant solution was extracted with dichloromethane three times. An organic layer was dried over anhydrous magnesium sulfate and then filtrated. The solvent was evaporated under a reduced pressure to give a crude product (122 mg) of the title compound. The product was used in the subsequent reaction without further purification.

ESI-MS (m/z): 305.19 [M+H]$^+$.

Production Example 29-5

1-(6-(((2,2-Diethoxyethyl)amino)methyl)pyridin-2-yl)-N-methyl-N-(2-(morpholin-4-yl)ethyl)azetidine-3-amine

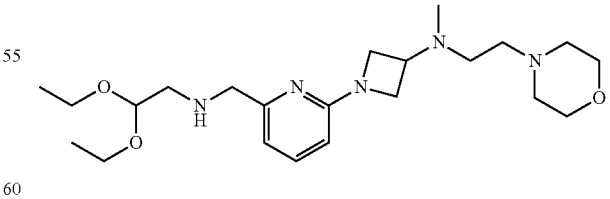

The title compound (55.0 mg, yield: 33%) was produced from the crude product (122 mg) of 6-(3-(methyl(2-(morpholin-4-yl)ethyl)amino)azetidin-1-yl)pyridine-2-carbaldehyde described in Production Example 29-4 employing the similar procedure as in Production Example 1-1-1.

ESI-MS (m/z): 422.40 [M+H]$^+$.

Production Example 29-6

(2S)-2-Amino-3-(4-(benzyloxy)-2-fluorophenyl)-N-(2,2-diethoxyethyl)-N-((6-(3-(methyl(2-(morpholin-4-yl)ethyl)amino)azetidin-1-yl)pyridin-2-yl)methyl)propanamide

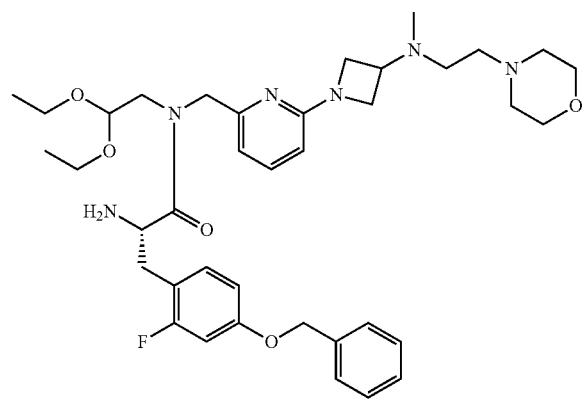 [SMILES: CCOC(CN(Cc1cccc(N2CC(N(C)CCN3CCOCC3)C2)n1)C(=O)[C@@H](N)Cc1ccc(OCc2ccccc2)cc1F)OCC]

The title compound (94.0 mg, yield: quantitative) was produced from 1-(6-(((2,2-diethoxyethyl)amino)methyl)pyridin-2-yl)-N-methyl-N-(2-(morpholin-4-yl)ethyl)azetidine-3-amine (55.0 mg, 0.130 mmol) described in Production Example 29-5 employing the similar procedures as in Production Example 1-1-2 and Production Example 1-1-3.
ESI-MS (m/z): 693.62 [M+H]$^+$.

Production Example 29-7

(2S)-2-(2-(((Benzylcarbamoyl)amino)(prop-2-en-1-yl)amino)acetamido)-3-(4-(benzyloxy)-2-fluorophenyl)-N-(2,2-diethoxyethyl)-N-((6-(3-(methyl(2-(morpholin-4-yl)ethyl)amino)azetidin-1-yl)pyridin-2-yl)methyl)propanamide The title compound (110 mg, yield: 92%) was produced from (2S)-2-amino-3-(4-(benzyloxy)-2-fluorophenyl)-N-(2,2-diethoxyethyl)-N-((6-(3-(methyl(2-(morpholin-4-yl)ethyl)amino)azetidin-1-yl)pyridin-2-yl)methyl)propanamide (94.0 mg) described in Production Example 29-6 employing the similar procedure as in Production Example 1-1-4.
ESI-MS (m/z): 938.84 [M+H]$^+$.

Reference Example 6

(6S,9aS)-N-Benzyl-8-((6-(3-((2-(dimethylamino)ethyl)(methyl)amino)azetidin-1-yl)-5-fluoropyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide

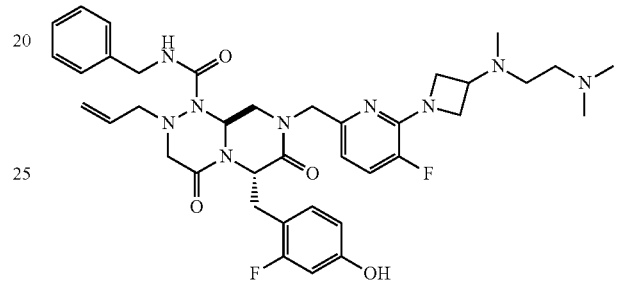

The title compound (59.0 mg, yield: 28%) was produced from (2S)-2-(2-(((benzylcarbamoyl)amino)(prop-2-en-1-yl)amino)acetamido)-3-(4-(benzyloxy)-2-fluorophenyl)-N-(2,2-diethoxyethyl)-N-((6-(3-((2-(dimethylamino)ethyl)(methyl)amino)azetidin-1-yl)-5-fluoropyridin-2-yl)methyl)propanamide (263 mg, 0.288 mmol) described in Production Example 30-5 employing the similar procedure as in Production Example 27-4.
$^1$H-NMR Spectrum (400 MHz, CDCl$_3$) δ(ppm): 2.23 (3H, s), 2.24 (6H, s), 2.24-2.44 (2H, m), 2.54-2.66 (2H, m), 3.15-3.72 (10H, m), 3.76-3.93 (21, m), 4.07-4.31 (3H, m), 4.39-4.51 (1H, m), 4.96 (1H, d, J=13.8 Hz), 5.15-5.28 (3H, m), 5.34-5.42 (1H, m), 5.65-5.80 (1H, m), 6.09-6.17 (1H, m), 6.36-6.45 (1H, m), 6.48-6.56 (1H, m), 6.59-6.74 (21H, m), 7.09 (1H, dd, J=8.0 Hz, 11.7 I-z), 7.20-7.43 (5H, m).
ESI-MS (m/z): 732.63 [M+H]$^+$.

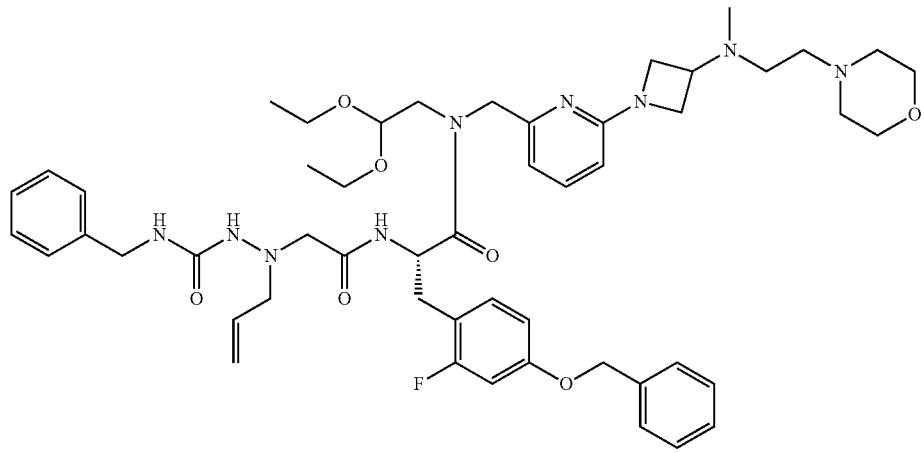 [SMILES: C=CCN(CC(=O)N[C@@H](Cc1ccc(OCc2ccccc2)cc1F)C(=O)N(Cc1cccc(N2CC(N(C)CCN3CCOCC3)C2)n1)CC(OCC)OCC)NC(=O)NCc1ccccc1]

Production Example 30-1

1-(6-(Diethoxymethyl)-3-fluoropyridin-2-yl)-N-(2-(dimethylamino)ethyl)-N-methyl azetidine-3-amine

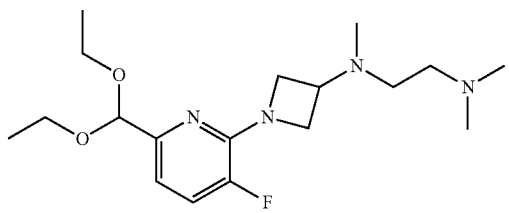 [SMILES: CCOC(OCC)c1ccc(F)c(N2CC(N(C)CCN(C)C)C2)n1]

The title compound (128 mg, yield: 54%) was produced from 1-(6-(diethoxymethyl)-3-fluoropyridin-2-yl)azetidin-3-one (180 mg, 0.671 mmol) described in Production Example 28-2 and a commercially available product of (2-(dimethylamino)ethyl)(methyl)amine (103 mg, 1.01 mmol) employing the similar procedure as in Production Example 1-3-1.

ESI-MS (m/z): 355.27 [M+H]$^+$.

Production Example 30-2

6-(3-((2-(Dimethylamino)ethyl)(methyl)amino)azetidin-1-yl)-5-fluoropyridine-2-carbaldehyde

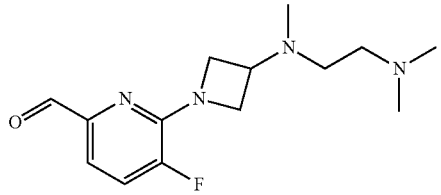 [SMILES: CN(C)CCN(C)C1CN(c2nc(C=O)ccc2F)C1]

A crude product (101 mg) of the title compound was produced from 1-(6-(Diethoxymethyl)-3-fluoropyridin-2-yl)-N-(2-(dimethylamino)ethyl)-N-methylazetidine-3-amine (128 mg, 0.361 mmol) described in Production Example 30-1 employing the similar procedure as in Production Example 24-1-3. The product was used in the subsequent reaction without further purification.

ESI-MS (m/z): 281.11 [M+H]$^+$.

Production Example 30-3

1-(6-(((2,2-Diethoxyethyl)amino)methyl)-3-fluoropyridin-2-yl)-N-(2-(dimethylamino)ethyl)-N-methyl azetidine-3-amine

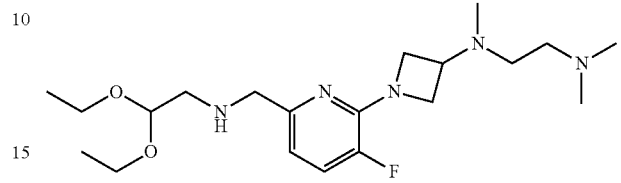

The title compound (125 mg, yield: 87%) was produced from the crude product (101 mg) of 6-(3-((2-(dimethylamino)ethyl)(methyl)amino)azetidin-1-yl)-5-fluoropyridine-2-carbaldehyde described in Production Example 30-2 employing the similar procedure as in Production Example 1-1-1.

ESI-MS (m/z): 398.33 [M+H]$^+$.

Production Example 30-4

(2S)-2-Amino-3-(4-(benzyloxy)-2-fluorophenyl)-N-(2,2-diethoxyethyl)-N-((6-(3-((2-(dimethylamino)ethyl)(methyl)amino)azetidin-1-yl)-5-fluoropyridin-2-yl)methyl)propanamide

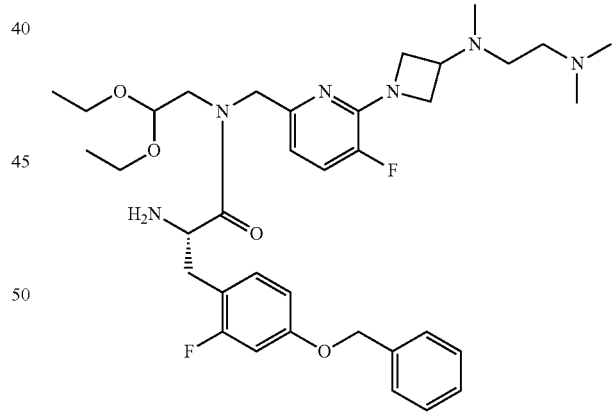

The title compound (250 mg, yield: quantitative) was produced from 1-(6-(((2,2-diethoxyethyl)amino)methyl)-3-fluoropyridin-2-yl)-N-(2-(dimethylamino)ethyl)-N-methylazetidine-3-amine (125 mg, 0.314 mmol) described in Production Example 30-3 employing the similar procedures as in Production Example 1-1-2 and Production Example 1-1-3.

ESI-MS (m/z): 669.64 [M+H]$^+$.

Production Example 30-5

(2S)-2-(2-(((Benzylcarbamoyl)amino)(prop-2-en-1-yl)amino)acetamido)-3-(4-(benzyloxy)-2-fluorophenyl)-N-(2,2-diethoxyethyl)-N-((6-(3-((2-(dimethylamino)ethyl)(methyl)amino)azetidin-1-yl)-5-fluoropyridin-2-yl)methyl)propanamide

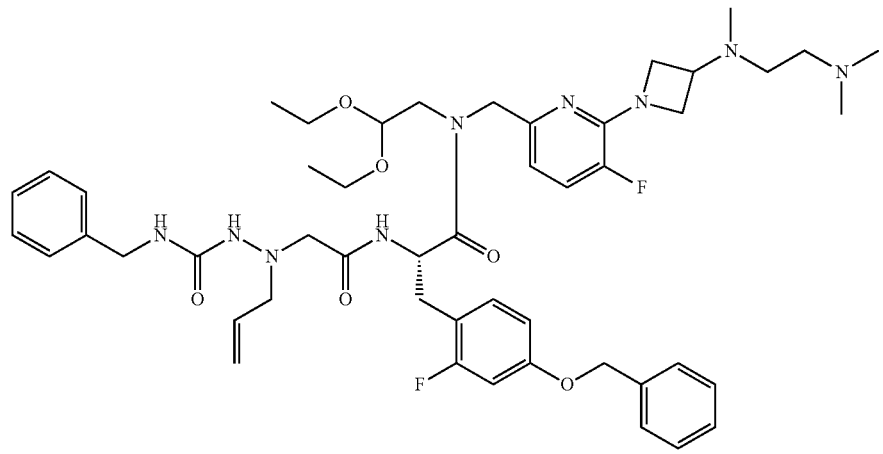 [SMILES: C=CCN(CC(=O)N[C@@H](Cc1ccc(OCc2ccccc2)cc1F)C(=O)N(Cc1ccc(F)c(N2CC(N(C)CCN(C)C)C2)n1)CC(OCC)OCC)NC(=O)NCc1ccccc1]

The title compound (263 mg, yield: 94%) was produced from (2S)-2-amino-3-(4-(benzyloxy)-2-fluorophenyl)-N-(2,2-diethoxyethyl)-N-((6-(3-(((2-(dimethylamino)ethyl)(methyl)amino)azetidin-1-yl)-5-fluoropyridin-2-yl)methyl)propanamide (250 mg) described in Production Example 30-4 employing the similar procedure as in Production Example 1-1-4.

ESI-MS (m/z): 914.82 [M+H]$^+$.

Example 25

4-(((6S,9aS)-1-(Benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate

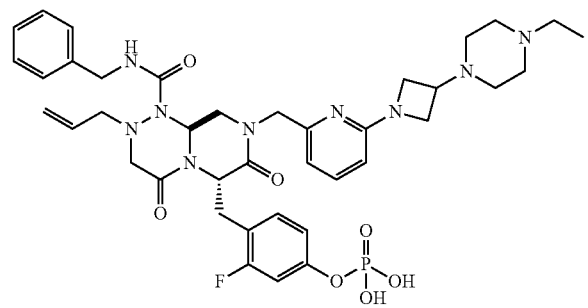

To a mixed solution of phosphorus oxychloride (257 μL, 2.76 mmol) and THF (10.0 mL) was dropwise added a mixed solution of (6S,9aS)-N-benzyl-8-((6-(3-(4-ethylpiperazin-1-yl)azetidin-1-yl)pyridin-2-yl)methyl)-6-(((2-fluoro-4-hydroxyphenyl)methyl)-4,7-dioxo-2-(prop-2-en-1-yl)-octahydro-1H-pyrazino[2,1-c][1,2,4]triazine-1-carboxamide (1.00 g, 1.38 mmol) described in Example 1, triethylamine (768 μL, 5.52 mmol) and THF (10.0 mL) over 10 minutes under a nitrogen atmosphere at −15° C. or lower. The reaction mixture was stirred at −15° C. or lower for 1 hour and 10 minutes. To the reaction mixture was dropwisely added a mixed solution of a 5 N aqueous sodium hydroxide solution (2.03 mL, 10.1 mmol) and water (21.0 mL) over 5 minutes at 10° C. or lower. The reaction mixture was stirred at room temperature for 35 minutes, then ethyl acetate was added to the reaction mixture, and then the resultant solution was partitioned. An aqueous layer was further washed with ethyl acetate, and then 5 N hydrochloric acid was added to the solution to adjust the pH value of the solution at a neutral value. The solvent was distilled away from the reaction mixture under a reduced pressure. Dichloromethane, ethanol and methanol were added to the resultant residue and then stirred, and then the resultant suspension was filtrated using Celite. The solvent was distilled away from the filtrate under a reduced pressure, and the resultant residue was purified by ODS silica gel column chromatography (elution solvent: water/methanol) to give the title compound (881 mg, yield: 79%).

$^1$H-NMR Spectrum (400 MHz, CDCl$_3$) δ(ppm): 1.08 (3H, t, J=7.2 Hz), 2.10-2.50 (4H, m), 2.55-2.68 (2H, m), 2.70-2.90 (4H, m), 3.00-3.20 (2H, m), 3.23-3.40 (3H, m), 3.45-3.90 (9H, m), 4.03 (1H, dd, J=7.2 Hz, 7.6 Hz), 4.41 (214, d, J=6.4 Hz), 5.18-5.28 (2H, m), 5.30-5.44 (2H, m), 5.62-5.78 (2H, m), 6.14 (1H, d, J=8.4 Hz), 6.51 (1H, d, J=6.4 Hz), 6.70-6.87 (2H, m), 6.95 (1H, dd, J=8.0 Hz, 9.2 Hz), 7.14 (1H, d, J=11.6 Hz), 7.20-7.33 (2H, m), 7.33-7.44 (3H, m).

ESI-MS (m/z): 806.58 [M+H]$^+$.

Example 26

4-(((6S,9aS)-1-(Benzylcarbamoyl)-8-((6-(3-(4-ethylpiperazin-1-yl)azetidin-1-yl)pyridin-2-yl)methyl-4,7-dioxo-2-(prop-2-en-1-yl)-octahydro-1H-pyrazino[2,1-c][1,2,4]triazin-6-yl)methyl)phenyl dihydrogen phosphate

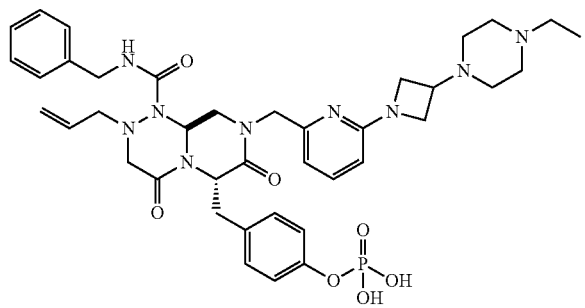

The title compound (183 mg, yield: 55%) was produced from (6S,9aS)-N-benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide (298 mg, 0.421 mmol) described in Example 2 employing the similar procedure as in Example 25.

$^1$H-NMR Spectrum (400 MHz, CDCl$_3$) δ(ppm): 1.10 (3H, t, J=7.6 Hz), 1.60-2.30 (4H, m), 2.60-2.80 (2H, m), 2.80-3.15 (4H, m), 3.20-3.42 (3H, m), 3.45-3.70 (7H, m), 3.78-4.10 (5H, m), 4.28-4.45 (2H, m), 5.06-5.38 (5H, m), 5.62-5.74 (1H, m), 6.20 (1H, d, J=8.4 Hz), 6.61 (1H, d, J=6.8 Hz), 6.70 (1H, dd, J=6.0 Hz, 6.0 Hz), 6.84 (2H, d, J=8.0 Hz), 7.09 (2H, d, J=8.0 Hz), 7.16-7.32 (3H, m), 7.32-7.46 (2H, m).

ESI-MS (m/z): 788.57 [M+H]$^+$.

Example 27

(6S,9aS)-N-Benzyl-8-((6-(3-((3S)-3,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

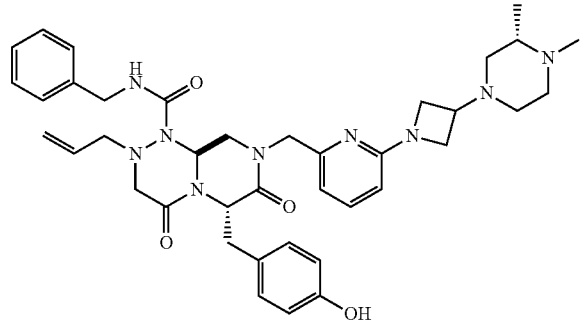

The title compound (33.0 mg, yield: 74%) was produced from (6S,9aS)-N-benzyl-8-((6-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide (35.0 mg, 0.0627 mmol) described in Production Example 2-4 and (2S)-4-(azetidin-3-yl)-1,2-dimethylpiperazine (106 mg, 0.314 mmol) described in Production Example 4-3 employing the similar procedure as in Example 2.

$^1$H-NMR Spectrum (400 MHz, CDCl$_3$) δ(ppm): 1.05 (3H, d, J=6.0 Hz), 1.50-1.85 (1H, m), 1.88-2.00 (1H, m), 2.23 (3H, s), 2.25-2.50 (3H, m), 2.70-2.82 (1H, m), 3.05-3.23 (2H, m), 3.28-3.38 (1H, m), 3.40-3.50 (2H, m), 3.52-3.70 (5H, m), 3.72-3.82 (1H, m), 3.82-3.90 (1H, m), 4.00-4.10 (2H, m), 4.15-4.28 (2H, m), 4.33-4.45 (1H, m), 4.99 (1H, d, J=13.2 Hz), 5.03-5.13 (1H, m), 5.15-5.30 (3H, m), 5.65-5.80 (1H, m), 6.29 (1H, d, J=7.6 Hz), 6.39 (2H, d, J=8.0 Hz), 6.56 (2H, d, J=8.4 Hz), 6.65-6.77 (2H, m), 7.16-7.25 (2H, m), 7.24-7.32 (1H, m), 7.34-7.40 (2H, m), 7.44-7.52 (1H, m).

ESI-MS (m/z): 708.56 [M+H]$^+$.

Example 28

(6S,9aS)-N-Benzyl-8-((6-(3-((3R)-3,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide

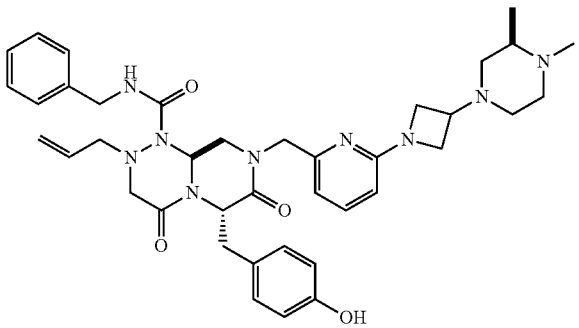

The title compound (23.0 mg, yield: 52%) was produced from (6S,9aS)-N-benzyl-8-((6-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide (35.0 mg, 0.0627 mmol) described in Production Example 2-4 and (2R)-4-(azetidin-3-yl)-1,2-dimethylpiperazine (106 mg, 0.314 mmol) described in Production Example 24-2-3 employing the similar procedure as in Example 2.

$^1$H-NMR Spectrum (400 MHz, CDCl$_3$) δ(ppm): 0.91 (3H, d, J=6.4 Hz), 1.60-2.00 (2H, m), 2.10-2.25 (1H, m), 2.30 (3H, s), 2.40-2.55 (2H, m), 2.80-2.95 (2H, m), 3.09 (1H, dd, J=4.8 Hz, 13.6 Hz), 3.15-3.25 (2H, m), 3.35-3.48 (2H, m), 3.50-3.78 (6H, m), 3.85-3.93 (1H, m), 4.03 (2H, d, J=6.4 Hz), 4.15-4.22 (1H, m), 4.30-4.42 (2H, m), 4.98 (1H, d, J=13.6 Hz), 5.18-5.30 (3H, m), 5.13-5.30 (1H, m), 6.28 (1H, d, J=8.0 Hz), 6.39 (2H, d, J=8.0 Hz), 6.60 (2H, d, J=8.0 Hz), 6.72 (2H, d, J=6.8 Hz), 7.20-7.28 (2H, m), 7.28-7.32 (1H, m), 7.33-7.40 (2H, m), 7.43-7.50 (1H, m).

ESI-MS (m/z): 708.70 [M+H]$^+$.

Example 29

(6S,9aS)-N-Benzyl-6-((4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide

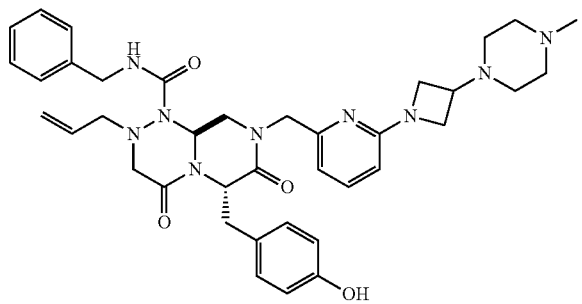

The title compound (14 mg, yield: 38%) was produced from (6S,9aS)-N-benzyl-8-((6-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide (30.0 mg, 0.0537 mmol) described in Production Example 2-4 and a mixture (87 mg) of 1-(azetidin-3-yl)-4-methylpiperazine and benzylbenzene described in Production Example 3-2 employing the similar procedure as in Example 2.

$^1$H-NMR Spectrum (400 MHz, CDCl$_3$) δ(ppm): 2.30-2.65 (11H, m), 3.05-3.15 (1H, m), 3.18-3.25 (1H, m), 3.43 (2H, d, J=16.8 Hz), 3.48-3.72 (5H, m), 3.78 (1H, dd, J=6.4 Hz, 10.0 Hz), 3.87 (1H, dd, J=7.2 Hz, 9.6 Hz), 3.95-4.10 (2H, m), 4.15-4.25 (2H, m), 4.39 (1H, dd, J=6.8 Hz, 15.2 Hz), 4.99 (1H, d, J=13.6 Hz), 5.03-5.12 (1H, m), 5.15-5.30 (3H, m), 5.65-5.80 (1H, m), 6.29 (1H, d, J=8.4 Hz), 6.39 (2H, d, J=8.4 Hz), 6.56 (2H, d, J=8.0 Hz), 6.67-6.79 (2H, m), 7.20 (2H, d, J=6.8 Hz), 7.30 (1H, d, J=7.2 Hz), 7.38 (2H, dd, J=7.2 Hz, 7.2 Hz), 7.48 (1H, dd, J=7.2 Hz, 8.0 Hz).

ESI-MS (m/z): 694.64 [M+H]$^+$.

Reference Example 7

4-(((6S,9aS)-1-(Benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate produced in Example 25 was dissolved in methanol and isopropanol and then crystallized by evaporative crystallization to give a single crystal of the compound. An X-ray diffraction experiment was carried out using the resultant single crystal. Crystallographic data and structure analysis data are shown in Table 2, and atomic coordinate data are shown in Table 3. The absolute structure of the title compound was determined from the results.

TABLE 2

| | |
|---|---|
| Temperature | 100 K |
| Wavelength | 0.7107 Å |
| Crystal system, space group | Orthorhombic system, P2$_1$2$_1$2$_1$ |
| Lattice constant | a = 12.9468(13) Å |
| | b = 22.869(3) Å |
| | c = 35.197(3) Å |

TABLE 2-continued

| | |
|---|---|
| Volume | 10421(2) Å$^3$ |
| Z value, calculated density | 8, 1.138 g/cm$^3$ |
| Crystal size | 1.00 × 0.30 × 0.30 mm |
| Total number of reflections/number of unique reflections | 98007/28649 [R(intensity) = 0.0803] |
| Integrity | 80.3% |
| Phase determination | Direct method (SHELX97) |
| Refinement method | Least square method with respect to F$^2$ |
| Data/parameter | 28649/1135 |
| Compatibility degree | 1.432 |
| R value (whole data) | 0.1102 |
| R value (I > 2σ(I)) | 0.1020 |
| Flack parameter | 0.03(10) |
| Maximum and minimum peak difference | 1.61 and −0.61 e/Å$^3$ |

TABLE 3

| Atom | X | y | z | Beq |
|---|---|---|---|---|
| P1 | 0.22234(6) | 0.38251(4) | 1.02549(2) | 2.25(2) |
| P2 | 0.32512(7) | 0.30387(3) | 0.92569(2) | 2.26(2) |
| F1 | 0.4191(3) | 0.59169(11) | 1.02897(8) | 4.12(5) |
| F2 | 0.3083(3) | 0.3996(2) | 0.78853(10) | 5.66(8) |
| O1 | 0.2310(3) | 0.31558(11) | 1.02242(7) | 3.18(5) |
| O2 | 0.2399(3) | 0.41207(10) | 0.98840(7) | 2.81(4) |
| O3 | 0.1257(3) | 0.4002(2) | 1.04576(8) | 3.80(6) |
| O4 | 0.3191(2) | 0.39571(9) | 1.05376(7) | 2.40(4) |
| O5 | 0.4814(4) | 0.73884(13) | 1.06753(13) | 4.95(8) |
| O6 | 0.5379(3) | 0.5895(2) | 1.16918(9) | 3.87(6) |
| O7 | 0.6929(3) | 0.53722(12) | 1.00665(8) | 3.27(5) |
| O8 | 0.3017(2) | 0.27330(10) | 0.96224(7) | 2.58(4) |
| O9 | 0.3168(3) | 037158(11) | 0.92926(7) | 3.20(5) |
| O10 | 0.4265(2) | 0.2892(2) | 0.90698(8) | 3.28(5) |
| O11 | 0.2326(2) | 0.28383(11) | 0.89774(7) | 2.44(4) |
| O12 | 0.2243(4) | 0.4451(2) | 0.70258(10) | 5.22(9) |
| O13 | 0.0128(4) | 0.2671(2) | 0.71820(12) | 5.43(9) |
| O14 | −0.0428(3) | 0.4552(2) | 0.84388(9) | 4.18(7) |
| O15 | 0.4986(5) | 0.2079(2) | 0.8593(2) | 6.34(11) |
| O16 | −0.0930(5) | 0.1662(2) | 0.6886(2) | 6.25(11) |
| O17 | 0.2815(7) | 0.7842(3) | 1.0760(3) | 9.8(3) |
| O18 | 0.0947(6) | 0.3995(3) | 1.1241(2) | 7.08(13) |
| O19 | 0.1129(12) | 0.4790(10) | 1.1796(5) | 26.1(11) |
| N1 | 0.5761(3) | 0.65699(13) | 1.07684(10) | 3.15(6) |
| N2 | 0.7111(4) | 0.6892(2) | 1.01973(12) | 4.11(8) |
| N3 | 0.7036(4) | 0.6299(2) | 1.02987(10) | 3.44(6) |
| N4 | 0.6828(3) | 0.5949(2) | 1.13256(9) | 2.90(5) |
| N5 | 0.7190(3) | 0.6124(2) | 0.96551(10) | 3.45(6) |
| N6 | 0.7146(3) | 0.47859(13) | 1.12094(8) | 2.58(5) |
| N7 | 0.6868(3) | 0.40412(11) | 1.07900(8) | 2.37(4) |
| N8 | 0.6136(2) | 0.36956(10) | 1.00168(7) | 2.01(4) |
| N9 | 0.6018(3) | 0.34302(12) | 0.92130(8) | 2.48(5) |
| N10 | 0.0996(4) | 0.4139(2) | 0.74283(10) | 3.87(7) |
| N11 | 0.0527(4) | 0.5270(2) | 0.76191(10) | 4.25(8) |
| N12 | 0.0262(4) | 0.4807(2) | 0.78709(10) | 4.11(8) |
| N13 | −0.0719(3) | 0.3400(2) | 0.74727(10) | 3.57(6) |
| N14 | −0.0007(4) | 0.5509(2) | 0.83309(10) | 3.84(7) |
| N15 | −0.1204(3) | 0.2845(2) | 0.81466(12) | 3.66(6) |
| N16 | −0.0632(3) | 0.2677(2) | 0.87552(12) | 3.89(7) |
| N17 | −0.0736(3) | 0.35284(13) | 0.95238(9) | 2.65(5) |
| N18 | −0.0585(3) | 0.4280(2) | 1.01814(9) | 2.82(5) |
| C1 | 0.3399(2) | 0.45232(13) | 1.06553(8) | 2.03(4) |
| C2 | 0.3664(3) | 0.4954(2) | 1.03944(10) | 2.57(5) |
| C3 | 0.3929(3) | 0.5495(2) | 1.05433(11) | 2.83(6) |
| C4 | 0.3922(3) | 0.5634(2) | 1.09257(11) | 2.84(6) |
| C5 | 0.3668(4) | 0.5178(2) | 1.11731(11) | 3.28(7) |
| C6 | 0.3396(3) | 0.4628(2) | 1.10410(9) | 2.76(5) |
| C7 | 0.4105(4) | 0.6247(2) | 1.10682(13) | 3.50(7) |
| C8 | 0.5217(3) | 0.6453(2) | 1.11250(12) | 3.24(6) |
| C9 | 0.5499(4) | 0.7051(2) | 1.0570(2) | 3.90(8) |
| C10 | 0.6120(6) | 0.7163(2) | 1.0220(2) | 4.92(11) |
| C11 | 0.6558(3) | 0.6140(2) | 1.06547(11) | 2.96(6) |
| C12 | 0.7331(3) | 0.6083(2) | 1.09723(12) | 3.19(6) |
| C13 | 0.5819(3) | 0.6061(2) | 1.14004(11) | 3.00(6) |
| C1A | 0.7962(5) | 0.7192(2) | 1.0410(2) | 4.59(10) |
| C15 | 0.8250(5) | 0.7739(3) | 1.0216(2) | 5.02(11) |
| C16 | 0.8265(7) | 0.8253(3) | 1.0382(3) | 6.1(2) |
| C17 | 0.7041(3) | 0.5897(2) | 0.99958(11) | 2.95(6) |

TABLE 3-continued

| Atom | X | y | z | Beq |
|---|---|---|---|---|
| CI8 | 0.7248(4) | 0.5748(2) | 0.93229(12) | 3.64(7) |
| C19 | 0.6190(4) | 0.5596(2) | 0.91520(13) | 3.61(7) |
| C20 | 0.5296(4) | 0.5593(2) | 0.9367(2) | 4.13(8) |
| C21 | 0.4356(5) | 0.5418(3) | 0.9203(3) | 5.72(13) |
| C22 | 0.4335(7) | 0.5245(4) | 0.8828(3) | 7.0(2) |
| C23 | 0.5230(7) | 0.5239(4) | 0.8609(2) | 5.8(2) |
| C24 | 0.6150(6) | 0.5421(3) | 0.8773(2) | 4.80(10) |
| C25 | 0.7441(3) | 0.5640(2) | 1.16079(11) | 3.11(6) |
| C26 | 0.7566(3) | 0.4989(2) | 1.15272(11) | 3.04(6) |
| C27 | 0.8072(5) | 0.4642(3) | 1.1790(2) | 4.39(9) |
| C28 | 0.8197(5) | 0.4059(3) | 1.1703(2) | 5.10(12) |
| C29 | 0.7808(4) | 0.3837(2) | 1.13708(11) | 3.20(6) |
| C30 | 0.7276(3) | 0.4221(2) | 1.11295(9) | 2.56(5) |
| C31 | 0.6457(3) | 0.34570(13) | 1.06995(9) | 2.29(5) |
| C32 | 0.5732(3) | 0.37504(12) | 1.04045(9) | 2.15(4) |
| C33 | 0.6031(3) | 0.43445(13) | 1.05912(9) | 2.38(5) |
| C34 | 0.5597(3) | 0.40909(13) | 0.97555(9) | 2.45(5) |
| C35 | 0.6066(3) | 0.40460(13) | 0.93616(9) | 2.60(5) |
| C36 | 0.6495(3) | 0.3024(2) | 0.95006(10) | 2.68(5) |
| C37 | 0.5985(3) | 0.30966(13) | 0.98811(9) | 2.41(5) |
| C38 | 0.6583(4) | 0.3356(2) | 0.88433(12) | 3.43(7) |
| C39 | 0.6107(7) | 0.3707(3) | 0.8525(2) | 5.32(13) |
| C40 | 0.2292(3) | 0.2956(2) | 0.85944(9) | 2.50(5) |
| C41 | 0.2745(4) | 0.3448(2) | 0.84311(11) | 3.14(6) |
| C42 | 0.2643(3) | 0.3513(2) | 0.80431(12) | 3.61(7) |
| C43 | 0.2127(4) | 0.3121(3) | 0.78028(11) | 3.77(8) |
| C44 | 0.1689(4) | 0.2641(2) | 0.79281(4) | 3.39(7) |
| C45 | 0.1742(3) | 0.2555(2) | 0.83699(10) | 2.84(6) |
| C46 | 0.2039(4) | 0.3209(3) | 0.73806(12) | 4.22(9) |
| C47 | 0.1054(4) | 0.3541(2) | 0.72612(11) | 3.79(8) |
| C48 | 0.1634(3) | 0.4543(3) | 0.72876(12) | 4.33(10) |
| C49 | 0.1539(4) | 0.5138(3) | 0.7461(2) | 4.58(10) |
| C50 | 0.0291(4) | 0.4209(2) | 0.77466(11) | 3.26(6) |
| C51 | −0.0772(4) | 0.3993(2) | 0.76231(11) | 3.33(6) |
| C52 | 0.0103(4) | 0.3169(2) | 0.73076(13) | 4.02(8) |
| C53 | −0.0283(5) | 0.5374(2) | 0.73249(13) | 3.93(8) |
| C54 | −0.0084(4) | 0.5947(3) | 0.7133(2) | 4.18(8) |
| C55 | −0.0153(4) | 0.6019(3) | 0.6762(2) | 4.54(10) |
| C56 | −0.0085(4) | 0.4939(2) | 0.82284(12) | 3.49(7) |
| C57 | −0.0469(4) | 0.5706(2) | 0.86781(13) | 3.88(8) |
| C58 | 0.0244(4) | 0.5685(2) | 0.90212(12) | 3.24(6) |
| C59 | 0.0123(4) | 0.6092(2) | 0.93148(13) | 3.71(7) |
| C60 | 0.0725(5) | 0.6060(3) | 0.9637(2) | 4.69(10) |
| C61 | 0.1455(4) | 0.5624(3) | 0.9671(2) | 4.88(11) |
| C62 | 0.1606(4) | 0.5226(2) | 0.9388(2) | 4.18(9) |
| C63 | 0.1002(4) | 0.5259(2) | 0.90656(13) | 3.41(7) |
| C64 | −0.1668(5) | 0.3054(3) | 0.7500(2) | 4.31(9) |
| C65 | −0.1730(4) | 0.2671(2) | 0.7847(2) | 3.60(7) |
| C66 | −0.2357(5) | 0.2169(3) | 0.7847(2) | 5.02(11) |
| C67 | −0.2466(5) | 0.1859(2) | 0.8184(2) | 5.29(12) |
| C68 | −0.1899(4) | 0.2027(2) | 0.8494(2) | 3.80(8) |
| C69 | −0.1275(4) | 0.2516(2) | 0.8462(2) | 3.58(7) |
| C70 | −0.0814(4) | 0.2561(2) | 0.91611(12) | 3.34(7) |
| C71 | −0.0222(3) | 0.3131(2) | 0.92553(11) | 3.07(6) |
| C72 | −0.0325(4) | 0.3292(2) | 0.88304(12) | 3.29(6) |
| C73 | −0.0220(3) | 0.4097(2) | 0.95049(11) | 2.87(6) |
| C74 | −0.0689(3) | 0.4520(2) | 0.97953(11) | 3.07(6) |
| C75 | −0.1122(3) | 0.3691(2) | 1.01965(11) | 2.81(6) |
| C76 | −0.0647(3) | 0.3288(2) | 0.99046(10) | 2.64(5) |
| C77 | −0.0963(3) | 0.4678(2) | 1.0486(2) | 3.58(7) |
| C78 | −0.0344(5) | 0.5233(2) | 1.0504(2) | 4.91(11) |
| C79 | 0.4788(8) | 0.2282(3) | 0.8201(3) | 6.8(2) |
| C80 | −0.1914(5) | 0.1814(3) | 0.6753(2) | 4.77(10) |
| C81 | −0.1845(7) | 0.2308(4) | 0.6471(2) | 6.1(2) |
| C82 | −0.2448(7) | 0.1290(4) | 0.6581(2) | 7.7(3) |
| C83 | 0.2174(13) | 0.7528(6) | 1.1004(5) | 14.2(7) |
| C84 | 0.284(3) | 0.7610(8) | 1.1401(4) | 16.0(9) |
| C85 | 0.1134(11) | 0.7816(6) | 1.1022(5) | 12.2(6) |
| H2 | 0.3665 | 0.4881 | 1.0129 | 3.08 |
| H5 | 0.3681 | 0.5247 | 1.1439 | 3.93 |
| H5A | 0.7255 | 0.6505 | 0.9629 | 4.14 |
| H6 | 0.3211 | 0.4327 | 1.1214 | 3.31 |
| H7A | 0.3743 | 0.6288 | 1.1314 | 4.2 |
| H7B | 0.3769 | 0.652 | 1.0888 | 4.2 |
| H8 | 0.5161 | 0.6841 | 1.1255 | 3.89 |
| H10A | 0.5709 | 0.7034 | 0.9998 | 5.91 |
| H10B | 0.6219 | 0.7591 | 1.0196 | 5.91 |
| H11 | 0.6213 | 0.5752 | 1.062 | 3.55 |
| H12A | 0.7831 | 0.577 | 1.091 | 3.83 |
| H12B | 0.7718 | 0.6455 | 1.0999 | 3.83 |
| H14 | 0.0327 | 0.5757 | 0.8185 | 4.61 |
| H14A | 0.773 | 0.728 | 1.0672 | 5.51 |
| H14B | 0.857 | 0.6931 | 1.0426 | 5.51 |
| H15 | 0.8437 | 0.7718 | 0.9956 | 6.03 |
| H16A | 0.8082 | 0.8287 | 1.0642 | 7.37 |
| H16B | 0.8458 | 0.859 | 1.0242 | 7.37 |
| H18A | 0.7604 | 0.5381 | 0.9394 | 4.37 |
| H18B | 0.7671 | 0.5945 | 0.9126 | 4.37 |
| H20 | 0.5317 | 0.5709 | 0.9627 | 4.95 |
| H21 | 0.374 | 0.5418 | 0.9349 | 6.86 |
| H22 | 0.3698 | 0.5129 | 0.8718 | 8.46 |
| H23 | 0.5211 | 0.5112 | 0.8352 | 7.01 |
| H24 | 0.6762 | 0.5427 | 0.8624 | 5.76 |
| H25A | 0.7111 | 0.5689 | 1.186 | 3.74 |
| H25B | 0.8134 | 0.5822 | 1.1621 | 3.74 |
| H27 | 0.8324 | 0.48 | 1.2022 | 5.27 |
| H28 | 0.8555 | 0.3809 | 1.1874 | 6.12 |
| H29 | 0.7895 | 0.3437 | 1.1306 | 3.84 |
| H31A | 0.6089 | 0.3268 | 1.0913 | 2.75 |
| H31B | 0.6973 | 0.3189 | 1.0586 | 2.75 |
| H32 | 0.4987 | 0.3643 | 1.0432 | 2.58 |
| H33A | 0.6271 | 0.4643 | 1.0408 | 2.86 |
| H33B | 0.5494 | 0.4505 | 1.0762 | 2.86 |
| H34A | 0.5654 | 0.4498 | 0.9849 | 2.94 |
| H34B | 0.4856 | 0.3986 | 0.9745 | 2.94 |
| H35A | 0.5688 | 0.4309 | 0.9186 | 3.12 |
| H35B | 0.6795 | 0.4176 | 0.9371 | 3.12 |
| H36A | 0.6415 | 0.2614 | 0.9414 | 3.22 |
| H36B | 0.7242 | 0.3108 | 0.9524 | 3.22 |
| H37A | 0.5238 | 0.3013 | 0.9859 | 2.9 |
| H37B | 0.6288 | 0.2817 | 1.0065 | 2.9 |
| H38A | 0.6581 | 0.2937 | 0.8772 | 4.11 |
| H38B | 0.731 | 0.3478 | 0.8877 | 4.11 |
| H39A | 0.6137 | 0.4124 | 0.8588 | 6.38 |
| H39B | 0.5385 | 0.3588 | 0.8491 | 6.38 |
| 1139C | 0.649 | 0.3636 | 0.8289 | 6.38 |
| H41 | 0.3108 | 0.3727 | 0.858 | 3.77 |
| H44 | 0.1337 | 0.236 | 0.783 | 4.07 |
| 1145 | 0.1411 | 0.2228 | 0.8484 | 3.4 |
| H46A | 0.2045 | 0.2823 | 0.7254 | 5.06 |
| H46B | 0.265 | 0.343 | 0.7291 | 5.06 |
| H47 | 0.1125 | 0.3603 | 0.6981 | 4.55 |
| H49A | 0.206 | 0.5174 | 0.7666 | 5.5 |
| H49B | 0.1705 | 0.5434 | 0.7266 | 5.5 |
| 1150 | 0.0538 | 0.396 | 0.7962 | 3.91 |
| H51A | −0.1248 | 0.4001 | 0.7843 | 4 |
| H51B | −0.1053 | 0.4258 | 0.7426 | 4 |
| H53A | −0.0974 | 0.5379 | 0.7446 | 4.72 |
| H53B | −0.027 | 0.5055 | 0.7135 | 4.72 |
| H54 | 0.0101 | 0.6274 | 0.7286 | 5.01 |
| H55A | −0.0337 | 0.5699 | 0.6604 | 5.45 |
| H55B | −0.0019 | 0.6392 | 0.6653 | 5.45 |
| H57A | −0.1085 | 0.5462 | 0.8731 | 4.66 |
| H57B | −0.0708 | 0.6114 | 0.8643 | 4.66 |
| H59 | −0.0378 | 0.6393 | 0.9292 | 4.45 |
| H60 | 0.0638 | 0.6338 | 0.9835 | 5.63 |
| 1161 | 0.1859 | 0.56 | 0.9896 | 5.85 |
| H62 | 0.2118 | 0.4931 | 0.9413 | 5.02 |
| H63 | 0.1108 | 0.4983 | 0.8868 | 4.1 |
| H64A | −0.1724 | 0.2804 | 0.7271 | 5.17 |
| H64B | −0.2266 | 0.3323 | 0.75 | 5.17 |
| H66 | −0.2698 | 0.2045 | 0.7622 | 6.02 |
| H67 | −0.2926 | 0.1537 | 0.8199 | 6.35 |
| H68 | −0.1933 | 0.1813 | 0.8725 | 4.56 |
| H70A | −0.0472 | 0.2202 | 0.9256 | 4.01 |
| H7013 | −0.1552 | 0.2569 | 0.9235 | 4.01 |
| H71 | 0.0511 | 0.3053 | 0.9329 | 3.69 |
| H72A | −0.0874 | 0.3582 | 0.8777 | 3.95 |
| H72B | 0.0335 | 0.3407 | 0.8709 | 3.95 |
| H73A | −0.0295 | 0.4262 | 0.9246 | 3.44 |
| H73B | 0.0526 | 0.4048 | 0.9557 | 3.44 |
| H74A | −0.0331 | 0.4902 | 0.978 | 3.69 |
| H74B | −0.1428 | 0.4584 | 0.9736 | 3.69 |
| H75A | −0.1048 | 0.352 | 1.0453 | 3.37 |
| H75B | −0.1868 | 0.3741 | 1.0143 | 3.37 |
| H76A | 0.0092 | 0.3227 | 0.9966 | 3.16 |

TABLE 3-continued

| Atom | x | y | z | Beq |
|---|---|---|---|---|
| H76B | −0.0997 | 0.2904 | 0.9914 | 3.16 |
| H77A | −0.0921 | 0.4475 | 1.0734 | 4.3 |
| H77B | −0.1697 | 0.4775 | 1.0438 | 4.3 |
| H78A | −0.0394 | 0.5439 | 1.0261 | 5.9 |
| H78B | 0.0381 | 0.514 | 1.0556 | 5.9 |
| H78C | −0.0615 | 0.5483 | 1.0707 | 5.9 |
| H80 | −0.2334 | 0.1951 | 0.6974 | 5.72 |
| H81A | −0.1421 | 0.2186 | 0.6254 | 7.36 |
| H81B | −0.153 | 0.2649 | 0.6592 | 7.36 |
| H81C | −0.254 | 0.2409 | 0.6382 | 7.36 |
| H82A | −0.251 | 0.0981 | 0.6773 | 9.25 |
| H82B | −02044 | 0.1145 | 0.6365 | 9.25 |
| H82C | −0.3139 | 0.1403 | 0.6493 | 9.25 |
| H83 | 0.2121 | 0.7108 | 1.0928 | 17.04 |
| H84A | 0.2873 | 0.8026 | 1.1466 | 19.21 |
| H84B | 0.3538 | 0.7457 | 1.1365 | 19.21 |
| H84C | 0.2495 | 0.7395 | 1.1606 | 19.21 |
| H85A | 0.0801 | 0.7793 | 1.0772 | 14.65 |
| H85B | 0.1217 | 0.8227 | 1.1095 | 14.65 |
| H85C | 0.0705 | 0.7616 | 1.1211 | 14.65 |

Test Example 1

Detection of Wnt Signal pcDNA3.1(+) (invitrogen) was cleaved with restriction enzymes BglII and NotI, and an adapter BEHKS having a sequence shown below (containing restriction enzyme sites BglII, EcoRI, HindIII, KpnI, SacI and NotI) was inserted thereinto, thereby producing a plasmid pNeo-HKS.

```
BEHKS-F
                                          (SEQ ID NO: 1)
5'-gatctgaattcaagcttctcgagggtacctctagagagctcgc-3'

BEHKS-R
                                          (SEQ ID NO: 2)
5'-ggccgcgagctctctagaggtaccctcgagaagcttgaattca-3'
```

Subsequently, a fragment having a length of about 2700 bp (containing a Wnt-responsive sequence and a luciferase gene), which was prepared by cleaving from a TOPglow plasmid contained in a TOPglow/FOPglow TCF Reporter Kit (upstate Catalog#17-366) with restriction enzymes HindIII and KpnI, was inserted between HindIII and KpnI in pNeo-HKS, thereby producing a plasmid pNeo-TOP. The plasmid pNeo-TOP was introduced into human fetus-derived renal cell strain HEK293, then a compound was selected using G418, and then a cell clone strain was established by a limiting dilution method. The cell clone strain was subjected to a Wnt signal detection test.

The cell clone strain was subcultured in a D-MEM glucose-rich culture medium (Wako Pure Chemical Industries, Ltd.) containing 10% FBS, and cells in a growth phase were used in the test. Cells were collected using trypsin-EDTA, the number of the cells was counted, and then the cells were suspended in a D-MEM glucose-rich culture medium containing 10% FBS so that the number of cells became $2\times10^5$ cells/mL. The cell suspension was added to a 96-well cell culture plate (Greiner Bio-One Co., Ltd., product number: 655083) in an amount of 0.1 mL/well and then cultured overnight in a 5% $CO_2$ incubator (37° C.). After the culturing, a substance to be tested, which was dissolved in DMSO, was diluted with a D-MEM glucose-rich culture medium containing 10% of FBS and 80 mM of LiCl to produce a sample solution. The sample solution (0.1 mL) was added to each well and then cultured in a 5% $CO_2$ incubator (37° C.) overnight. Six hours after the addition of the sample solution, a supernatant was removed from each well, and then 50 µL of Bright-Glo™ Luciferase substrate (Promega, product number: E2620) was added thereto. The plate was put on a plate mixer for several seconds, and then the emission of light from each well was measured using a EnVision™ Multilabel plate reader (PerkinElmer Co., Ltd.). The Wnt signal activation rate (%) of each well was determined, and a concentration ($IC_{50}$) which is required for inhibiting the Wnt signal activity of a substance of interest by 50% was calculated, wherein the luminosity of a well to which a sample solution was not added and LiCl was added was defined as a 100% Wnt signal activity and the luminosity of a well to which either of a sample solution or LiCl was not added was defined as a 0% Wnt signal activity. From the results of the test, it was demonstrated that the compound according to the present invention inhibited a Wnt signal and was applicable as a therapeutic agent for diseases including cancer and fibrosis.

Test Example 2

Evaluation of Metabolic Stability

A test substance was dissolved in DMSO so that the concentration of the resultant solution became 20 mM, and the solution was diluted with DMSO so that the concentration of the resultant solution became 1 mM. The metabolic stability of the test substance was evaluated using a human liver microsome (HLM) in which human liver was pooled. An assay buffer solution contained 0.2 mg/mL of HLM, a 0.1 M of phosphate potassium buffer solution (pH 7.4), 0.1 mM of EDTA, 0.33 mM of NADP+, 8 mM of glucose-6-phosphate, 0.1 U/mL of glucose-6-phosphate dehydrogenase, 6 mM of $MgCl_2$, 0.1 µM of a test substance (final concentration in DMSO: 0.01%) in 0.15 mL of the final incubation volume. Fifteen minutes after the initiation of the reaction at 37° C., 0.15 mL of a acetonitrile/methanol mixed solution (7:3, by volume) was added to the solution to terminate the reaction. After centrifugation, the resultant supernatant was analyzed by LC-MSMS, peak areas were compared under the presence or absence of the production of NADPH, and the residual ratio of the test substance was calculated.

Test Example 3

Evaluation of Solubility

To 0.25 mL of a test solution a mentioned below was added 2.5 µL of a DMSO solution having a compound concentration of 20 mM. The resultant solution was shaken at room temperature for about 15 minutes (the conditions for the shaking are mentioned below). Subsequently, a supernatant was collected by a suction filtration under a reduced pressure. A DMSO solution having a compound concentration of 200 µM was used as a standard solution, and the concentration of a compound in a filtrate which was quantified by a HPLC-UV method was employed as a solubility (rounded off to the whole number). In this evaluation, since a value 200 µM became the upper limit operationally, all of quantification values greater than 200 µM were regarded as 200 µM.
Test solution: GIBCO (registered trade name) Dulbecco's phosphate-buffered saline (pH 7, Life Technologies Corporation)
Conditions for shaking: a microplate shaker N-704 (Nissinrika Corporation), speed 6

Test Example 4

PAMPA Test (Parallel Artificial Membrane Permeability Assay)

A test solution (see below) was stirred while shaking at room temperature for about 5 hours using a 96-well PAMPA plate (BD Biosciences) in which a lipid had been precoated onto a polyvinylidene fluoride (PVDF) film to evaluate the membrane permeation coefficient $P_e$ (cm/s) of each compound dissolved in the test solution (concentration: about 200 µM) upon the transport of the compound from a donor side to an acceptor side through a lipid membrane. The $P_e$ value was calculated in accordance with equations 1 and 2, and the concentration of the compound on the donor side and the acceptor side was measured by a HPLC-UV method. In 0.3 mL of the test solution on the donor side is contained about 1% (v/v) of DMSO, since 3 µL of a DMSO solution containing the compound at a concentration of 20 mM was added to the test solution.

Test solution: a phosphate buffer solution having a pH value of 6.8 (90 mM of phosphate, 48 mM of NaCl, 5.4 mM of KCl)

Conditions for stirring: a multishaker MS-300 (AS ONE Corporation), 350 rpm $$P_e = \frac{-\ln[1 - C_A(t)/C_{equilibrium}]}{A*(1/V_D + 1/V_A)*t} \quad \text{(Eq. 1)}$$

$$C_{equilibrium} = \frac{C_D(t)*V_D + C_A(t)*V_A}{V_D + V_A} \quad \text{(Eq. 2)}$$

$C_D(t)$: compound concentration in donor well at time t
$C_A(t)$: compound concentration in acceptor well at time t
$V_D$: donor well volume (0.3 mL)
$V_A$: acceptor well volume (0.2 mL)
A: filter area (0.3 cm$^2$)

The No. 199 compound in Table 3 in Patent Literature 1 was used in Comparative Example 1 and the compounds described in Examples I-5 and I-7 in Patent Literature 3 were used in Comparative Examples 2 and 3, respectively, and the results of the test on these compounds are also shown.

Comparative Example 1

(6S,9aS)-N-Benzyl-6-(4-hydroxybenzyl)-4,7-dioxo-8-((2-(4-(pyrrolidin-1-yl)piperidin-1-yl)pyridin-3-yl)methyl)-2-(prop-2-en-1-yl)-octahydro-1H-pyrazino[2,1-c][1,2,4]triazine-1-carboxamide

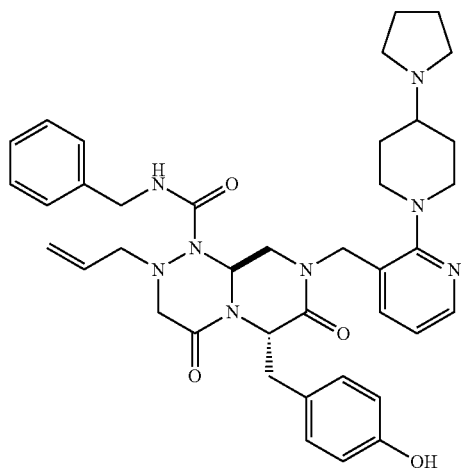

Comparative Example 2

(6S,9S)-N-Benzyl-6-(4-hydroxybenzyl)-2,9-dimethyl-4,7-dioxo-8-(quinolin-8-ylmethyl)octahydro-1H-pyrazino[2,1-c][1,2,4]triazine-1-carboxamide

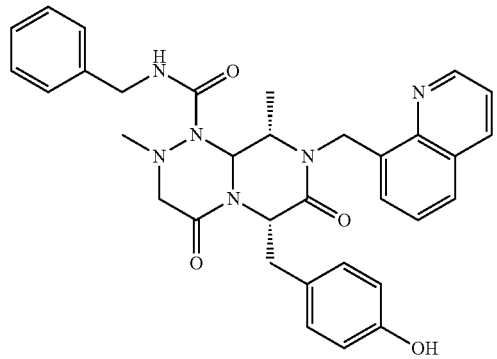 [SMILES: C[C@H]1C2N(C(=O)CN(C)N2C(=O)NCc2ccccc2)[C@@H](Cc2ccc(O)cc2)C(=O)N1Cc1cccc2cccnc12]

Comparative Example 3

4-(((6S,9S)-1-(Benzylcarbamoyl)-2,9-dimethyl-4,7-dioxo-8-(quinolin-8-ylmethyl)octahydro-1H-pyrazino[2,1-c][1,2,4]triazin-6-yl)methyl)phenyl dihydrogen Phosphate

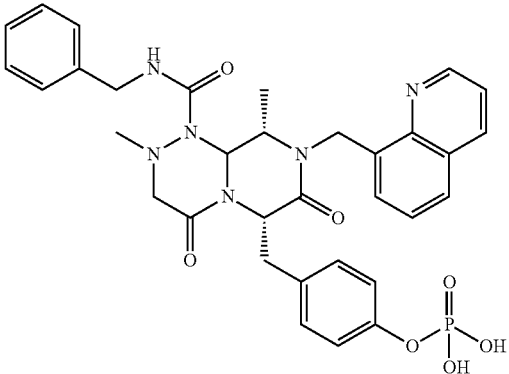 [SMILES: C[C@H]1C2N(C(=O)CN(C)N2C(=O)NCc2ccccc2)[C@@H](Cc2ccc(OP(=O)(O)O)cc2)C(=O)N1Cc1cccc2cccnc12]

The results of the test on the compounds in Examples, Reference Examples and Comparative Examples in Test Examples 1 to 4 are shown in Table 4.

TABLE 4

| | Test Example 1 IC$_{50}$ (µM) | Test Example 2 (%) | Test Example 3 (µM) | Test Example 4 Pe (×10$^{-6}$ cm/sec) |
|---|---|---|---|---|
| Example 1 | 0.06 | 47 | 197 | 2.01 |
| Example 2 | 0.29 | 58 | 200 | 1.32 |
| Example 3 | 0.15 | 54 | 200 | 1.33 |
| Example 4 | 0.06 | 44 | 199 | 2.03 |
| Example 5 | 0.082 | 39 | 200 | 1.18 |
| Example 6 | 0.25 | 55 | 195 | 1.27 |
| Example 7 | 0.095 | 29 | 189 | 2.77 |
| Example 8 | 0.2 | 40 | 195 | 2.3 |
| Example 9 | 0.15 | 34 | 194 | 1.38 |
| Example 10 | 0.044 | 28 | 184 | 3.75 |
| Example 11 | 0.039 | 26 | 192 | 2.55 |

TABLE 4-continued

| | Test Example 1 IC$_{50}$ (μM) | Test Example 2 (%) | Test Example 3 (μM) | Test Example 4 Pe (×10$^{-6}$ cm/sec) |
|---|---|---|---|---|
| Example 12 | 0.096 | 38 | 188 | 0.87 |
| Example 13 | 0.14 | 56 | 200 | 0.52 |
| Example 14 | 0.27 | 69 | 197 | 0.39 |
| Example 15 | 0.075 | 45 | 195 | 2.38 |
| Example 16 | 0.22 | 63 | 197 | 0.51 |
| Example 17 | 0.21 | 60 | 195 | 0.89 |
| Example 18 | 0.32 | 37 | 200 | 1.13 |
| Example 19 | 0.23 | 30 | 200 | 0.91 |
| Example 20 | 0.061 | 23 | 197 | 2.17 |
| Example 21 | 0.063 | 23 | 200 | 1.47 |
| Example 22 | 0.18 | 43 | 200 | 0.57 |
| Example 23 | 0.19 | 38 | 195 | 0.43 |
| Example 24 | 0.077 | 26 | 200 | 1.91 |
| Reference Example 1 | 0.24 | 54 | 193 | 0.62 |
| Reference Example 2 | 0.33 | 51 | 195 | 0.65 |
| Reference Example 3 | 0.11 | 50 | 199 | 0.55 |
| Reference Example 4 | 0.15 | 34 | 198 | 0.68 |
| Reference Example 5 | 0.13 | 22 | 181 | 2.25 |
| Reference Example 6 | 0.19 | 28 | 190 | 1.7 |
| Example 25 | 0.18 | | | |
| Example 26 | 1.19 | | | |
| Example 27 | 0.4 | 57 | 199 | 1.04 |
| Example 28 | 0.38 | 55 | 198 | 0.95 |
| Example 29 | 0.47 | 63 | 200 | |
| Comparative Example 1 | 23.2 | 52.9 | 97 | 1.34 |
| Comparative Example 2 | 0.33 | 0.6 | 122 | 0.85 |
| Comparative Example 3 | | | | |

Test Example 5

Evaluation of Solubility (Examples 25 and 26)

About 10 mg of a sample was weighed accurately and placed in a 10-mL polypropylene test tube, a test solution shown below was added thereto by portions (0.1 mL) until the sample was dissolved completely. When the test solution was added, the mixed solution was stirred intermittently in a range from about 30 seconds to 3 minutes using a Vortex mixer every time the test solution was added. The solubility (mM) of the sample was calculated from the added amount of the test solution required until the presence of any solid material was not observed by visual judgment.

Test solution: GIBCO (registered trade name) (Dulbecco's phosphate-buffered saline having a pH value of 7, Invitrogen Corporation)

The values of solubility of Examples 25 and 26 are shown in Table 5.

TABLE 5

| Examples | Solubility |
|---|---|
| 25 | 124 mM or more |
| 26 | 42 mM or more and less than 62 mM |

Test Example 6

Effect of Regressing Small Intestinal Polyps in APC$^{Min/+}$ Mouse

An APC gene (an adenomatous polyposis coli gene), a Wnt signal degradation regulation factor, is called "colorectal cancer suppressor gene" and is a causal gene of familial adenomatous polyposis. If a mutation occurs in the APC gene, a colorectal mucosal cell begins to proliferate disorderly to form colorectal polyps that can be called a precancerous lesion. Thus, it is known that the gene has an important role in the initial stage of a process of onset of colorectal cancer.

In a mouse in which the APC gene is mutated (a APC$^{Min/+}$ mouse), many polyps are developed in the intestinal tract like a familial adenomatous polyposis patient. Therefore, the mouse is useful for the clarification of the mechanism of the onset or invasion of cancer based on a WNT signal, and is a standard model that has been used for the studies on the prevention, diagnosis and treatment of colorectal cancer.

APC$^{Min/+}$ mice (C57BL/6J-APC<Min>/J Hetero, female, Sunplanet Co., Ltd.) were grouped so that the average of the body weights of mice in a group became almost the same as one another at the first day of the administration. An analyte was prepared by being dissolved a test substance (Example compound) in 0.1 N HCl so that the concentration became a desired administration concentration, and then stored in a refrigerator at 4° C. To a control (vehicle) group, an administration solvent was administered orally under the same conditions as a test material. The analyte was continuously administered through an oral route at dosages of 50 mg/kg and 75 mg/kg two times daily for 4 days, and the following three days were provided as drug holidays. This procedure was defined as one cycle, and the administration was performed for 16 days in total (i.e., 4 days×4 cycles). The experiment was carried out on 6 to 7 mice per group. With respect to each of the control group and the test substance-administered group, the value of the body weight on the final day to the body weight on the first day (i.e., a relative body weight: RBW) was calculated. A test substance-administered group of which the (RBW of the test substance-administered group)/(RBW of the control group) was 0.8 or more was determined as a group that could be administered safely. With respect to the test substance-administered group, the actual number of polyps after the administration of the test substance and the standard error of the actual number compared with the number of polyps in the control on the final day (i.e., the 25$^{th}$ day counted from the first day of the administration) are shown in FIG. 1. In this test, polyps formed in the small intestine and the colon were counted. A statistical analysis (Dunnett's test) of the test substance-administered group relative to the control group was carried out, and a P value was reported.

Test Example 7

Anti-Tumor Effect in Human K562 Subcutaneous Transplantation Model

A preparation of a human chronic myelogenous leukemia cell strain K562 (which had been cultured in a RPMI-1640 liquid culture medium supplemented with 10% FBS and penicillin/streptomycin) which was so prepared with PBS (Wako Pure Chemical Industries, Ltd.; Cat#045-29795) that the density became 2×10$^8$ cells/mL was mixed with MATRI-GEL (BD Bioscience, Cat#: 354234) at a mixing ratio of 1:1, thereby preparing a cell suspension having a density of 1×10$^8$ cells/mL. The resulting cell suspension was transplanted subcutaneously into the right flank of each of six-week-old nude mice (CAnN.Cg-Foxn1nu/CrlCrlj, female, Charles River Laboratories Japan) at a dose of 100 µL. Seven days after the transplantation, the shorter diameter and the longer diameter of a tumor were measured using an electronic digital caliper (Digimatic™ Caliper, Mitutoyo Corporation) to calculate the tumor volume in accordance with the following equation.

Tumor volume (mm$^3$)=(longer diameter (mm))×(shorter diameter (mm))×(shorter diameter (mm))/2

Figure 2:
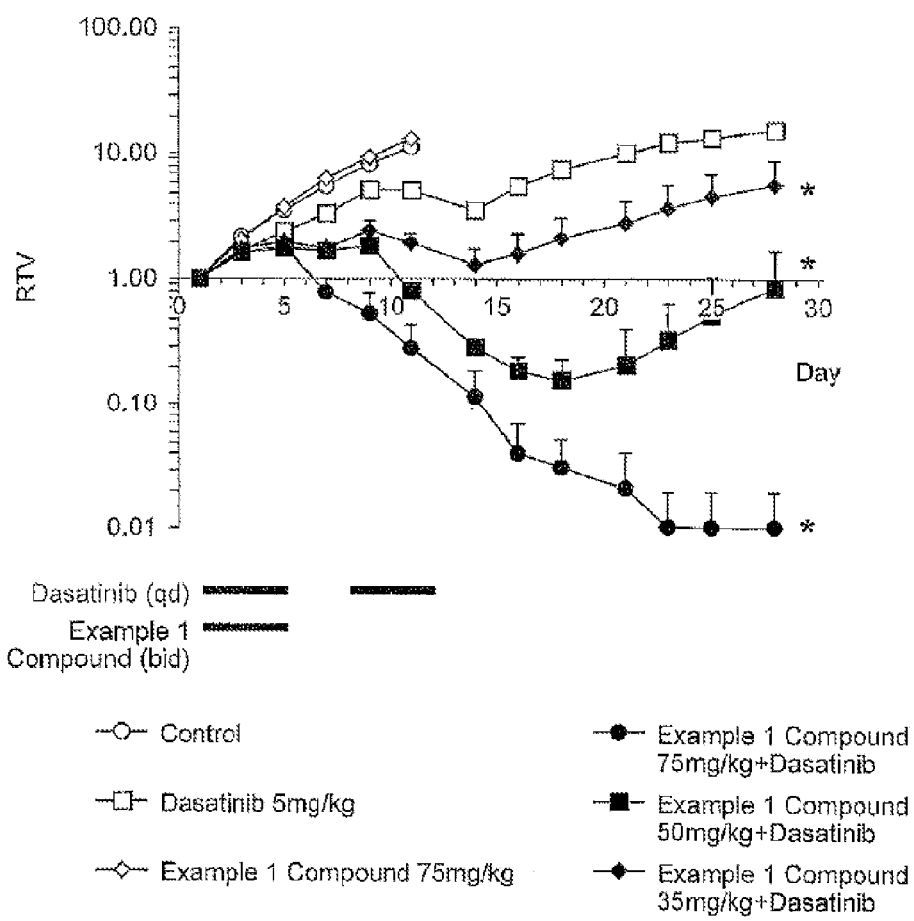
FIG. 2 shows the results of Test Example 7.
Figure 3:
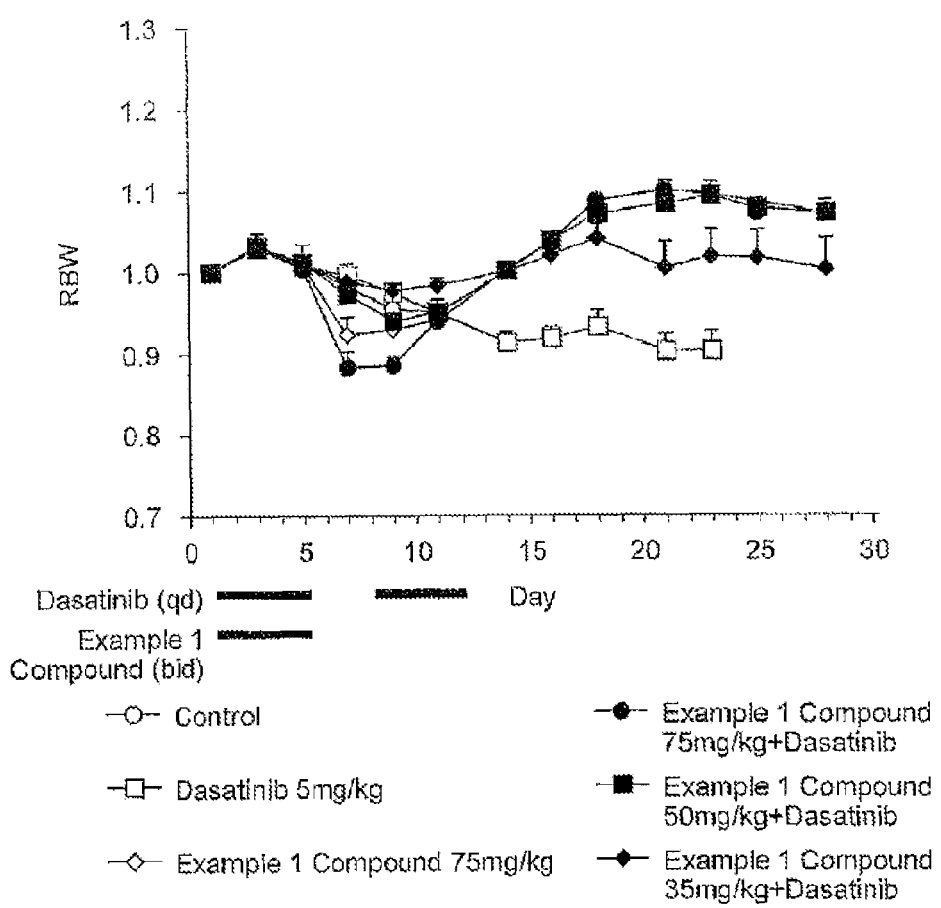
FIG. 3 shows the results of Test Example 7.

The mice were grouped in such a manner that the average value of the tumor volumes in mice in a group, which were determined on the basis of the tumor volume on the first day of the administration. An analyte was prepared by being dissolved a Example compound in 0.1 N HCl so that the dose amount became 10 mL/kg. A Dasatinib administration solution was prepared by dissolving Dasatinib, Free Base (LC Laboratories, Cat. No: D-3307) in a 1:1 solution of Otsuka distilled water (Otsuka Pharmaceutical Co., Ltd., Cat#: 1324) and PROPYLENE GLYCOL (Wako Pure Chemical Industries, Ltd., Cat#: 164-04996) so that the dosage amount became 10 mL/kg. A Example compound was administered orally continuously for 5 days starting from the first day of the administration in two divided doses daily (bid). Dasatinib was administered orally once daily (qd) for 5 days continuously, and the following two-day drug holidays was set. This procedure was defined as one cycle, and the administration was performed in two cycles in total. A control group was a group to which any example compound was not administered. In the experiment, one group includes 9 to 10 mice. With respect to the control group, a group to which only a Example compound was administered, a group to which only Dasatinib was administered, and an a group to which both a Example compound and Dasatinib were administered (hereinafter referred as combined administered group), the tumor volumes and body weights were measured over time for a period from the first day to the 28$^{th}$ day. With respect to the control group and the group to which only the Example compound was administered, the measurement was carried out for a period from the first day to the 11$^{th}$ day. In every measurement, a tumor volume (a relative tumor volume: RTV) and a body weight (a relative body weight: RBW) were calculated relative to the values for the first day, and graphs determined for a period from the first day of the administration to the 28$^{th}$ day are shown in FIGS. 2 and 3. Further, a statistic analysis (Dunnett's test) was carried out on the group to which both the Example compound and Dasatinib were administered compared with the group to which only Dasatinib was administered using a RTV value on day 28, and a group of which the P value was 0.05 or less was marked with an asterisk (*). Further, the number of individuals in which a tumor was not observed by visual judgment and was impalpable (i.e., having a non-palpable tumor) on day 28 are also shown in Table 6. At this time, a statistic analysis (Fisher's test) was carried out on the group to which both the Example compound and Dasatinib were administered compared with the group to which only Dasatinib was administered, and a group of which P value was 0.05 or less was marked with an asterisk (*) and a group in which P value is 0.01 or less was marked with asterisks (***).

TABLE 6

| Admistered compound | the number of individuals in which a tumor was not observed by visual judgment/total number of mice |
|---|---|
| Control | 0/10 |
| Dasatinib 5 mg/kg | 0/9 |
| Dasatinib 5 mg/kg +Compound of Example 1 75 mg/kg | 10/10*** |
| Dasatinib 5 mg/kg +Compound of Example 1 50 mg/kg | 9/10*** |
| Dasatinib 5 mg/kg +Compound of Example 1 35 mg/kg | 6/10* |

Sequence Listing

The invention claimed is:
1. A compound represented by formula (1) or pharmaceutically acceptable salt thereof:

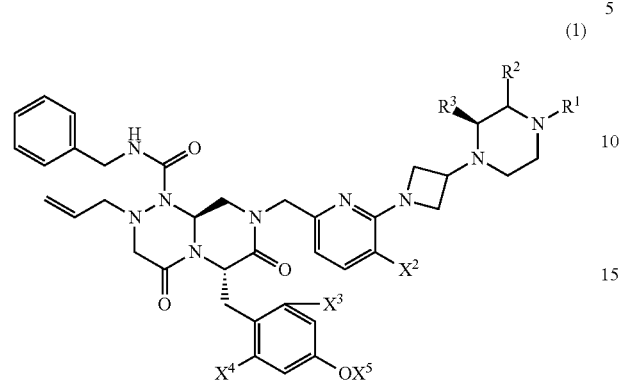

wherein $R^1$ is a $C_{1-6}$ alkyl group; $R^2$ and $R^3$ are the same or different from each other and each is a hydrogen atom or a $C_{1-6}$ alkyl group; $X^2$, $X^3$ and $X^4$ are the same or different from each other and each is a hydrogen atom or a halogen atom; and $X^5$ is a hydrogen atom or $-P(=O)(OH)_2$.

2. The compound or pharmaceutically acceptable salt thereof according to claim 1, wherein R is a methyl group, an ethyl group or an isopropyl group.

3. The compound or pharmaceutically acceptable salt thereof according to claim 1, wherein $R^2$ and $R^3$ are the same or different from each other and each is a hydrogen atom or a methyl group.

4. The compound or pharmaceutically acceptable salt thereof according to claim 1, wherein $X^2$ is a hydrogen atom or a fluorine atom.

5. The compound or pharmaceutically acceptable salt thereof according to claim 1, wherein $X^3$ is a hydrogen atom or a fluorine atom.

6. The compound or pharmaceutically acceptable salt thereof according to claim 1, wherein $X^4$ is a hydrogen atom or a fluorine atom.

7. A compound or pharmaceutically acceptable salt thereof selected from:
- (6S,9aS)-N-benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-6-((2-fluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-((3-((3S)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-(3-((3R)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-(3-((2S)-2,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-(3-(4-ethylpiperazin-1-yl)azetidin-1-yl)-5-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((5-fluoro-6-(3-(4-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-6-((4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide,
- (6S,9aS)-N-benzyl-6-((2-fluoro-4-hydroxyphenyl)methyl)-8-((5-fluoro-6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide,
- (6S,9aS)-N-benzyl-6-((2-fluoro-4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide,
- (6S,9aS)-N-benzyl-6-((2,6-difluoro-4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide,
- (6S,9aS)-N-benzyl-6-((2,6-difluoro-4-hydroxyphenyl)methyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide,
- (6S,9aS)-N-benzyl-6-((2,6-difluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-(3-((2S)-2,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-6-((2,6-difluoro-4-hydroxyphenyl)methyl)-8-((6-(3-((3S)-3,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide,
- (6S,9aS)-N-benzyl-6-((2,6-difluoro-4-hydroxyphenyl)methyl)-8-((6-(3-((2S)-2,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-(3-((3S)-4-ethyl-3-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide,
- (6S,9aS)-N-benzyl-8-((6-3-((3R)-4-ethyl-3-methylpiperazin-1-yl)azetidin-1-yl)pyridin-2-yl)methyl-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3S)-4-ethyl-3-methylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3R)-4-ethyl-3-methylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3S)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3R)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3R)-3,4-dimethylpiperazin-1-yl)azetidine-1-yl)-5-fluoropyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, 4-(((6S,9aS)-1-(benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate, and, 4-(((6S,9aS)-1-(benzylcarbamoyl)-8-((6-(3-(4-ethylpiperazin-1-yl)azetidin-1-yl)pyridin-2-yl)methyl-4,7-dioxo-2-(prop-2-en-1-yl)-octahydro-1H-pyrazino[2,1-c][1,2,4]triazin-6-yl)methyl)phenyl dihydrogen phosphate.

8. A compound or pharmaceutically acceptable salt thereof selected from:

(6S,9aS)-N-benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2-fluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3S)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3R)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((2S)-2,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((5-fluoro-6-(3-(4-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-4,7-dioxo-2-(prop-2-en-1-yl)-8-((6-(3-(4-(propan-2-yl)piperazin-1-yl)azetidin-1-yl)pyridin-2-yl)methyl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((2S)-2,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3S)-3,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((2S)-2,4-dimethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-(3-((3S)-4-ethyl-3-methylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-8-((6-3-((3R)-4-ethyl-3-methylpiperazin-1-yl)azetidin-1-yl)pyridin-2-yl)methyl-6-((4-hydroxyphenyl)methyl)-4,7-dioxo-2-(prop-2-en-1-yl)-octahydro-1H-pyrazino[2,1-c][1,2,4]triazine-1-carboxamide, (6S,9aS)-N-benzyl-6-((2,6-difluoro-4-hydroxyphenyl)methyl)-8-((6-(3-((3S)-4-ethyl-3-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide, 4-(((6S,9aS)-1-(benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate, and 4-(((6S,9aS)-1-(benzylcarbamoyl)-8-((6-(3-(4-ethylpiperazin-1-yl)azetidin-1-yl)pyridin-2-yl)methyl-4,7-dioxo-2-(prop-2-en-1-yl)-octahydro-1H-pyrazino[2,1-c][1,2,4]triazin-6-yl)methyl)phenyl dihydrogen phosphate.

9. (6S,9aS)-N-Benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

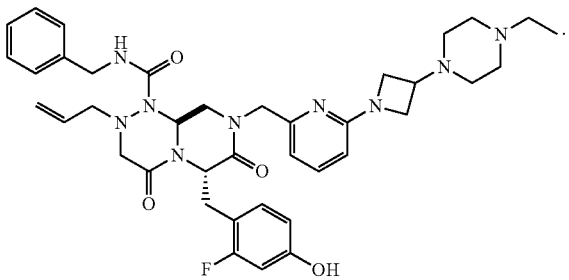

10. (6S,9aS)-N-Benzyl-8-((6-(3-(4-ethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

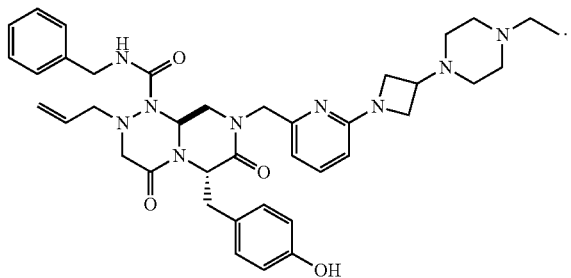

11. (6S,9aS)-N-Benzyl-6-((2-fluoro-4-hydroxyphenyl)methyl)-8-((6-(3-(4-methylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazine-1-carboxamide or a pharmaceutically acceptable salt thereof:

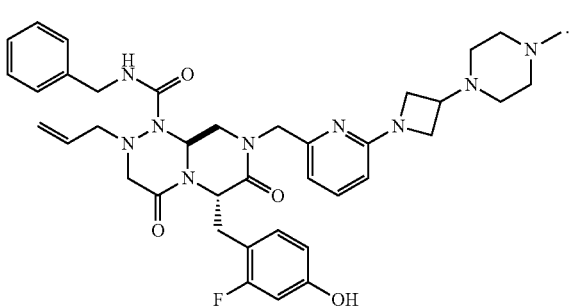

12. (6S,9aS)-N-Benzyl-8-((6-(3-((3S)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

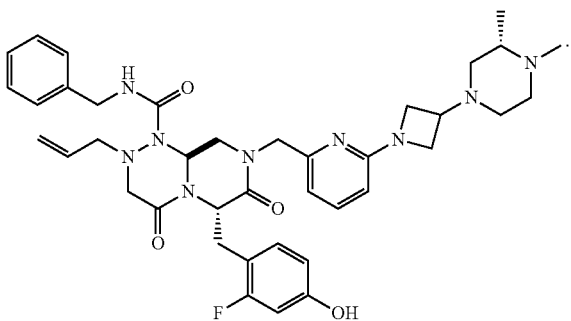

13. (6S,9aS)-N-Benzyl-8-((6-(3-((3R)-3,4-dimethylpiperazin-1-yl)azetidin-1-yl)pyridin-2-yl)methyl)-6-((2-fluoro-4-hydroxyphenyl)methyl)-4,7-dioxo-2-(prop-2-en 1-yl)-octahydro-1H-pyrazino[2,1-c][1,2,4]triazine-1-carboxamide or a pharmaceutically acceptable salt thereof:

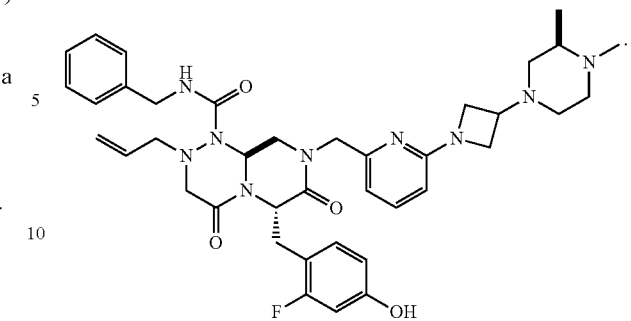

14. (6S,9aS)-N-Benzyl-8-((6-(3-((2S)-2,4-dimethylpiperazin-1-yl)azetidin-1-yl)pyridin-2-yl)methyl)-6-((4-hydroxyphenyl)methyl)-4,7-dioxo-2-(prop-2-en-1-yl)-octahydro-1H-pyrazino[2,1-c][1,2,4]triazine-1-carboxamide or a pharmaceutically acceptable salt thereof:

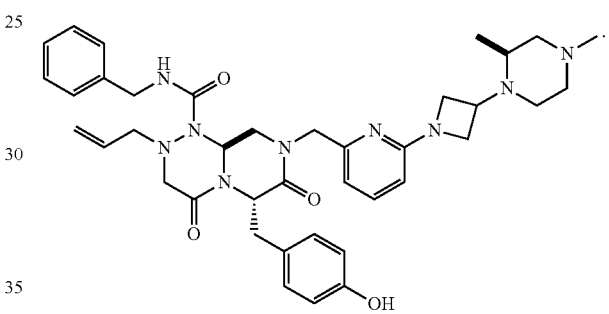

15. 4-((((6S,9aS)-1-(Benzylcarbamoyl)-8-((6-(3-(4-ethylpiperazin-1-yl)azetidin-1-yl)pyridin-2-yl)methyl)-4,7-dioxo-2-(prop-2-en-1-yl)-octahydro-1H-pyrazino[2,1-c][1,2,4]triazin-6-yl)methyl)-3-fluorophenyl dihydrogen phosphate or a pharmaceutically acceptable salt thereof:

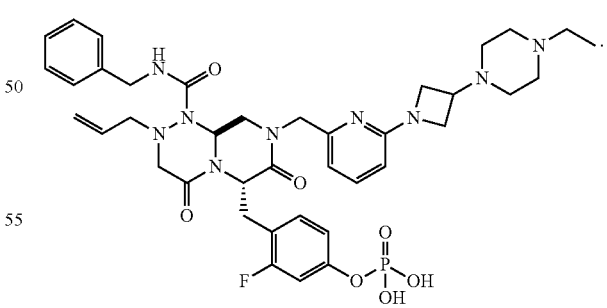

16. 4-((((6S,9aS)-1-(Benzylcarbamoyl)-8-((6-(3-(4-ethylpiperazin-1-yl)azetidin-1-yl)pyridin-2-yl)methyl-4,7-dioxo-2-(prop-2-en-1-yl)-octahydro-1H-pyrazino[2,1-c][1,2,4]triazin-6-yl)methyl)phenyl dihydrogen phosphate or a pharmaceutically acceptable salt thereof:

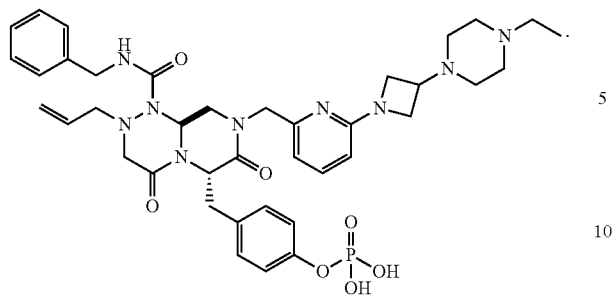
17. A pharmaceutical composition comprising the compound or pharmaceutically acceptable salt thereof according to any one of claims 1 to 16.
* * * * *

UNITED STATES PATENT AND TRADEMARK OFFICE
CERTIFICATE OF CORRECTION

PATENT NO.         : 9,174,998 B2                                      Page 1 of 1
APPLICATION NO.    : 14/577660
DATED              : November 3, 2015
INVENTOR(S)        : Satoshi Inoue et al.

It is certified that error appears in the above-identified patent and that said Letters Patent is hereby corrected as shown below:

In the claims,

Column 127, claim 2

Line 28, delete "R" and replace it with -- $R^1$ --.

Column 131, claim 13

Line 65, delete "en 1" and replace it with -- en-1 --.

Signed and Sealed this
Twenty-third Day of February, 2016

Michelle K. Lee
*Director of the United States Patent and Trademark Office*

```
SEQUENCE LISTING

<160> NUMBER OF SEQ ID NOS: 2

<210> SEQ ID NO 1
<211> LENGTH: 43
<212> TYPE: DNA
<213> ORGANISM: Artificial Sequence
<220> FEATURE:
<223> OTHER INFORMATION: BEHKS-F

<400> SEQUENCE: 1
gatctgaatt caagcttctc gagggtacct ctagagagct cgc        43

<210> SEQ ID NO 2
<211> LENGTH: 43
<212> TYPE: DNA
<213> ORGANISM: Artificial Sequence
<220> FEATURE:
<223> OTHER INFORMATION: BEHKS-R

<400> SEQUENCE: 2
ggccgcgagc tctctagagg taccctcgag aagcttgaat tca        43
```